(12) United States Patent
Sato et al.

(10) Patent No.: US 6,872,823 B1
(45) Date of Patent: Mar. 29, 2005

(54) PROCESS FOR PRODUCING BENZOXAZINE DERIVATIVE AND PRODUCTION INTERMEDIATE THEREOF

(75) Inventors: Kouji Sato, Edogawa-ku (JP); Yoshihiro Takayanagi, Edogawa-ku (JP); Katsuhiko Okano, Edogawa-ku (JP); Keiji Nakayama, Edogawa-ku (JP); Akihiro Imura, Edogawa-ku (JP); Mikihiro Itoh, Edogawa-ku (JP); Tsutomu Yagi, Edogawa-ku (JP); Yukinari Kobayashi, Edogawa-ku (JP); Tomoyuki Nagai, Edogawa-ku (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/070,556

(22) PCT Filed: Sep. 7, 2000

(86) PCT No.: PCT/JP00/06094

§ 371 (c)(1),
(2), (4) Date: Jun. 21, 2002

(87) PCT Pub. No.: WO01/18005

PCT Pub. Date: Mar. 15, 2001

(30) Foreign Application Priority Data

| Sep. 8, 1999 | (JP) | ........................... 11/253958 |
| Sep. 30, 1999 | (JP) | ........................... 11/278019 |
| Aug. 8, 2000 | (JP) | ........................... 2000/239256 |
| Aug. 8, 2000 | (JP) | ........................... 2000/239262 |

(51) Int. Cl.[7] ................. C07D 498/06; A61K 31/5365; A61P 31/04
(52) U.S. Cl. ..................................... 544/101; 544/105
(58) Field of Search ................................ 544/101, 105

(56) References Cited

U.S. PATENT DOCUMENTS

| 4,985,557 A | 1/1991 | Hayakawa et al. |
| 5,312,999 A | 5/1994 | Fujiwara et al. |
| 5,644,056 A | 7/1997 | Saukaitis ..................... 544/105 |

FOREIGN PATENT DOCUMENTS

| EP | 0 322 815 A2 | 7/1989 |

OTHER PUBLICATIONS

International Search Report.
Xie, Lun Jia, "A facile synthesis of Chiral 3–Alkyl–3, 4–Dihydro–2H–1, 4–Benzoxazine Derivatives", Chinese Chemical Letters, vol. 6, No. 10 (1995) pp. 857–860.

*Primary Examiner*—Mark L. Berch
*Assistant Examiner*—Kahsay Habte
(74) *Attorney, Agent, or Firm*—Sughrue Mion, PLLC

(57) ABSTRACT

Processes for producing antibacterial agents and intermediates useful in producing antibacterial agents are provided and include producing compound (VI-a) in accordance with the following reaction schema, as well as production intermediates thereof.

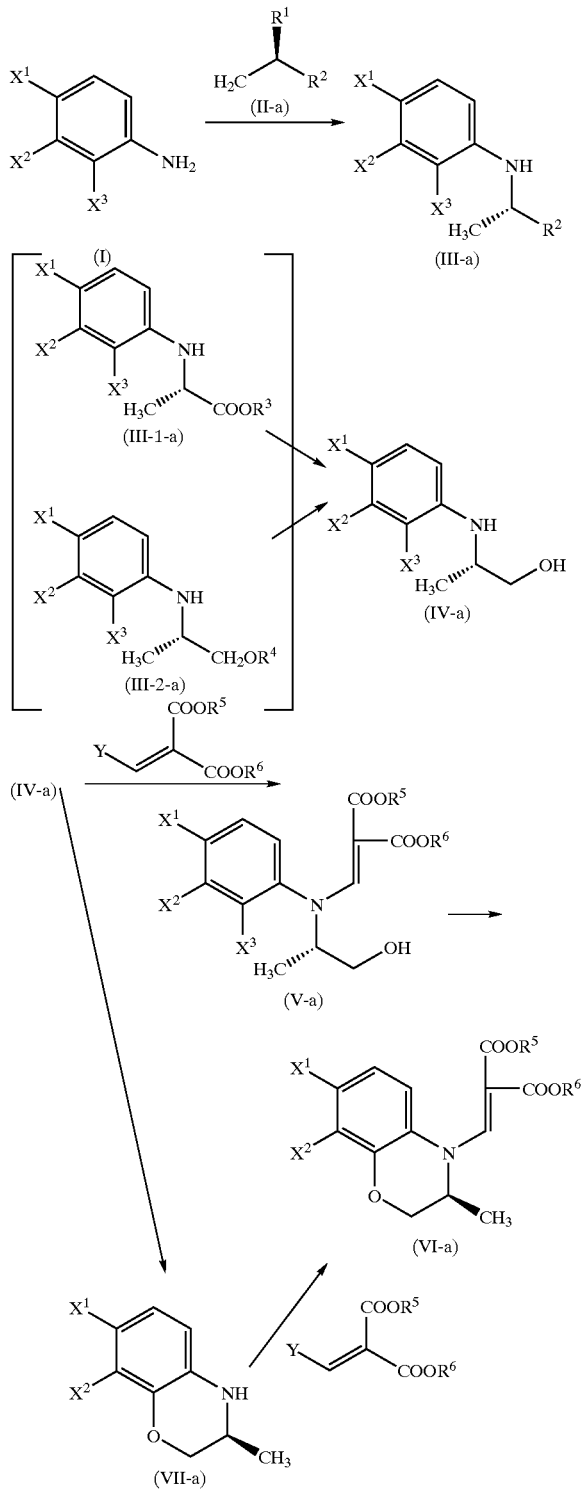

17 Claims, No Drawings

PROCESS FOR PRODUCING BENZOXAZINE DERIVATIVE AND PRODUCTION INTERMEDIATE THEREOF

TECHNICAL FIELD

The present invention relates to intermediates which are useful in producing antibacterial compounds and processes for producing the same.

BACKGROUND ART (3S)-(−)9-fluoro-3-methyl-10-(4-methyl-1-piperazinyl)-7-oxo-2,3-dihydro-7H-pyrido[1,2,3-de][1,4]benzoxazine-6-carboxylic acid (levoflaxacin, LVFX: JP-A-62-252790, the term "JP-A" as used herein means an "unexamined published Japanese patent application.)

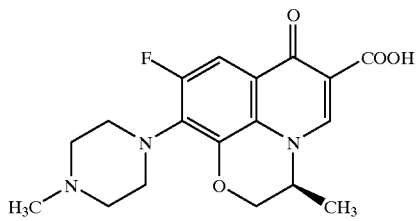

is known as an excellent synthetic antibacterial agent.

As intermediates in the production of this levofloxacin, compounds represented by formula (VI-a) (hereinafter referred to as compounds (VI-a); the same will apply to compounds represented by other formulae) are also useful:

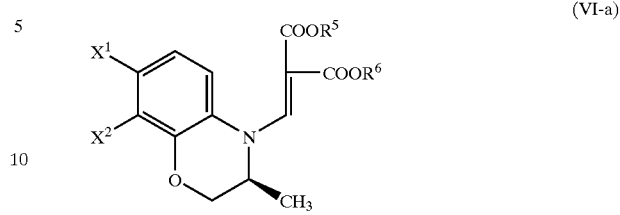

(wherein $X^1$ and $X^2$, each independently represents a halogen atom).

As intermediates for racemic 9-fluoro-3-methyl-10-(4-methyl-1-piperazinyl)-7-oxo-2,3-dihydro-7H-pyrido[1,2,3-de][1,4]benzoxazine-6-carboxylic acid (oflxacin, OFLX):

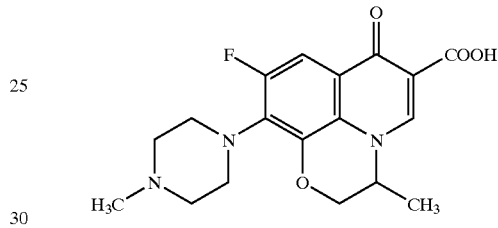

compounds represented by formula (VI):

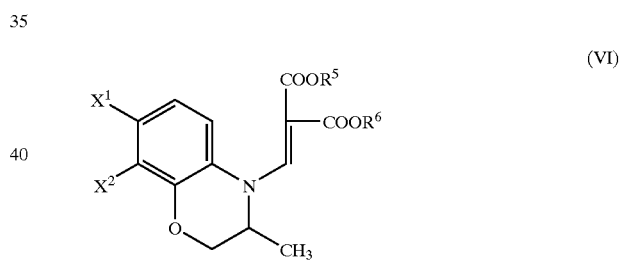

(wherein $X^1$ and $X^2$, each independently represents a halogen atom; and $R^5$ and $R^6$, each independently represents an alkyl group) are useful.

Conventional processes for producing the compound (VI-a) are as follows.

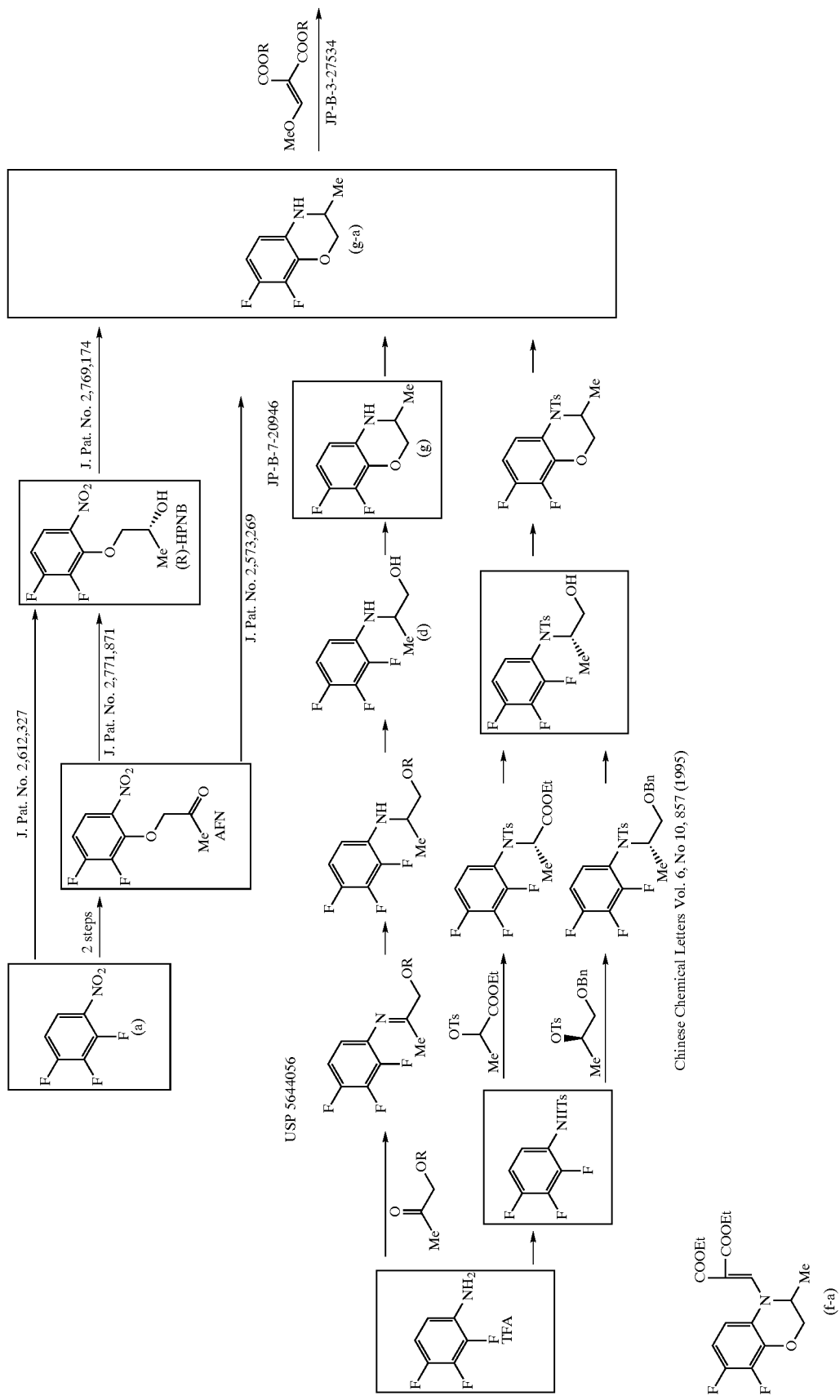

The production process reported by Japanese Patent No. 2,612,327 shown in the above figure suffers from a problem that epimerization arises under basic or acidic conditions and thus the yield of optically active (R)-NPNB is lowered.

In the process reported by Japanese Patent No. 2,771,871 which is a microbial reduction method, it is troublesome to purify the product since the physical properties of the product are not so largely different from those of the starting material.

Further, the process reported by Japanese Patent No. 2,573,269 leaves much to be improved as an industrial process, since an expensive asymmetric acyloxyboron alkali metal hydride is used therein as a reducing agent.

In the optical resolution method reported by JP-B-7-20946 (the term "JP-B" as used herein means an "examined Japanese patent publication), furthermore, it is needed to explore the reuse of the unnecessary isomer which is formed theoretically at a ratio of 50%.

The production process reported by U.S. Pat. No. 5,644,056 relates to a reaction of a racemate. To produce levofloxacin by this process, therefore, it is required to optically resolve the obtained product and the unnecessary isomer should be racemized or inverted. In addition, the specification of this patent discloses no experimental example of optically active compound.

The process reported by the Chinese document (Chinese Chemical Letters Vol.6, No.10, 857–860 (1995)) suffers from a problem that an additional step is needed for the deprotection of the p-toluenesulfonyloxy group used as a protective group.

DISCLOSURE OF THE INVENTION

The present invention relates to processes by which the compound (VI-a) important as intermediate in the production of levofloxacin can be economically synthesized within a short period and which are thus industrially favorable production process. As a result of intensive studies, the present inventors have found out that the object can be achieved by producing an intermediate of levofloxacin in accordance with the following synthesis pathways, thus completing the present invention. The following figure shows the processes according to the present invention for producing the compound (VI) from the compound (I).

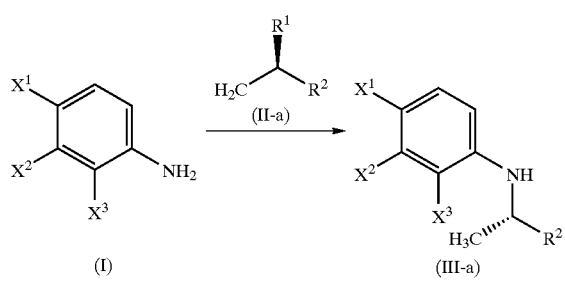

Accordingly, the present invention provides processes for industrially advantageously producing compound represented by the formula (VI-a) which is an intermediate for industrially advantageously producing levofloxacin:

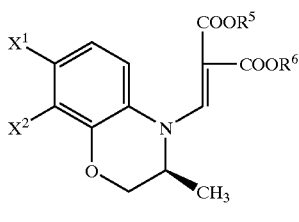

(VI-a)

Namely, the present invention relates the following processes.

Process A:

A process which comprises reacting a compound represented by formula (I):

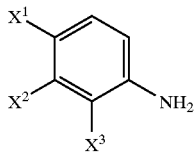

(I)

with a compound represented by formula (II-1-a) in the presence of a base:

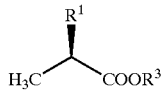

(II-1-a)

to give a compound represented by formula (III-1-a):

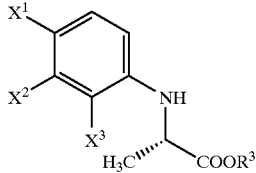

(III-1-a)

reducing this compound into a compound represented by formula (IV-a):

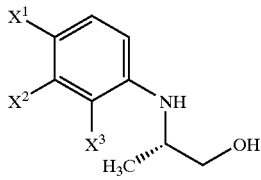

(IV-a)

reacting this compound with a compound represented by the following formula:

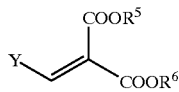

to give a compound represented by formula (V-a):

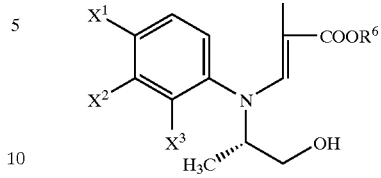

(V-a)

and then treating this compound in the presence of a base.

Process B:

A process which comprises reacting a compound represented by formula (I):

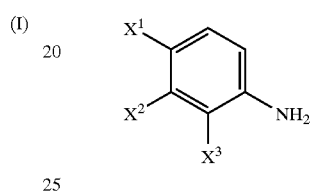

(I)

with a compound represented by formula (II-2-a) in the presence of a base:

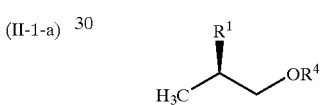

(II-2-a)

to give a compound represented by formula (III-2-a):

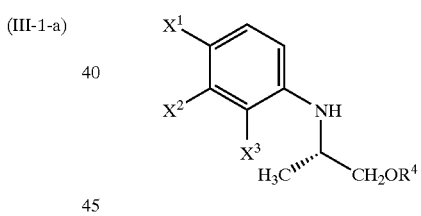

(III-2-a)

eliminating the hydroxyl-protective group (the substituent $R^4$) of this compound to give a compound represented by formula (IV-a):

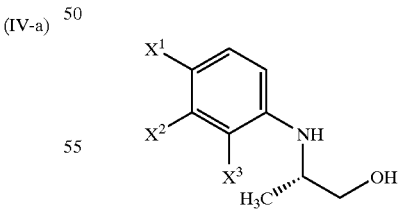

(IV-a)

reacting this compound with a compound represented by the following formula:

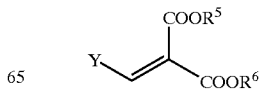

to give a compound represented by formula (V-a):

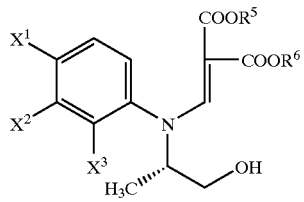

and then treating this compound in the presence of a base.

Process C:

A process which compreses reacting a compound represented by formula (I):

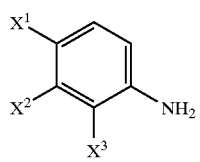

with a compound represented by formula (II-1-a) in the presence of a base:

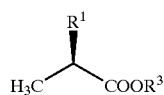

to give a compound represented by formula (III-1-a):

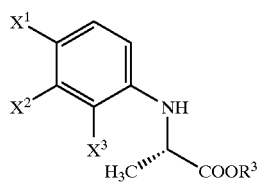

reducing this compound into a compound represented by formula

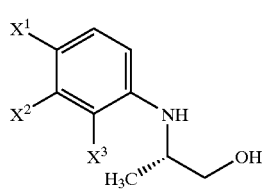

treating this compound in the presence of a base to give a compound represented by formula (VII-a):

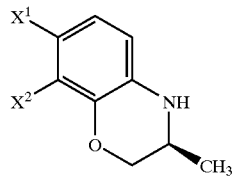

and reacting this compound with a compound represented by the following formula:

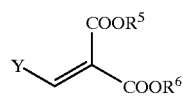

Process D:

A process which comprises reacting a compound represented by formula (I):

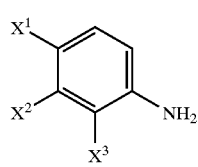

with a compound represented by formula (II-2-a) in the presence of a base:

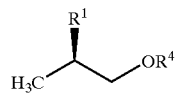

to give a compound represented by formula (III-2-a):

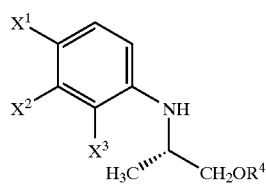

eliminating the hydroxyl-protective group (the substituent $R^4$) of this compound to give a compound represented by formula (IV-a):

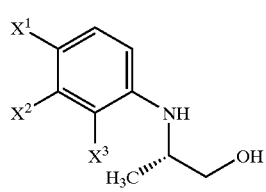

treating this compound in the presence of a base to give a compound represented by formula (VII-a):

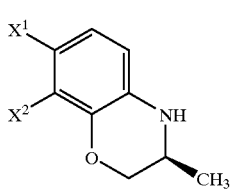
(VII-a)

and then reacting this compound with a compound represented by the following formula:

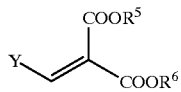

Process E:

A process which comprises reacting a compound represented by the formula (I):

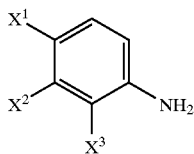
(I)

with a compound represented by formula (II-1) in the presence of a base:

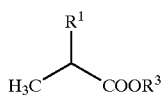
(II-1)

to give a compound represented by formula (III-1):

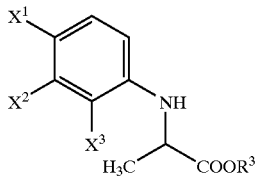
(III-1)

and then subjecting this compound to the following Method 1 or 2;

Method 1:
in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism and, after the completion of this treatment, isolating the product from the treated liquid mixture;

Method 2:
in case of the compound represented by the formula (III-1) where $R^3$ is a hydrogen atom, a method which comprises optically resolving this compound by reacting with an optically active organic base;

to obtain a carboxylic acid compound represented by the following formula:

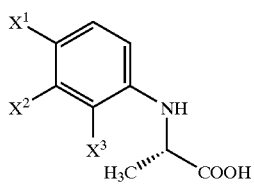

esterifying this compound in the presence of an alcohol represented by the following formula:

$R^7$—OH to give an ester compound represented by the following formula:

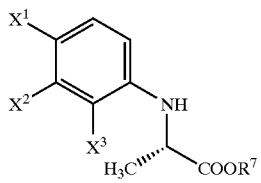

reducing this compound into a compound represented by formula (IV-a):

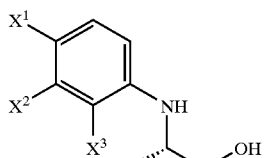
(IV-a)

reacting this compound with a compound represented by the following formula:

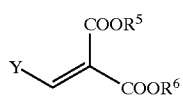

to give a compound represented by formula (V-a):

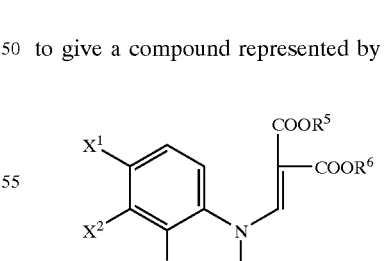
(V-a)

and then treating this compound in the presence of a base.

Process F:

A process which comprises reacting a compound represented by formula (I):

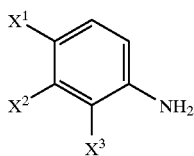
(I)

with a compound represented by formula (II-1) in the presence of a base:

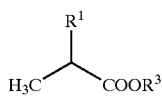
(II-1)

to give a compound represented by formula (III-1):

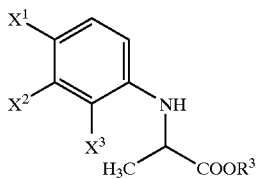
(III-1)

and then subjecting this compound to the following Method 1 or 2;

Method 1:
in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism and, after the completion of this treatment, isolating the product from the treated liquid mixture;

Method 2:
in case of the compound represented by the formula (III-1) where $R^3$ is a hydrogen atom, a method which comprises optically resolving this compound by reacting with an optically active organic base;

to obtain a carboxylic acid compound represented by the following formula:

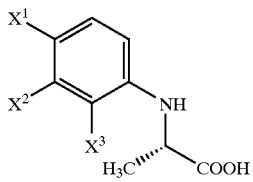

esterifying this compound in the presence of an alcohol represented by the following formula:

$R^7$—OH to give an ester compound represented by the following formula:

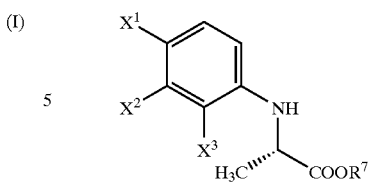

reducing this compound into a compound represented by formula (IV-a):

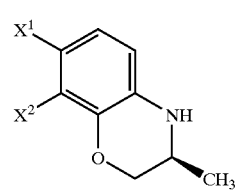
(IV-a)

treating this compound in the presence of abase to give a compound represented by formula (VII-a):

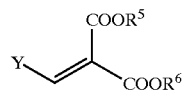
(VII-a)

and then reacting this compound with a compound represented by the following formula:

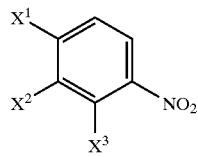

Process G:
A process which comprises reacting a compound represented by the following formula:

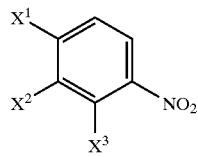

or by the following formula:

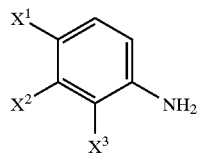

with a compound represented by the following formula in the presence of a metal catalyst under a hydrogen gas atmosphere, optionally in the presence of a dehydrating agent or an acid:

$CH_3COCOOR^3$ to give a compound represented by formula (III-1):

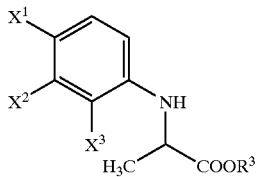
(III-1)

and then subjecting this compound to the following Method 1 or 2;

Method 1:

in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism and, after the completion of this treatment, isolating the product from the treated liquid mixture;

Method 2:

in case of the compound represented by the formula (III-1) where $R^3$ is a hydrogen atom, a method which comprises optically resolving this compound by reacting with an optically active organic base;

to obtain a carboxylic acid compound represented by the following formula:

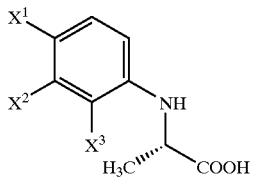

esterifying this compound in the presence of an alcohol represented by the following formula:

$R^7$—OH to give an ester compound represented by the following formula:

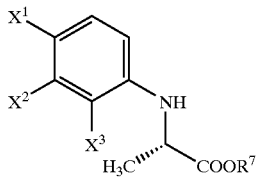

reducing the compound into a compound represented by formula (IV-a):

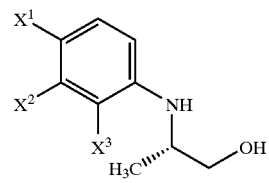
(IV-a)

reacting this compound with a compound represented by the following formula:

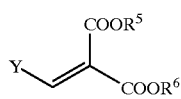

to give a compound represented by formula (V-a):

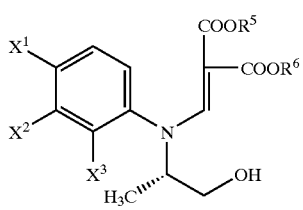
(V-a)

and then treating this compound in the presence of a base.

Process H:

A process which comprises reacting a compound represented by the following formula:

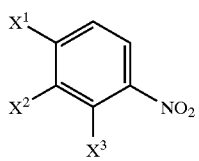

or by the following formula:

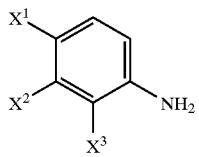

with a compound represented by the following formula in the presence of a metal catalyst under a hydrogen gas atmosphere, optionally in the presence of a dehydrating agent or an acid:

$CH_3COCOOR^3$ to give a compound represented by formula (III-1):

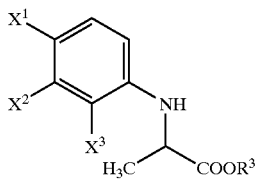
(III-1)

and then subjecting this compound to the following Method 1 or 2;

Method 1:

in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism and, after the completion of this treatment, isolating the product from the treated liquid mixture;

Method 2:

in case of the compound represented by the formula (III-1) where $R^3$ is a hydrogen atom, a method which comprises optically resolving this compound by reacting with an optically active organic base;

to obtain a carboxylic acid compound represented by the following formula:

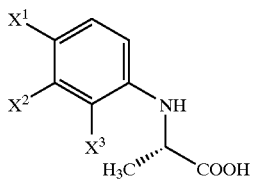

esterifying this compound in the presence of an alcohol represented by the following formula:

$R^7$—OH to give an ester compound represented by the following formula:

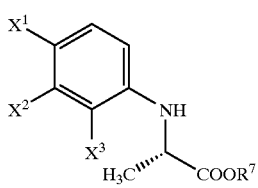

reducing the compound into a compound represented by formula (IV-a):

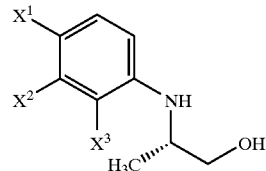
(IV-a)

treating this compound in the presence of a base to give a compound represented by formula (VII-a):

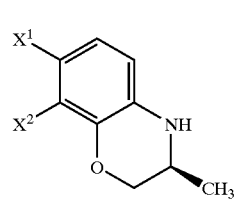
(VII-a)

and then reacting this compound with a compound represented by the following formula:

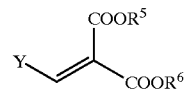

Process I:

A process which comprises reacting a compound represented by the following formula:

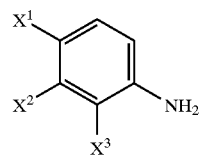

with a compound represented by the following formula:

$CH_3COCOOR^3$ to give a compound represented by the following formula:

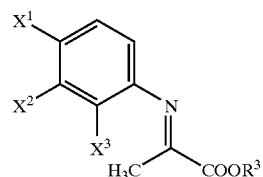

asymmetrically reducing this compound into a compound represented by formula (III-1-a):

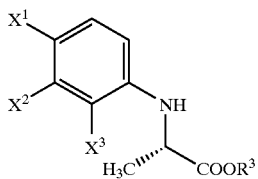

(III-1-a)

reducing this compound into a compound represented by formula (IV-a):

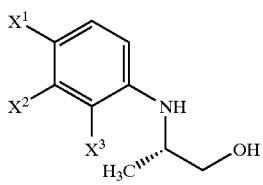

(IV-a)

reacting this compound with a compound represented by the following formula:

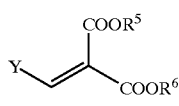

to give a compound represented by formula (V-a):

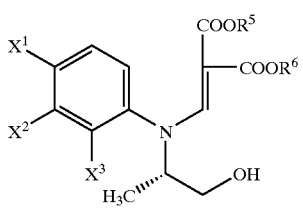

(V-a)

and then treating this compound in the presence of a base.

Process J:

A process which comprises reacting a compound represented by the following formula:

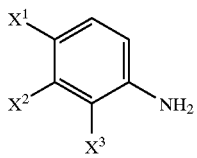

with a compound represented by the following formula:

$CH_3COCOOR^3$ to give a compound represented by the following formula:

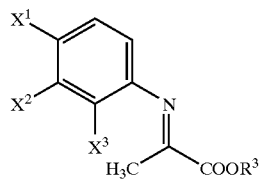

asymmetrically reducing this compound into a compound represented by formula (III-1-a):

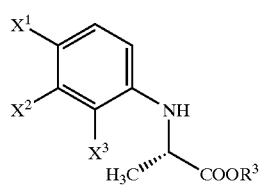

(III-1-a)

reducing this compound into a compound represented by formula (IV-a):

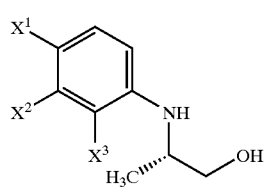

(IV-a)

treating this compound in the presence of a base to give a compound represented by formula (VII-a):

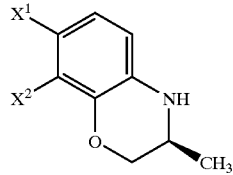

(VII-a)

and then reacting this compound with a compound represented by the following formula:

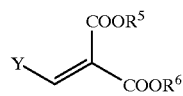

[in each of the above formulae, $X^1$, $X^2$ and $X^3$, each independently represents a halogen atom; $R^1$ represents a leaving group; $R^3$ represents a hydrogen atom or a carboxyl-protective group; $R^4$ represents a hydroxyl-protective group; $R^5$ and $R^6$, each independently represents an alkyl group having 1 to 6 carbon atoms; $R^7$ represents a carboxyl-protective group; and Y represents an alkoxy group having 1 to 6 carbon atoms, a halogen atom or a dialkylamino group (wherein the alkyl groups may be the same or different and each represents an alkyl group having 1 to 6 carbon atoms); and substituents which will be used hereinafter respectively have the same meanings as defined above].

The present invention further relates to the following processes constituting each of the Processes as described above.

Concerning the processes for producing the compound represented by the formula (III-a) in Processes G and H;
a process for producing a compound represented by the formula (III-1):

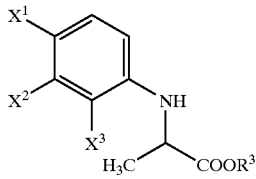
(III-1)

which is characterized by reacting a compound represented by formula (I-0):

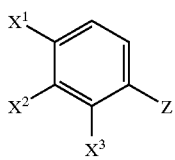
(I-0)

(wherein Z represents a nitro group or an amino group; and other groups are those as defined above;)
with a compound represented by the following formula;

CH$_3$COCOOR$^1$ optionally in the presence of an acid acceptor or an acid, in the presence of a metal catalyst under a hydrogen gas atmosphere;
the above process for producing a compound represented by the formula (III-1) wherein R$^3$ is a hydrogen atom;
the above process for producing a compound represented by the formula (III-1) wherein R$^3$ is a methyl group;
the above process for producing a compound represented by the formula (III-1) wherein R$^3$ is an ethyl group;
the above process for producing a compound represented by the formula (III-1) wherein Z is an amino group;
the above process for producing a compound represented by the formula (III-1) wherein Z is a nitro group;
the above process for producing a compound represented by the formula (III-1) wherein Z is an amino group and R$^3$ is a hydrogen atom;
the above process for producing a compound represented by the formula (III-1) wherein Z is an amino group and R$^3$ is a methyl group;
the above process for producing a compound represented by the formula (III-1) wherein Z is an amino group and R$^3$ is an ethyl group;
the above process for producing a compound represented by the formula (III-1) wherein Z is a nitro group and R$^3$ is a hydrogen atom;
the above process for producing a compound represented by the formula (III-1) wherein Z is a nitro group and R$^3$ is a methyl group; and
the above process for producing a compound represented by the formula (III-1) wherein Z is a nitro group and R$^3$ is an ethyl group.
Concerning the processes involving the separation of a single optical isomer in Processes E, F, G and B;
a process for producing a carboxylic acid compound represented by the following formula:

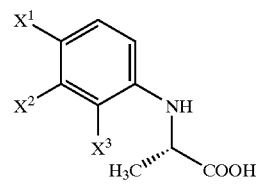

which is characterized by treating an ester compound among the compounds represented by formula (III-1):

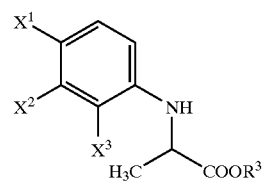
(III-1)

with an enzyme capable of asymmetrically hydrolyzing an ester or a liquid culture medium of a microorganism, cells of this microorganism or processed cells of this microorganism and then isolating the product from the treated liquid mixture;
a process for producing a carboxylic acid compound represented by the following formula:

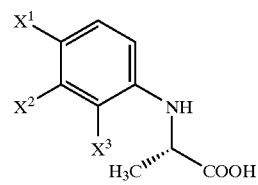

which is characterized by treating an ester compound among the compounds represented by formula (III-1):

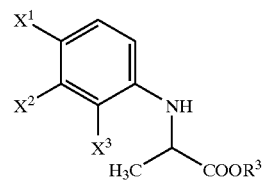
(III-1)

with an enzyme capable of asymmetrically hydrolyzing an ester or a liquid culture medium of a microorganism, cells of this microorganism or processed cells of this microorganism and then removing a compound represented by formula (III-1-b) from the treated liquid mixture;

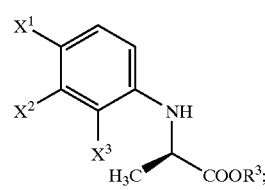
(III-1-b)

a process for producing an ester compound among the compounds represented by formula (III-1-a):

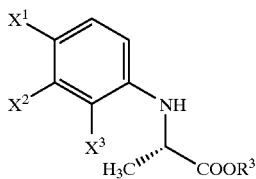
(III-1-a)

which is characterized by treating an ester compound among the compounds represented by formula (III-1):

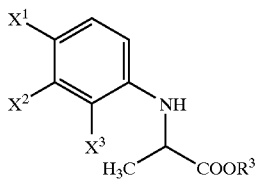
(III-1)

with an enzyme capable of asymmetrically hydrolyzing an ester or a liquid culture medium of a microorganism, cells of this microorganism or processed cells of this microorganism and then isolating the product from the treated liquid mixture;

a process for producing an ester compound among the compounds represented by the formula (III-1-a):

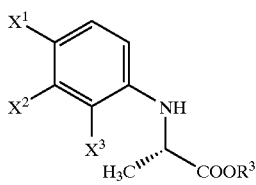
(III-1-a)

which is characterized by treating an ester compound among the compounds represented by formula (III-1):

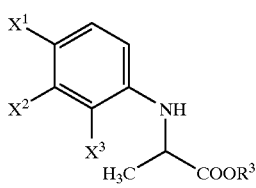
(III-1)

with an enzyme capable of asymmetrically hydrolyzing an ester or a liquid culture medium of a microorganism, cells of this microorganism or processed cells of this microorganism and then removing a carboxylic acid compound represented by the following formula from the treated liquid mixture;

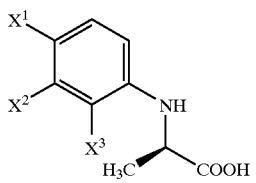

each of the above-described production processes wherein $R^3$ is a methyl group;

each of the above-described production processes wherein $R^3$ is an ethyl group;

each of the above-described production processes wherein the enzyme to be used in the treatment is esterase, protease or chymotrypsin;

each of the above-described production processes wherein the microorganism is a microorganism selected from among bacteria belonging to the genera *Bacillus, Micrococcus* and *Actinomyces;* each of the above-described production processes wherein the microorganism is a microorganism selected from among fungi belonging to the genera *Aspergillus, Rhizopus, Nannizia* and *Penicillium;* and each of the above-described production processes wherein the microorganism is a microorganism selected from among yeasts belonging to the genera *Candida, Saccharomyces* and *Zygoascus.*

Concerning the processes involving the separation of a single optical isomer in Processes E, F, G and H;

a process for producing a 2-(2,3,4-trihalogenoanilino) propionic acid composed of a single optical isomer, which is characterized by optically resolving a compound represented by the following formula:

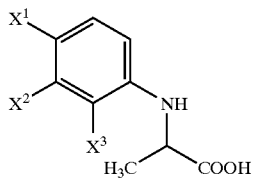

by using an optically active organic base;

a process for producing a 2-(2,3,4-trihalogenoanilino) propionic acid composed of a single optical isomer, which is characterized by treating a compound represented by the following formula:

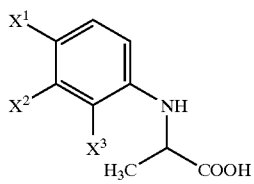

with an optically active organic base to give a diastereomeric salt of one of the optical isomers of 2-(2,3,4-trihalogenoanilino)propionic acid and the optically active organic base and then treating this diastereomeric salt with an acid;

the above-described processes for producing a single optical isomer wherein the optically active organic base is a compound represented by the following formula:

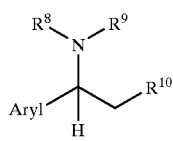

(wherein Aryl represents an aryl group optionally having a halogen atom, a nitro group, a cyano group, a carbamoyl group, an alkyl group having 1 to 6 carbon atoms or an alkoxy group having 1 to 6 carbon atoms; and $R^8$, $R^9$ and $R^{10}$, each independently represents:

(1) a phenyl group optionally having a halogen atom, an alkyl group having 1 to 6 carbon atoms, a halogenoalkyl group having 1 to 6 carbon atoms, an alkoxy group having 1 to 6 carbon atoms, a nitro group, a carbamoyl group or a cyano group;

(2) a benzyl group optionally having a halogen atom, an alkyl group having 1 to 6 carbon atoms, a halogenoalkyl group having 1 to 6 carbon atoms, an alkoxy group having 1 to 6 carbon atoms, a nitro group, a carbamoyl group or a cyano group;

(3) an alkyl group having 1 to 6 carbon atoms; or (4) a hydrogen atom);

the above-described processes for producing a single optical isomer wherein the optically active organic base is 1-phenylethylamine;

the above-described processes for producing a single optical isomer wherein the optically active organic base is 1-(p-tolyl)ethylamine; and the above-described processes for producing a single optical isomer wherein the optically active organic base is 1-phenyl-2-(tolyl)ethylamine.

Concerning the production processes involving the separation of a single optical isomer in Processes E, F, G and H;

a process for producing an ester compound represented by the following formula:

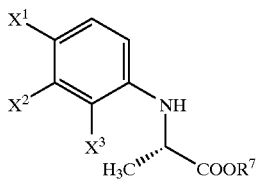

which is characterized by treating a carboxylic acid compound represented by the following formula:

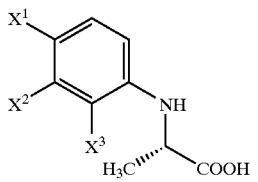

in the presence of a compound represented by the following formula:

and an acid catalyst; and a process for producing an ester compound represented by the following formula:

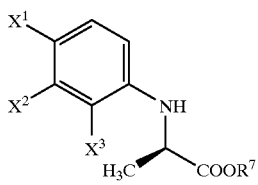

which is characterized by treating a carboxylic acid compound represented by the following formula:

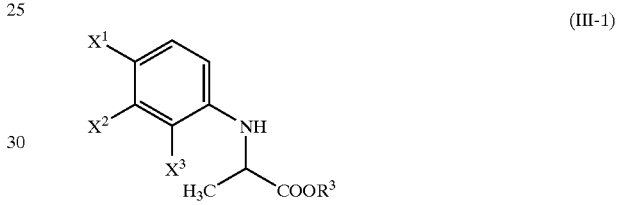

in the presence of a compound represented by the following formula:

and an acid catalyst.

Concerning the production processes involving the separation of a single optical isomer in Processes E, F, G and H;

a process for producing an ester compound in a racemate represented by formula (III-1):

(III-1)

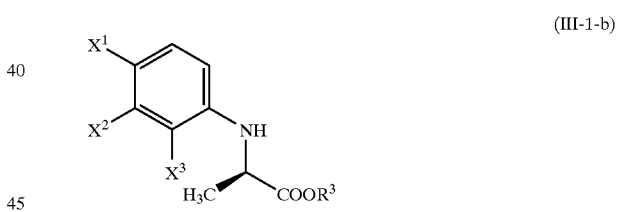

which is characterized by treating an ester compound among the compounds represented by formula (III-1-b):

(III-1-b)

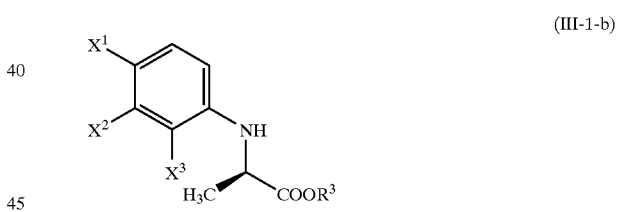

in the presence of a base;

a process for producing an ester compound as described above wherein the base is a nitrogen-containing heterocyclic compound;

a process for producing an ester compound as described above wherein the base is 1,8-diazabicyclo[5.4.0]undec-7-ene (DBU) or 1,8-diazabicyclo[4.3.0]undec-5-ene (DBN);

a process for producing an ester compound as described above wherein the base is an alkali metal or alkaline earth metal carbonate; and a process for producing an ester compound as described above wherein the base is potassium carbonate.

Concerning the production processes involving the separation of a single optical isomer in Processes E, F, G and H;

a process for producing a racemic carboxylic acid compound represented by the following formula:

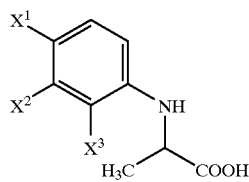

which is characterized by racemizing an ester compounds among the compounds represented by the following formula (III-1-b) by treating in the presence of a base:

(III-1-b)
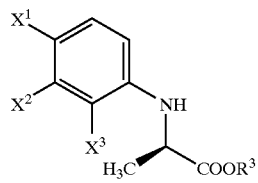

and then hydrolyzing;

a process for producing a racemic carboxylic acid compound as described above wherein the base is a metal alkoxide;

a process for producing a racemic carboxylic acid compound as described above wherein the base is potassium tertiary butoxide;

a process for producing a racemic carboxylic acid compound as described above wherein the base is an alkali metal or alkaline earth metal carbonate;

a process for producing a racemic carboxylic acid compound as described above wherein the base is potassium carbonate.

Concerning the processes for producing the compound (V-a) in Processes A, B, E, G and I;

a process for producing a compound represented by tformula (V-a):

(V-a)
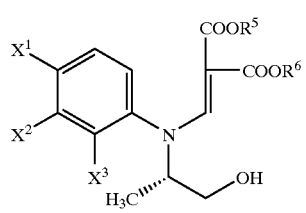

which is characterized by reacting a compound represented by formula (IV-a):

(IV-a)
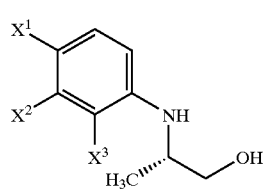

with a compound represented by the following formula under basic conditions:

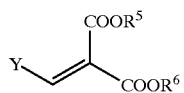

Concerning the processes for producing the compound (VI-a) in Processes A, B, E, G and I;

a process for producing a compound represented by formula (VI-a):

(VI-a)
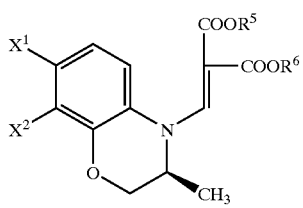

which is characterized by reacting a compound represented by the formula (V-a):

(V-a)
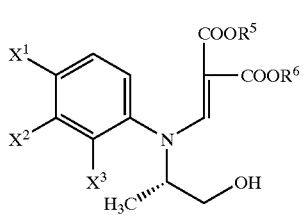

under basic conditions;

a process for producing a compound represented by the formula (VI-a) as described above wherein the basic conditions are basic conditions with the coexistence of a base and a phase transfer catalyst;

a process for producing a compound represented by the formula (VI-a) as described above wherein the base is an alkali metal hydroxide or an alkaline earth metal hydroxide;

a process for producing a compound represented by the formula (VI-a) as described above wherein the base is potassium hydroxide;

a process for producing a compound represented by the formula (VI-a) as described above wherein the phase transfer catalyst is a quaternary ammonium salt or a crown ether;

a process for producing a compound represented by the formula (VI-a) as described above wherein the phase transfer catalyst is a quaternary ammonium salt;

a process for producing a compound represented by the formula (VI-a) as described above wherein quaternary ammonium salt is tetra(normal-hexyl)ammonium chloride, trimethylbenzylammonium chloride, triethylbenzylammonium chloride, trimethylphenylammonium chloride or tetrabutylammonium hydrogen sulfate.

Concerning the steps of reducing an ester compound in Processes A, C, E, F, G, H, I and J;

a process for producing a compound represented by formula (IV-a):

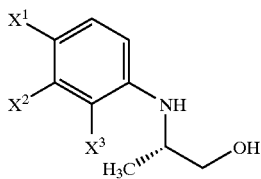

(IV-a)

which is characterized by treating a compound represented by formula (III-1-a):

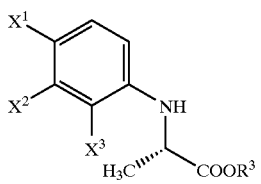

(III-1-a)

or a compound represented by the following formula:

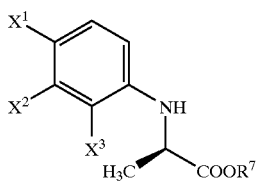

in an aprotic solvent with a metal borohydride compound and an alcohol;

a process for producing a compound represented by the formula (IV-a) as described above wherein the compound represented by the formula (III-1-a) is an ester compound;

a process for producing a compound represented by the formula (IV-a) as described above wherein $R^3$ and $R^7$ are each an alkyl group having 1 to 6 carbon atoms;

a process for producing a compound represented by the formula (IV-a) as described above wherein $R^3$ and $R^7$ are each a methyl group;

a process for producing a compound represented by the formula (IV-a) as described above wherein $R^3$ and $R^7$ are each an ethyl group;

each process for producing a compound represented by the formula (IV-a) as described above wherein the aprotic solvent is a solvent selected from the compounds of the group consisting of aromatic hydrocarbons, alkanes, cycloalkanes, ethers, halogenated hydrocarbons and acetic acid esters;

each process for producing a compound represented by the formula (IV-a) as described above wherein the aprotic solvent is an aromatic hydrocarbon;

each process for producing a compound represented by the formula (IV-a) as described above wherein the aprotic solvent is an alkane;

each process for producing a compound represented by the formula (IV-a) as described above wherein the aprotic solvent is a cycloalkalne;

each process for producing a compound represented by the formula (IV-a) as described above wherein the aprotic solvent is an ether;

each process for producing a compound represented by the formula (IV-a) as described above wherein the aprotic solvent is a halogenated hydrocarbon;

each process for producing a compound represented by the formula (IV-a) as described above wherein the aprotic solvent is an acetic acid ester;

each process for producing a compound represented by the formula (IV-a) as described above wherein the alcohol is a primary alcohol;

each process for producing a compound represented by the formula (IV-a) as described above wherein primary alcohol is methanol;

each process for producing a compound represented by the formula (IV-a) as described above wherein the metal borohydride compound is sodium borohydride; and each process for producing a compound represented by the formula (IV-a) as described above wherein $X^1$, $X^2$ and $X^3$ are each a fluorine atom.

Concerning the steps of reducing an ester compound in Processes A, B, E, G and I;

a process for producing a compound represented by formula (VI-a):

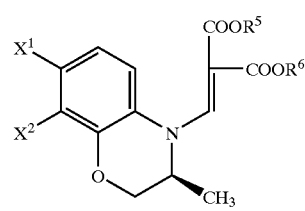

(VI-a)

which is characterized by reacting a compound represented by formula (III-1-a):

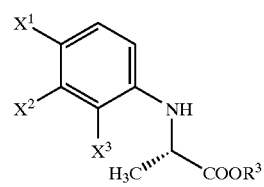

(III-1-a)

or a compound represented by the following formula:

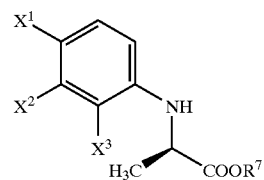

with a metal borohydride compound in an aprotic solvent in the presence of an alcohol to give a compound represented by formula (IV-a):

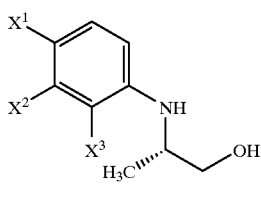
(IV-a)

then reacting this compound with a compound represented by the following formula under basic conditions:

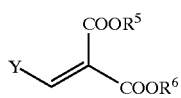

to give a compound represented by formula (V-a):

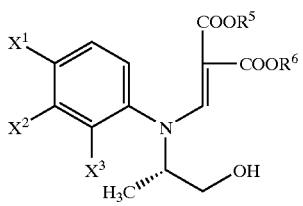
(V-a)

and treating this compound under basic conditions.

Moreover, the present invention relates to the following compounds concerning the above Processes and steps.

Compounds represented by formula (III-1):

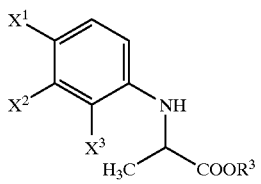
(III-1)

(wherein $X^1$, $X^2$ and $X^3$, each independently represents a halogen atom; and $R^3$ represents a hydrogen atom or a carboxyl-protective group);

compounds represented by formula (III-1-a):

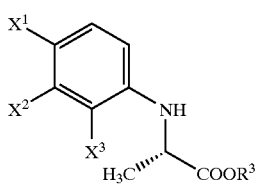
(III-1-a)

(wherein $X^1$, $X^2$ and $X^3$, each independently represents a halogen atom; and $R^3$ represents a hydrogen atom or a carboxyl-protective group);

compounds represented by formula (III-1-b):

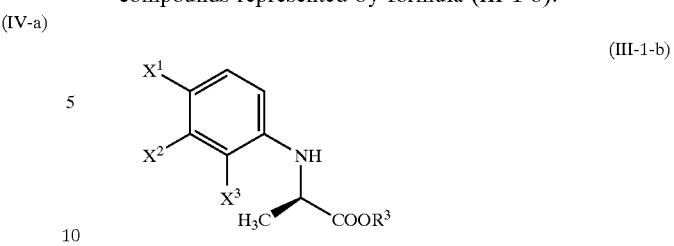
(III-1-b)

(wherein $X^1$, $X^2$ and $X^3$, each independently represents a halogen atom; and $R^3$ represents a hydrogen atom or an alkyl group);

each of the compounds of the formula (III-1), (III-1-a) or (III-1-b) wherein $R^3$ is a hydrogen atom;

each of the compounds of the formula (III-1), (III-1-a) or (III-1-b) wherein $R^3$ is a methyl group;

each of the compounds of the formula (III-1), (III-1-a) or (III-1-b) wherein $R^3$ is an ethyl group;

compounds represented by formula (V):

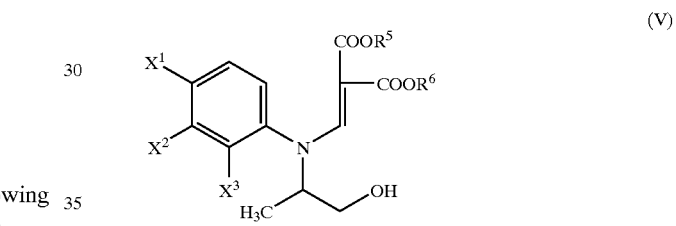
(V)

compounds represented by formula (V-a):

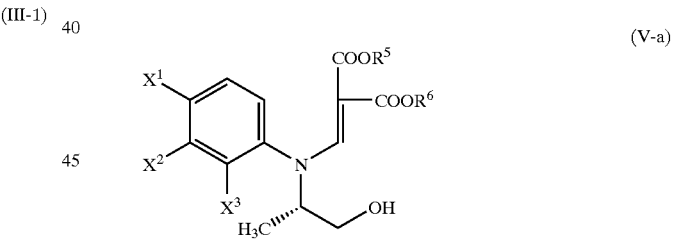
(V-a)

each of the compounds of the formula (III-1), (III-1-a), (III-1-b), (V) or (V-a) wherein $X^1$, $X^2$ and $X^3$ are each a fluorine atom;

salts of carboxylic acid compounds represented by the following formula:

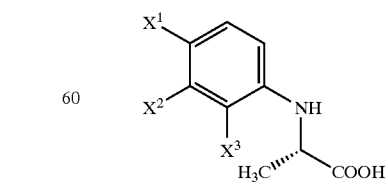

with an optically active organic base;

salts of compounds represented by the following formula:

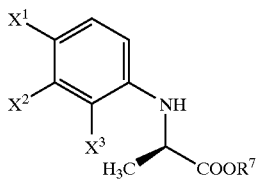

with an optically active organic base;

the above-described salts wherein the optically active organic base is a compound represented by the following formula:

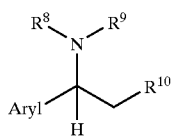

(wherein Aryl represents an aryl group optionally having a halogen atom, a nitro group, a cyano group, a carbamoyl group, an alkyl group having 1 to 6 carbon atoms or an alkoxy group having 1 to 6 carbon atoms; and $R^8$, $R^9$ and $R^{10}$, each independently represents:

(1) a phenyl group optionally having a halogen atom, an alkyl group having 1 to 6 carbon atoms, a halogenoalkyl group having 1 to 6 carbon atoms, an alkoxy group having 1 to 6 carbon atoms, a nitro group, a carbamoyl group or a cyano group;

(2) a benzyl group optionally having a halogen atom, an alkyl group having 1 to 6 carbon atoms, a halogenoalkyl group having 1 to 6 carbon atoms, an alkoxy group having 1 to 6 carbon atoms, a nitro group, a carbamoyl group or a cyano group;

(3) an alkyl group having 1 to 6 carbon atoms; or (4) a hydrogen atom);

the above-described salts wherein the optically active organic base is 1-phenylethylamine;

the above-described salts wherein the 1-phenylethylamine is (R)-(+)-1-phenyethylamine;

the above-described salts wherein the optically active organic base is 1-(p-tolyl)ethylamine;

the above-described salts wherein the 1-(p-tolyl) ethylamine is (R)-(+)-1-(p-tolyl)ethylamine;

the above-described salts wherein the optically active organic base is 1-phenyl-2-(p-tolyl)ethylamine;

the above-described salts wherein the 1-phenyl-2-(p-tolyl)ethylamine is (S)-(+)-1-phenyl-2-(p-tolyl) ethylamine;

each of the above-described salts wherein $X^1$, $X^2$ and $X^3$ are each a fluorine atom.

The present invention furthermore relates to a process for producing the compound (levofloxacin) represented by the following formula:

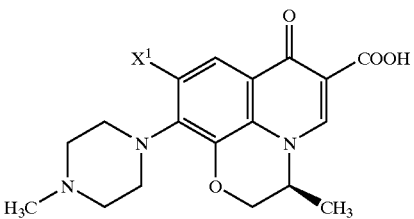

with the use of a compound represented by the formula (VI-a) which has been produced by each of the processes and each of the compounds as described above, which is characterized by involving the following steps of preparing a compound represented by formula (VI-a) by any of Processes A to J:

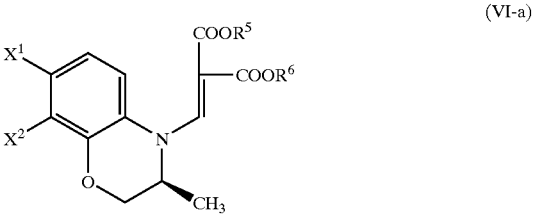

(VI-a)

treating this compound with a boron trifluoride compound to thereby convert it into a boron chelate compound represented by the following formula:

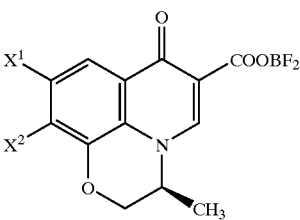

reacting this compound with 4-methylpiperazine to give a compound represented by the following formula:

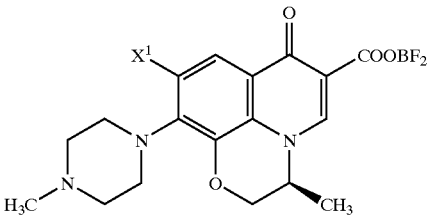

and then cleaving off the boron chelate of this compound.

The present invention furthermore relates to the following production processes:

a process for producing levofloxacin as described above wherein Process A is used as the process for producing the compound represented by the formula (VI-a);

a process for producing levofloxacin as described above wherein Process B is used as the process for producing the compound represented by the formula (VI-a);

a process for producing levofloxacin as described above wherein Process C is used as the process for producing the compound represented by the formula (VI-a);

a process for producing levofloxacin as described above wherein Process D is used as the process for producing the compound represented by the formula (VI-a);

a process for producing levofloxacin as described above wherein Process E is used as the process for producing the compound represented by the formula (VI-a);

a process for producing levofloxacin as described above wherein Process F is used as the process for producing the compound represented by the formula (VI-a);

a process for producing levofloxacin as described above wherein Process G is used as the process for producing the compound represented by the formula (VI-a);

a process for producing levofloxacin as described above wherein Process H is used as the process for producing the compound represented by the formula (VI-a);

a process for producing levofloxacin as described above wherein Process I is used as the process for producing the compound represented by the formula (VI-a);

a process for producing levofloxacin as described above wherein Process J is used as the process for producing the compound represented by the formula (VI-a);

a process for producing levofloxacin as described above wherein $X^1$ and $X^2$ are each a fluorine atom;

a process for producing levofloxacin as described above wherein the boron trifluoride compound is a boron trifluoride compound composed of boron trifluoride and an ether compound;

a process for producing levofloxacin as described above wherein the boron trifluoride compound is boron trifluoride diethyl ether complex or boron trifluoride tetrahydrofuran complex;

a process for producing levofloxacin as described above wherein the reaction with 4-methylpiperazine is a reaction carried out in the presence of a trialkylamine;

a process for producing levofloxacin as described above wherein the trialkylamine is triethylamine or tributylamine; etc.

Now, the present invention will be illustrated in greater detail. First, substituents used in the present description will be described.

$X^1$, $X^2$ and $X^3$, each independently represents a halogen atom, preferably a fluorine atom.

$R^1$ represents a leaving group. As the leaving group, halogenatoms, optionally substituted alkylsulfonyloxy groups, optionally substituted arylsulfonyloxy groups, etc. can be cited.

Examples of the optionally substituted alkylsulfonyloxy groups, methanesulfonyloxy group, ethanesulfonyloxy group, propanesulfonyloxy group, butanesulfonyloxy group, isobutanesulfonyloxy group, t-butanesulfonyloxy group and trifluoromethanesulfonyloxy group can be cited.

Examples of the optionally substituted arylsulfonyloxy groups, benzenesulfonyloxy group, p-toluenesulfonyloxy group, m-toluenesulfonyloxy group, p-nitrobenzenesulfonyloxy group, m-nitrobenzenesulfonyloxy group, p-methoxybenzenesulfonyloxy group, p-chlorobenzenesulfonyloxy group, m-chlorobenzenesulfonyloxy group, 2,4-dimethylbenzenesulfonyloxy group and 3,5-dinitrobenzenesulfonyloxy group can be cited.

As the leaving group, substituted sulfonyloxy groups and halogen atoms are preferable and trifluoromethanesulfonyloxy group, methanesulfonyloxy group, p-toluenesulfonyloxy group, chlorine atom, etc. are still preferable.

$R^1$ represents $-COOR^3$ or $-CH_2OR^4$.

$R^3$ represents a hydrogen atom or a carboxyl-protective group.

The carboxyl-group may be those ordinarily used in the art. Particular examples thereof include aralkyl groups, alkyl groups, etc.

The term aralkyl groups means groups composed of an alkyl group having 1 to 6 carbon atoms and an aryl group. Particular examples thereof include benzyl group, naphthyl methyl group, etc. The alkyl group may be a linear, branched or cyclic alkyl group having 1 to 6 carbon atoms. Particular examples thereof include methyl group, ethyl group, propyl group, cyclobutyl group, cyclopentyl group, cyclohexyl group, etc.

As $R^3$, alkyl groups having 1 to 6 carbon atoms are preferable and methyl group, ethyl group and isopropyl group are particularly preferable.

$R^4$ represents a hydroxyl-protective group. As the hydroxyl-protective group, optionally substituted alkyl groups, optionally substituted aryl groups, optionally substituted aralkyl groups, optionally substituted acyl groups, etc. can be cited.

As the optionally substituted alkyl groups, methoxymethyl group, methoxyethyl group, etc. can be cited.

As the optionally substituted aryl groups, phenyl group, dimethoxyphenyl group, p-methoxyphenyl group, etc. can be cited.

As the optionally substituted aralkyl groups, α-phenylethyl group, benzyl group, trityl group, tolyl group, etc. can be cited.

As the optionally substituted acyl groups, acetyl group, methoxyacetyl group, trifluoroacetyl group, chloroacetyl group, pivaloyl group, formyl group, benzoyl group, p-methoxybenzyl group, p-nitrobenzoyl group, etc. can be cited.

As $R^4$, optionally substituted acyl groups are preferable and p-nitrobenzoyl group is particularly preferable.

$R^5$ and $R^6$ independently represent an alkyl group and methyl group and ethyl group are preferable therefor.

$R^7$ represents a carboxyl-protective group which may be the same as the groups cited above concerning $R^3$.

Y represents an alkoxy group, a halogen atom or a dialkylamino group (wherein the alkyl groups may be either the same or different (still preferably the same) and each has 1 to 6 carbon atoms). Among all, alkoxy groups are preferable. The alkoxy groups may be alkyl groups having 1 to 6 carbon atoms and methoxy group and ethoxy group are preferable therefor.

In the above reaction scheme, a process for producing one of the isomers is exclusively presented. However, the other isomer can be similarly synthesized by using the compound having the oposed configuration to compound (II-a). By using the racemic compound (II), it is also possible to obtain the compound (VI) in the form of a racemate.

Now, each step of the present invention will be illustrated in detail.

Step from Compound (I) to Compound (III)

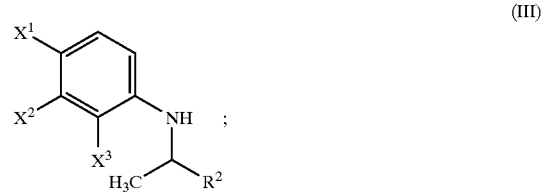

(III)

-continued

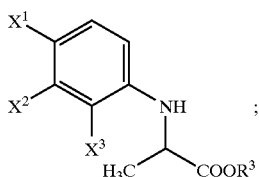
(III-1)

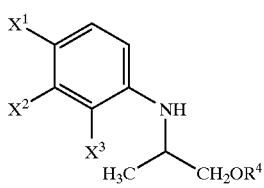
(III-2)

The compound (III) can be obtained by reacting the compound (I) with the compound (II) in the presence of a base. This reaction is carried out usually in a solvent.

The compound (II) occurs as either the compound (II-1) or the compound (II-2) depending on the definition of the substituent $R^2$. In the compound (II), an optically active compound is useful in the production of LVFX. More particularly speaking, one of the isomers, i.e., the compound (II-a) is needed in the production of LVFX. The same applies to the compound (II-1) and the compound (II-2). That is to say, the compound (II-1-a) and the compound (II-2-a) are needed in the production of LVFX. These compounds are represented by the following formulae:

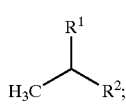
(II)

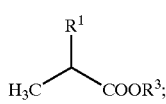
(II-1)

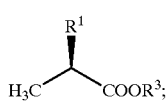
(II-1-a)

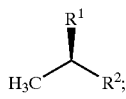
(II-a)

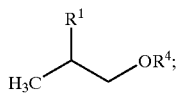
(II-2)

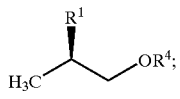
(II-2-a)

The compound (II) can be produced by various methods. It can be obtained by converting a lactic acid ester compound.

For example, the compound (II-1-a) may be obtained by converting the hydroxyl group in a D-lactic acid ester compound into a group capable of leaving. That is to say, the hydroxyl group can be converted into acetoxy group or trifluoroacetoxy group by treating the compound with acetic anhydride or trifluoroacetic anhydride respectively; or into a substituted sulfonyloxy group such as trifluoromethanesulfonyloxy group, methanesulfonyloxy group or p-toluenesulfonyloxy group by reacting the compound respectively with trifluoromethanesulfonyl chloride, methanesulfonyl chloride, p-toluenesulfonyl chloride or trifluoromethanesulfonic anhydride in the presence of a base.

The compound (II-2-a) is obtained by protecting the hydroxyl group of the D-lactic acid ester compound, then reducing the carboxyl ester moiety into hydroxymethyl group, protecting the hydroxyl group thus obtained, eliminating the protective group from the hydroxyl group having been preliminarily protected to thereby restore the hydroxyl group, and then converting it into a leaving group by the same method as described above.

Alternatively, the compound (II-2) can be obtained from 1,2-propanediol. Namely, the terminal hydroxyl group is first protected by using the difference in the reactivity between the primary and secondary hydroxyl groups. Next, the remaining hydroxyl group is converted into a leaving group. In case of using optically active propanediol, the compound (II-2-a) can be obtained.

The compound (III) can be obtained from the compound (I) and the compound (II). The compound (III-a) is obtained by the reaction with the compound (II-a); the compound (III-1) is obtained by the reaction with the compound (II-1); the compound (III-2) is obtained by the reaction with the compound (II-2); the compound (III-1-a) is obtained by the reaction with the compound (II-1-a); and the compound (III-2-a) is obtained by the reaction with the compound (II-2-a).

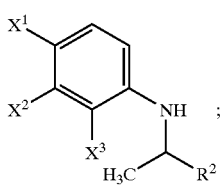
(III)

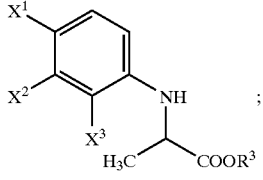
(III-1)

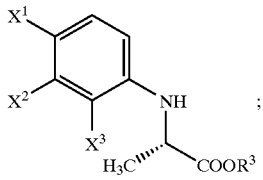
(III-1-a)

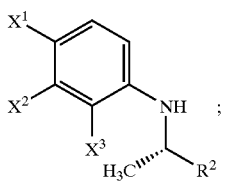
(III-a)

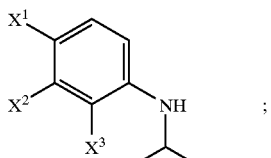
(III-2)

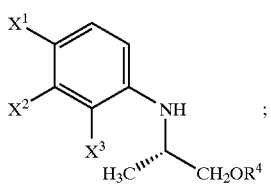
(III-2-a)

The reaction of the compound (I) with the compound (II-1) or the compound (II-2) can be performed under almost the same conditions. Now, these reactions will be described.

The compound (II) may be used in an amount of 1 to 2 times (by mol), preferably from 1.0 to 1.1 time, as much based on the molar number of the compound (I).

As the base, either an inorganic or an organic base may be used. Examples of the inorganic base include alkali metal and alkaline earth metal carbonates and hydrogencarbonates such as sodium carbonate, potassium carbonate, sodium hydrogencarbonate and potassium hydrogencarbonate; and alkali metal and alkaline earth metal halides such as potassium fluoride, cesium fluoride and potassium iodide.

Examples of the organic base include trialkylamines such as triethylamine and ethyldiisopropylamine; N,N-dialkylaniline derivatives having 1 to 4 carbon atoms such as N,N-dimethylaniline and N,N-diethylaniline; and pyridine derivatives optionally substituted by an alkyl group having 1 to 4 carbon atoms such as pyridine and 2,6-lutidine.

In case where $R^1$ is a trifluoromethanesulfonyloxy group, it is preferable to carry out the reaction in the presence of an organic base, still preferably 2,6-lutidine. In case where $R^1$ is a halogen atom, a methanesulfonyloxy group or a p-toluenesulfonyloxy group, it is preferable to carry out the reaction in the presence of an alkali metal or alkaline earth metal carbonate or hydrogencarbonate, still preferably potassium carbonate.

The base may be used in an amount of from 1 to 3 times (by mol), preferably from 1.1 to 2 times, as much based on the molar number of the compound (I).

As the solvent, any solvent which exerts no effect on the reaction may be used. Examples thereof include aromatic hydrocarbon solvents such as toluene and xylene; ether solvents such as diethyl ether, tetrahydrofuran (THF) and 1,4-dioxane; ketone solvents such as acetone and methyl ethyl ketone; amide solvents such as N,N-dimethylformamide (DMF) and N,N-dimethylacetamide (DMAc); halogenated hydrocarbon solvents such as dichloromethane and chloroform; ester solvents such as methyl acetate and ethyl acetate; and alcohol solvents such as methanol, ethanol and isopropanol (IPA).

In case where $R^1$ is a trifluoromethanesulfonyloxy group, it is preferable to use dichloromethane, chloroform, etc. In case where $R^1$ is a halogen atom, a methanesulfonyloxy group or a p-toluenesulfonyloxy group, it is preferable to use N,N-dimethylformamide; N,N-dimethylacetamide, toluene, acetone, dichloromethane, etc.

The solvent may be used in an amount of 5 times or more, preferably from 10 to 15 times, as much based on the compound (I). (Use of 1 ml of a solvent per gram of the compound (I) is referred to as an amount of 1 time).

In case where $R^1$ is a halogen atom, a methanesulfonyloxy group or a p-toluenesulfonyloxy group, the yield can be elevated by using an additive. Examples of the additive include phase transfer catalysts, molecular sieves, etc.

Examples of the phase transfer catalysts include quaternary ammonium salts such as tetra (normal-hexyl) ammonium chloride and tetra(normal-hexyl)ammonium iodide; and crown ethers such as 18-crown-6,15-crown-5.

As the additive, a phase transfer catalyst is preferable. Among all, a lipophilic quaternary ammonium salt is still preferable.

The additive may be used in an amount of from 1 to 100%, preferably from 5 to 30%, based on the molar number of the compound (I).

In case of reacting the compound (II-1), the reaction temperature is not particularly restricted so long as it does not exceed the boiling point of the solvent used. Usually, it ranges from −5° C. to 50° C., preferably from −5° C. to room temperature. In case of reacting the compound (II-2), the reaction temperature usually ranges from −78° C. to 50° C., preferably from −50° C. to 0° C. and still preferably from −50° C. to −30° C.

Although the reaction time depends on the reaction temperature, the reaction is usually completed within about 30 minutes to 5 days.

In case where the product is the compound (III-1), the product can be used as such in the subsequent step without isolating. That is to say, the steps from the compound (I) to the compound (IV) can be continuously performed.

In the step of producing the compound (IV) from the compound (III), it is needed to select a different method depending on the compound (III), i.e., either the compound (III-1) or the compound (III-2).

The compound (III) can be also produced by the following method.

The compound (III-1) can be obtained by reacting a compound (I-0)

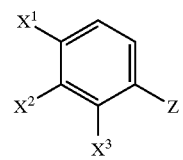
(I-0)

(wherein $X^1$, $X^2$ and $X^3$ each independently represents a halogen atom; and Z represents an amino group or a nitro group); with pyruvic acid (the acid or an ester):

(wherein R3 represents a hydrogen atom or an alkyl group); in a solvent in the presence of a metal catalyst under a hydrogen gas atmosphere.

The metal catalyst to be used in this production process is not particularly restricted, so long as it is usable in a catalytic hydrogenation reaction. Among such catalysts, palladium-carbon, Raney nickel and Raney cobalt are preferable.

In this reaction, a dehydrating agent may be added to promote the reaction. The dehydrating agent is not particularly restricted, so long as it exerts no effect on the reaction. For example, use may be made of anhydrous magnesium sulfate, anhydrous sodium sulfate, a molecular sieve, etc. Among these dehydrating agents, anhydrous magnesium sulfate and anhydrous sodium sulfate are preferable.

The reaction between the compound (I-0) and pyruvic acid can be more conveniently performed by adding a catalytic amount of an acid and carrying out the hydrogenation reaction under elevated pressure. The acid to be added may be either anorganic acid or an inorganic acid. Examples thereof include inorganic acids such as hydrochloric acid, nitric acid, sulfuric acid and phosphoric acid; and organic acids such as substituted carboxylic acid compounds and substituted sulfonic acid compounds. Examples of the substituted carboxylic acids include acetic acid, trifluoroacetic acid and fumaric acid. Examples of the substituted sulfinic acid include methanesulfonic acid, trifluoromethanesulfonic acid, benzenesulfonic acid and toluenesulfonic acid. As the inorganic acid to be added, hydrochloric acid and sulfuric acid are preferable.

As the acid to be added, such an acid as described above may be added. Alternatively, it is also possible to select pyruvic acid per se ($CH_3COCOOH$) as the pyruvic acid derivative used as the reactant, thereby making the pyruvic acid to serve both as the reactant and the acid for promoting the reaction.

The acid may be added in a catalytic amount. In case of using an acid other than pyruvic acid, it may be added in an amount of from 1 to 30% (by mol) based on the molar number of the compound (I-0). In case of using pyruvic acid per se as a reaction promoter, it may be added in an equimolar amount to the molar number of the compound (I-0). However, an effect of promoting the reaction can be achieved by further adding it in small excess. To achieve the catalytic effect, pyruvic acid may be added in an amount of from about 1 to 5% by mol.

As the solvent, any solvent which exerts no effect on the reaction may be used without restriction. Examples thereof include alcohol solvents such as methanol, ethanol, propanol and isopropanol; ether solvents such as diethyl ether, tetrahydrofuran and 1,4-dioxane; halogenated hydrocarbon solvents such as dichloro methane and chloroform; amide solvents such as N,N-dimethylformamide and N,N-dimethylacetamide; dimethylsulfoxide, acetonitrile, acetone, acetic acid esters, water, etc. It is also possible to use mixtures of these solvents.

Among these solvents, alcohol solvents are preferable and methanol, ethanol and isopropanol are still preferable.

Although the reaction temperature varies depending on the solvent used, it usually ranges from −78° C. to the boiling point of the solvent, preferably from room temperature to the boiling point of the solvent.

The reaction time ranges from 1 to 24 hours. Usually, the reaction is completed within 1 to 16 hours.

This process is carried out under a hydrogen gas atmosphere. The hydrogen gas pressure may usually range form 0.1 to 10 MPa, preferably from 0.1 to 5 Mpa.

In case where this reaction is performed by using a nitrobenzene derivative ($Z=NO_2$), the nitro group is first reduced into an amino group (an aniline derivative). Then this amino group reacts with the carbonyl group in pyruvic acid to give an imine compound:

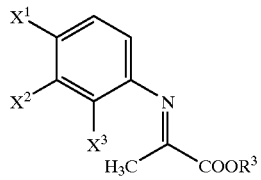

Next, the imino group in this imine compound is hydrogenated into an amino group. (One of the geometric isomers of the imine compound is exclusively presented herein.) It is therefore needless to say that an aniline compound having a reduced nitro group is usable as the starting material in this reaction. This imine compound is obtained either as one of the geometric isomers or as a mixture of the isomers. Either case is applicable to the asymmetric reduction.

By the production process of reacting the compound (I-0) with a pyruvic acid compound under reductive conditions, the compound (III-1) is usually obtained as a racemate. To obtain the optically active compound (III-1-a), the imine compound formed by the reaction of the compound (I-0) with the pyruvic acid compound is reduced under asymmetrically reductive conditions.

The asymmetric reduction reaction of the imine can be achieved by using the following reaction conditions:

(1) reduction reactions using boron and an aluminum compound reported in K. Yamada, J. Chem. Soc., Perkin Trans. 1, 265 (1983); S. Ituno, Bull. Chem. Soc. Jpn., 60, 395(1987); S. Ituno, J. Chem. Soc., Perkin Trans. 1, 1859 (1990); B. T. Cho, Tetrahedron Asymmetry, 3, 1583 (1992); T. Sakai, Synlett., 753 (1995); M. Shimizu, Tetrahedron Lett., 36, 8607 (1995); C. Bolm, Synlett., 655 (1994); J. M. Brunel, Synlett., 177 (1996); R. O. Hutchins, J. Org. Chem., 52, 704 (1987), etc.;

(2) hydrosilylation reactions reported in N. Langlois, Tetrahedron Lett., 4865 (1973); H. B. Kagan, J. Organomet. Chem., 90, 353 (1975); X. Verdaguer, J. Am. Chem. Soc., 118, 6784 (1996), etc.;

(3) catalytic hydrogenation reactions reported in the following documents and the like (Rh catalyst: A. Levi, J. Chem. Soc., Chem. Commun., 6 (1975); S. Vastag, J. Mol. Catal., 22, 283 (1984); G.-K. Kang, J. Chem. Soc., Chem. Commun., 1466 (1988); W. R. Cullen, J. Mol. Catal., 62, 243 (1990); A. G. Becalski, Inorg. Chem., 30, 5002 (1991); J. Bakos, J. Organomet. Chem., 279, 23 (1985); J. Bakos, J. Organomet. Chem., 370, 263 (1989); J. Bakos, J. Chem. Soc., Chem. Commun., 1684 (1991); C. Lensink, Tetrahedron Asymmetry, 3, 235(1992); C. Lensink, Tetrahedron Asymmetry, 4, 215 (1993); J. M. Buriak, Organometallics, 15, 3161 (1996); M. J. Murk, J. Am. Chem. Soc., 114, 6266 (1992); M. J. Burk, Tetrahedron, 50, 4399 (1994); Ir catalyst: F. Spindler, Angew. Chem., Int. Ed. Engl., 29, 558 (1990); A. Togni., Angew. Chem., Int. Ed. Engl., 35, 1475 (1996); T. Morimoto, Chem. Pharm. Bull., 42, 1951 (1994); T. Morimoto, Tetrahedron Asymmetry, 6, 2661 (1995); T. Morimoro, Synlett., 748 (1995); K. Tani, Chem. Lett., 955 (1995); K. Satoh, Tetrahedron Asymmetry, 9, 2657 (1998); Y. Ng C. Chan, J. Chem. Soc., Chem. Commun., 869 (1990); Y. Ng C. Chan, J. Am. Chem. Soc., 112, 9400 (1990); R. Sablong, Tetrahedron. Lett., 37, 4937 (1996); Ti catalyst: C. A. Willoughby, J. Am. Chem. Soc., 114, 7562 (1992); C. A. Willoughby, J. Org. Chem., 58, 7627 (1993); C. A. Willoughby, J. Am. Chem. Soc., 116, 8952 (1994); C. A. Willoughby, J. Am. Chem. Soc., 116, 11703 (1994); Ru catalyst: C. Botteghi, Chimia, 29, 256 (1975); W. Oppolzer, Tetrahedron Lett., 31, 4117 (1990); D. E. Fogg, Inorg. Chim. Acta., 222, 85 (1984); and (4) hydrogen-transfer reduction reactions reported in S. Hashiguchi, J. Am. Chem., Soc., 117, 7562 (1995); A. Fujii, J. Am. Chem. Soc., 118, 2521 (1996); N. Uematsu, J. Am. Chem. Soc., 118, 4916 (1996), etc.

In the optically active compounds (III-1-a), a carboxylic acid compound (see the following structural formula):

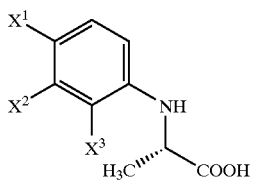

can be obtained by treating an ester compound of the corresponding compound with an enzyme capable of asymmetrically hydrolyzing an ester or a liquid culture medium of a microorganism, cells of this microorganism or processed cells of this microorganism.

To accomplish asymmetrically hydrolyzing of the ester, the ester compound (racemate) of the compound (III-1) is suspended in an appropriate buffer and then an enzyme capable of asymmetrically hydrolyzing an ester or a liquid culture medium of a microorganism, cells of this microorganism or processed cells of this microorganism are added followed by stirring. The enzyme, etc. usable in this reaction is not particularly restricted, so long as it is capable of asymmetrically hydrolyzing an ester. Examples of the enzyme include marketed enzyme preparations originating in microorganisms, animals and plants. For example, use can be made of various esterases, proteases or chymotrypsins. As the microorganism, use can be made of bacteria belonging to the genera *Bacillus, Micrococcus* and *Actinomyces*; fungi belonging to the genera *Aspergillus, Rhizopus, Nannizia* and *Penicillium*; and yeasts belonging to the genera *Candida, Saccharomyces* and *Zygoascus*.

By the treatment with the above-described enzyme, microbial cells, etc., the ester moiety of one of the isomers (enantiomers) of the compound (III-1) is hydrolyzed to give a carboxylic acid. Further, this product is converted into a carboxylic acid salt and thus dissolved in the treatment liquor. At this point, the treatment liquor is extracted with an organic solvent such as ethyl acetate, chloroform, diisoproyl ether (IPE) or methyl t-butyl ether. Thus, an ester compound (see the following structural formula) which is the unnecessary isomer (enantiomer) of the compound (III-1-b):

(III-1-b)

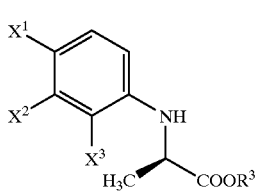

can be isolated and collected.

Prior to the extraction of the compound (III-1-b), it is favorable to eliminate the enzyme, microbial cells, etc. by, for example, filtration. After extracting the compound (III-1-b), the treatment liquor is acidified and then extracted with an organic solvent such as diisopropyl ether, methyl t-butyl ether or ethyl acetate. Thus, a carboxylic compound of the compound (III-1-a) which is a free compound can be obtained.

The treatment with the enzyme, microbial cells, etc. may be carried out usually at a temperature of from 5° C. to 60° C., preferably from 20° C. to 40° C.

The pH value of this treatment liquor may range from 4 to 9, preferably from 6 to 8.

The treatment with the enzyme, microbial cells, etc. may be carried out for from 4 hours to 7 days, preferably from 8 hours to 50 hours.

The concentration of the compound (III-1) in the treatment liquor usually ranges from 0.1% to 20% on the weight basis, preferably from 0.5% to 5%.

The amount of the enzyme or the liquid culture medium of a microorganism, cells of this microorganism or processed cells of this microorganism is not particularly restricted. In general, it is preferably used in an amount of from 0.05 to 0.5 times by weight as much as the compound (III-1) on the dry weight basis.

It is also possible to obtain a carboxylic acid compound of the compound (III-1-b) by using an enzyme or the liquid culture medium of a microorganism having the reverse asymmetric recognition ability to the cleavage of the ester of the compound (III-1-a) and conversion into a carboxyl group, cells of this microorganism or processed cells of this microorganism.

A carboxylic acid compound of the racemic compound (III-1) can be obtained by separating the isomers (enantiomers) by forming diastereomeric salts with an optically active organic base and crystallizing them. By further recrystallizing the thus obtained salt by using an appropriate solvent, a salt having a higher stereoisomeric purity can be obtained.

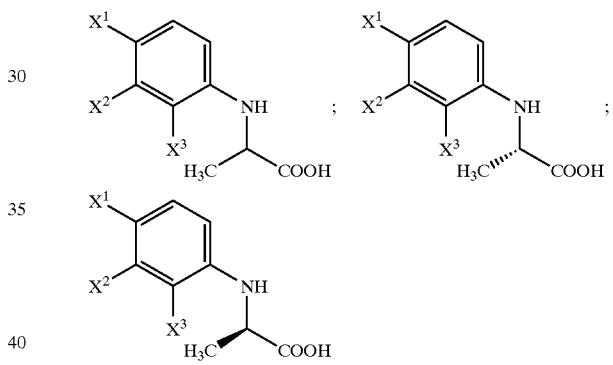

By treating the thus formed diastereomeric salts with an acid, the carboxylic compounds of the compound (III-1-a) and the compound (III-1-b) can be separated.

The term "comprises a single (optical) isomer" as used herein means not only a case in which it is completely free from the other (optical) isomer but also a case in which the other isomer may be present in such a degree that it does not exert influences upon physical constants.

The term "stereoisomerically pure salt" as used herein has the following meaning. In case where an acid and a base constituting a salt have stereoisomers, namely, a salt formed by an acid comprised of a single stereoisomer and a base similarly comprised of a single stereoisomer is referred to a stereoisomerically pure salt. That is to say, it means a salt wherein the constituting acid and base are each comprised of a single stereoisomer. The term "comprises a single stereoisomer" as used herein may be considered as the state of substantially being free from other isomer.

Examples of the optically active organic base which can be used in forming such salts involve optically active ethylamine derivatives aryl-substituted at the 1-position (1-arylethylamine derivatives) represented by the following formula:

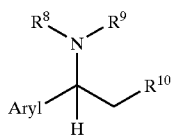

(wherein Aryl represents an aryl group optionally having a halogen atom, a nitro group, a cyano group, a carbamoyl group, an alkyl group having 1 to 6 carbon atoms or an alkoxy group having 1 to 6 carbon atoms; and $R^8$, $R^9$ and R10 each independently represents:
(1) a phenyl group optionally having a halogen atom, an alkyl group having 1 to 6 carbon atoms, a halogenoalkyl group having 1 to 6 carbon atoms, an alkoxy group having 1 to 6 carbon atoms, a nitro group, a carbamoyl group or a cyano group;
(2) a benzyl group optionally having a halogen atom, an alkyl group having 1 to 6 carbon atoms, a halogenoalkyl group having 1 to 6 carbon atoms, an alkoxy group having 1 to 6 carbon atoms, a nitro group, a carbamoyl group or a cyano group;
(3) an alkyl group having 1 to 6 carbon atoms; or
(4) a hydrogen atom).

Examples of the aryl group include phenyl group and naphthyl group. The aromatic rings of these aryl groups may have one or more substituents such as halogen atoms, nitro group, cyano group, carbamoyl group, alkyl groups having 1 to 6 carbon atoms and alkoxy groups having 1 to 6 carbon atoms, or one or more types of these substituents.

As examples of these optically active bases, 1-phenylethylamine, 1-(p-tolyl)ethylamine and 1-phenyl-2-(p-tolyl)ethylamine may be cited.

Among these bases, examples of optically active bases capable of advantageously forming a salt in combination with the carboxylic acid compound of the compounds (III-1-a) include (R)-(+)-1-phenylethylamine, (R)-(+)-1-(p-tolyl)ethylamine and (S)-(+)-1-phenyl-2-(p-tolyl)ethylamine.

Examples of optically active bases capable of advantageously forming a salt in combination with the carboxylic acid compound of the compounds (III-1-b) include (S)-(+)-1-phenylethylamine, (S)-(+)-1-(p-tolyl)ethylamine and (R)-(+)-1-phenyl-2-(p-tolyl)ethylamine.

On the other hand, the aromatic rings of the 1-arylethylamine derivatives are not restricted to hydrocarbyl aromatic rings but involve aromatic heterocycles containing sulfur atom, nitrogen atom, oxygen atom and the like. Examples thereof include thiophene, benzothiophene, pyridine, quinoline, isoquinoline, furan, benzofuran, etc.

The optically active base may be used usually in an equimolar amount or less to the molar number of the carboxylic acid compound.

As the solvent for crystallizing or recrystallizing the target salt, various solvents may be used. Examples of solvents usable herein include aliphatic or aromatic hydrocarbon solvents such as n-hexane, n-pentane, benzene, toluene and xylene; alcohol solvents such as methanol, ethanol, propanol, isopropanol, n-butanol and t-butanol; ether solvents such as diethyl ether, diisopropyl ether, methyl t-butyl ether, tetrahydrofuran, 1,2-dimethoxyethane and 1,4-dioxane; amide solvents such as N,N-dimethylformamide and N,N-dimethylacetamide; and halogenated hydrocarbon solvents such as chloroform, methylene chloride and 1,2-dichloroethane (EDC). In addition, use can be also made of water, acetonitrile, acetic acid esters, acetone, etc. Either one of these solvents or a mixture of several types thereof may be used.

The solvent may be usually used in an amount of from 1 to 100 times by weight, preferably from about 2 to 50 times by weight.

Although the temperature for the crystallization or recrystallization of the desired salt is not definite, temperature conditions usually used may be selected. More particularly speaking, it may be performed within a temperature range from ice-cooling to the boiling point of the solvent used.

The reaction time usually ranges from 1 to 24 hours.

The carboxylic acid salt may be converted into the free carboxylic acid by treating with an acid. Namely, the carboxylic acid salt is treated with an inorganic acid such as hydrochloric acid or sulfuric acid followed by isolation by, for example, extraction with an organic solvent.

Since the isomer (enantiomer) to be used in the production of levofloxacin is the compound (III-1-a), the other compound (III-1-b) has no utility value as such. An ester compound of this compound (III-1-b) can be racemized by treating in the presence of a base. Thus, the unnecessary isomer can be converted into the necessary isomer by this method.

As the solvent usable in this isomerization reaction, various solvents can be cited. Examples thereof include aliphatic or aromatic hydrocarbon solvents such as n-hexane, n-pentane, benzene, toluene and xylene; alcohol solvents such as methanol, ethanol, propanol, isopropanol, n-butanol and t-butanol; ether solvents such as diethyl ether, diisopropyl ether, methyl t-butyl ether, tetrahydrofuran, 1,2-dimethoxyethane and 1,4-dioxane; amide solvents such as N,N-dimethylformamide and N,N-dimethylacetamide; and halogenated hydrocarbon solvents such as chloroform, methylene chloride and 1,2-dichloroethane. In addition, use can be also made of water, acetonitrile, acetic acid esters, acetone, etc. Either one of these solvents or a mixture of several types thereof may be used.

Among these solvents, aromatic hydrocarbons such as toluene and amides such as N,N-dimethylformamide and N,N-dimethylacetamide are preferable.

Although the reaction temperature varies depending on the solvent used, it usually ranges from −78° C. to the boiling point of the solvent, preferably from room temperature to the boiling point of the solvent.

The reaction time ranges from 1 to 24 hours, preferably from 1 to 16 hours.

The base may be either an organic base or an inorganic base. For example, use can be made of hydroxides, carbonates, hydrogencarbonates and alkoxides of alkali metals and alkaline earth metals such as sodium, potassium, lithium, magnesium and calcium; metal hydrides such as sodium hydride, potassium hydride and lithium hydride; alkyl lithium reagents such as n-butyl lithium, methyl lithium and lithium diisopropylamide; tertiary amines such as triethylamine and N,N-diisopropylethylamine; nitrogen-containing heterocyclic compounds such as 1,8-diazabicyclo[5.4.0]undec-7-ene (DBU), 1,8-diazabicyclo[4.3.0]non-5-ene (DBN) and N-methylmorpholine; N,N-dialkylanilines such as dimethylaniline and diethylaniline; etc.

Among these bases, it is preferable to use nitrogen-containing heterocyclic compounds such as 1,8-diazabicyclo[5.4.0]undec-7-ene (DBU); alkali metal or alkaline earth metal carbonates such as potassium carbonate; or alkali metal or alkaline earth metal metal alkoxides such as potassium tertiary-butoxide (t-BuOK).

The base may be used in an amount of from 0.1 to 15 times by mol, preferably from 1 to 5 times, as much based on the molar number of the ester compound of the compound (III-1-b).

To promote the reaction, the reaction may be carried out in the presence of a quaternary ammonium salt such as tetrabutylammonium bromide or benzyltriethylammonium chloride; an alkali metal or alkaline earth metal iodide such as potassium iodide or sodium iodide; a crown ether, etc.

The compound (III-1-b) can be converted into a carboxylic acid compound of the compound (II-1) by racemizing by treating with a base and then hydrolyzing it.

As the solvent, use can be made of various solvents, for example, aliphatic or aromatic hydrocarbon solvents such as n-hexane, n-pentane, benzene, toluene and xylene; alcohol solvents such as methanol, ethanol, propanol, isopropanol, n-butanol and t-butanol; ether solvents such as diethyl ether, diisopropyl ether, methyl t-butyl ether, tetrahydrofuran, 1,2-dimethoxyethane and 1,4-dioxane; amide solvents such as N,N-dimethylformamide and N,N-dimethylacetamide; and halogenated hydrocarbon solvents such as chloroform, methylene chloride and 1,2-dichloroethane. In addition, use can be also made of water, acetonitrile, acetic acid esters, acetone, etc. Either one of these solvents or a mixture of several types thereof may be used.

Among these solvent, aromatic hydrocarbon solvents such as toluene and N,N-dimethylformamide and N,N-dimethylacetamide are preferable.

Although the reaction temperature varies depending on the solvent used, it usually ranges from −78° C. to the boiling point of the solvent, preferably from room temperature to the boiling point of the solvent.

The reaction time ranges from 1 to 24 hours. Usually, the reaction is completed within 1 to 16 hours.

The base may be either an organic base or an inorganic base. For example, use can be made of hydroxides, carbonates, hydrogencarbonates and alkoxides of alkali metals and alkaline earth metals such as sodium, potassium, lithium, magnesium and calcium; metal hydrides such as sodium hydride, potassium hydride and lithium hydride; alkyl lithium reagents such as n-butyl lithium, methyl lithium and lithium diisopropylamide; tertiary amines such as triethylamine and N,N-diisopropylethylamine; nitrogen-containing heterocyclic compounds such as 1,8-diazabicyclo[5.4.0]undec-7-ene (DBU), 1,8-diazabicyclo[4.3.0]non-5-ene (DBN) and N-methylmorpholine; N,N-dialkylanilines such as dimethylaniline and diethylaniline; etc.

Among these bases, it is preferable to use alkali metal alkoxides such as potassium tertiary-butoxide or alkali metal or alkaline earth metal carbonates such as potassium carbonate.

The base may be used in an amount of from 0.1 to 15 times by mol, preferably from 1 to 5 times, as much based on the molar number of the ester compound of the compound (III-1-b).

To promote the reaction, the reaction may be carried out in the presence of a quaternary ammonium salt such as tetrabutylammonium bromide or benzyltriethylammonium chloride; an alkali metal or alkaline earth metal iodide such as potassium iodide or sodium iodide; a crown ether, etc.

The ester is hydrolyzed by using an acid or a base. In the acidic hydrolysis, use is made of an acid such as hydrochloric acid or sulfuric acid. In the basic hydrolysis, use is made of a base, for example, an alkali metal hydroxide such as sodium hydroxide or potassium hydroxide; an alkali metal carbonate such as sodium carbonate or potassium carbonate; or an alkali metal hydrogencarbonate such as sodium hydrogencarbonate or potassium hydrogencarbonate. The base is usually used in the form of an aqueous solution.

The carboxylic acid compound in the compound (III-a), which is obtained by the hydrolysis with the use of the enzyme, the liquid culture medium of the microorganism, the microbial cells or the processed microbial cells or the hydrolysis under acidic or basic conditions, can be converted into an ester compound in a conventional manner. Namely, it may be reacted with the following alcohol in the presence of an acid catalyst:

$R^7$—OH.

Examples of the alcohol usable herein include methanol, ethanol, propanol, isopropanol and n-butanol. By using such an alcohol, esterification toward an ester corresponding to the alcohol proceeds. Although the reaction temperature varies depending on the alcohol used, it usually ranges from −78° C. to the boiling point of the alcohol, preferably from room temperature to the boiling point of the alcohol. Examples of the acid usable herein include hydrochloric acid, sulfuric acid and phosphoric acid. As another esterification method, use can be also made of the esterification by preparing an acid chloride followed by the treatment with an alcohol.

The carboxylic acid compound among the compounds (III-a) obtained by the asymmetric hydrolysis of the ester or the hydrolysis of the ester in the presence of an acid or a base can be purified by forming salts with various amines. As the amine usable in this purification, it is preferable to select a highly lipophilic amine and examples thereof include cyclic alkylamines such as cyclohexylamine; and aralkylamines such as benzylamine and phenethylamine. Among these amines, cyclohexylamine and benzylamine are preferable and cyclohexylamine is still preferable. A salt of such an amine can be purified by recrystallization in a conventional manner. As the conditions for the purification, the conditions for the optical resolution as described above can be appropriately used. The amine salt of the carboxylic acid compound among the compounds (III-1) thus obtained can be converted into a free compound by treating with an acid. Subsequently, it can be esterified by the above-described method. It is also possible to carry out the esterification while omitting the procedure for obtaining the free compound by using an acid for the esterification in excess based on the molar number of the carboxylic acid salt.

Step from Compound (III-1) to Compound (IV)

The compound (IV) can be obtained by reducing the compound (III-1). This reaction may be carried out by treating the compound (III-1) in a solvent in the presence of a reducing agent. As the compound (III-1) to be used in this reduction, one wherein the $COOR^3$ moiety is an ester is particularly preferable.

Examples of the reducing agent include borohydride reducing agents such as sodium borohydride, lithiumborohydride, calcium borohydride, zinc borohydride, magnesium borohydride and sodium cyano borohydride cyanide; and aluminum hydride reducing agents such as lithium aluminum hydride. As the reducing agent, borohydride reducing agents are preferable and sodium borohydride is particularly preferable.

The reducing agent may be used in an amount from 1.1 to 2.5 times by mol, preferably from 1.1 to 1.5 time, as much based on the molar number of the compound (III-1).

The solvent usable herein is not particularly restricted so long as it exerts no effect on the reaction. Examples thereof include alcohol solvents such as methanol, ethanol, isopropanol and t-butanol; ether solvents such as diethyl ether and tetrahydrofuran; etc. As the solvent, alcohol solvents are preferable and isopropanol is still preferable. In case of using isopropanol, the reaction can be promoted by adding methanol in an amount from 0.5 to 5 times by mol, preferably from 0.5 to 2 times, as much based on the molar number of the compound (III-1).

The reaction temperature may be a temperature exerting no undesirable effect on the reaction. It preferably ranges from 0 to 60° C., still preferably from room temperature to 50° C. The reaction time may range from 1 hour to 20 hours.

As the results of the inventors' examination on this reduction reaction, it is found out that, in case where an optically active compound among the compounds of the formula (III-1) is subjected to the reduction reaction, it is favorable to select a non-alcohol solvent (an aprotic solvent) as the solvent and use a metal hydride compound as the reducing agent for the reaction. Namely, it is clarified that in case where the reaction of reducing an optically active compound in this process is performed in a protic solvent, the steric structure is partly inverted and thus the optical purity is lowered.

As the metal hydride compound, use can be made of a metal borohydride compound or a metal aluminum hydride compound. Particular examples thereof include metal borohydride compounds such as sodium borohydride, lithium borohydride, calcium borohydride, potassium borohydride, zinc borohydride, magnesium borohydride and sodium cyano borohydride cyanide; and metal aluminum hydride compounds such as lithium aluminum hydride. Among these compounds, metal borohydride compounds are preferable and sodium borohydride is particularly preferable.

The reducing amount may be used in an amount from 1 to 5 times by mol, preferably from about 1.1 to 2 times, as much based on the molar number of the compound (III-1-a) or (III-1-b).

It this step, it is particularly preferable to use an aprotic solvent. Examples of the aprotic solvent usable herein include linear and branched aliphatic hydrocarbon solvents such as n-hexane, n-pentane, cyclohexane and cyclopentane; aromatic hydrocarbon solvents such as benzene, toluene and xylene; ether solvents such as diethyl ether, diisopropyl ether, methyl t-butyl ether, tetrahydrofuran, 1,2-dimethoxyethane and 1,4-dioxane; and halogenated hydrocarbon solvents such as chloroform, methylene chloride and 1,2-dichloroethane. In addition, use can be also made of acetic acid esters, etc. Either one of these solvents or a mixture of several types thereof may be used.

Among these solvents, aliphatic hydrocarbon solvents such as n-hexane and cyclohexane, ether solvents such as diisopropyl ether and methyl t-butyl ether, and aromatic hydrocarbon solvents such as toluene are preferable.

As the alcohol added herein, primary alcohols are preferable and methanol is particularly preferable. The alcohol may be used in an amount of from 3 to 20 times, preferably from about 4 to 15 times, as much based on the compound (III-1-a) or (III-1-b).

Although the reaction temperature varies depending on the solvent used, it usually ranges from −78° C. to the boiling point of the solvent, preferably from 10° C. to the boiling point of the solvent.

The reaction time ranges from 1 to 24 hours. Usually, the reaction is completed within about 2 to 16 hours.

To perform the reduction reaction in this step without isomerizing the optically active compound, it is preferable that the compound (III-1-a) or (III-1-b) and the reducing agent are added to the aprotic solvent and then the alcohol is added thereto (under stirring).

Step from Compound (III-2) to Compound (IV)

The compound (IV) can be obtained by deprotecting the compound (III-2).

Although the deprotection procedure varies depending on the type of $R^4$ used as the hydroxyl-protective group, it may be carried out by an appropriate method for the type of $R^4$ ordinarily used in the art. In case where $R^4$ is an aralkyl group (arylmethyl) or an aralkyloxycabronyl group, a catalytic hydrogenation reaction may be used. In case where $R^4$ is an acyl group, a hydrolysis reaction with an acid or an alkali may be used. In case where $R^4$ is an alkoxycabronyl group or an ether, decomposition with an acid or treatment with zinc in acetic acid, etc. may be used.

Step from Compound (IV) to Compound (V)

In this step, the compound (V) can be obtained by adding to the compound (IV) a methylenemalonic acid dialkyl ester derivative represented by the following formula:

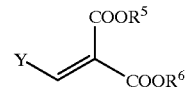

(wherein $R^5$ and $R^6$, each independently represents an alkyl group; and Y represents an alkoxy group, a halogen atom or a dialkylamino group);

followed by heating, or treating the compound (IV) and the methylenemalonic acid dialkyl ester derivative in a solvent in the presence of a base and a phase transfer catalyst.

(1) Method of Adding Methylenemalonic Acid Dialkyl Ester Derivative to Compound (IV)

The methylenemalonic acid dialkyl ester derivative may be used in an amount from 1 to 3 times by mol, preferably from 1.05 to 1.2 time, as much based on the molar number of the compound (IV).

The reaction can be performed either without using a solvent or in a solvent. As the solvent, use can be made of any one so long as it exerts no effect on the reaction. Examples thereof include aromatic hydrocarbon solvents such as toluene and xylene.

It is preferable to perform the reaction without using a solvent or using an aromatic hydrocarbon solvent such as toluene or xylene.

The reaction temperature is not particularly restricted so long as it does not exceed the boiling point of the solvent. It preferably ranges from 100° C. to the boiling point of the solvent. Although the reaction time varies depending on the reaction temperature, it is usually completed within 1 hour to 1 day.

(2) Method of Treating Compound (IV) and Methylenemalonic Acid Dialkyl Ester Derivative in Solvent in the Presence of Base and Phase Transfer Catalyst The methylenemalonic acid dialkyl ester derivative may be used in an amount from 1 to 3 times by mol, preferably from 1.05 to 2 times, as much based on the molar number of the compound (IV).

The solvent is not particularly restricted so long as it exerts no undesirable effect on the reaction. Examples thereof include aliphatic hydrocarbon solvents such as n-hexane, and n-pentane; aromatic hydrocarbon solvents such as benzene, toluene and xylene; ether solvents such as diethyl ether, diisopropyl ether, methyl t-butyl ether, tetrahydrofuran and 1,4-dioxane; ketone solvents such as acetone and methyl ethyl ketone; amide solvents such as N,N-dimethylformamide and N,N-dimethylacetamide; halogenated hydrocarbon solvents such as dichloromethane and chloroform; ester solvents such as methyl acetate and ethyl acetate; alcohol solvents such as methanol, ethanol, isopropanol, n-butanol and t-butanol; and halogenated hydrocarbons such as chloroform, methylene chloride and 1,2-dichloroethane. Among these solvents, aromatic hydrocarbon solvents, amide solvents, ketone solvents and halogenated solvents are preferable and toluene, N,N- dimethylformamide, N,N-diemthylacetamide, acetone and dichloromethane are still preferable. Among these solvents, amide solvents such as N,N-dimethylformamide and N,N-dimethylacetamide are further preferable.

The base may be either an inorganic base or an organic base. Examples of the inorganic bases include alkali metal hydrides such as sodium hydride and lithium hydride; alkaline earth metal hydrides such as calcium hydride; alkali metal hydroxides such as sodium hydroxide and potassium hydroxide; alkali metal or alkaline earth metal carbonates or hydrogencarbonates such as sodium carbonate, potassium carbonate, sodium hydrogencarbonate and potassium hydrogencarbonate; and alkali metal or alkaline earth metal halides such as potassium fluoride, cesium fluoride and potassium iodide.

Examples of the organic bases include alkali metal alkoxides such as sodium methoxide, lithium methoxide, sodium ethoxide, lithium ethoxide, sodium tertiary-butoxide and potassium tertiary-butoxide; trialkylamines such as triethylamine and ethyldiisopropylamine; aniline derivatives carrying alkyl groups having from 1 to 4 carbon atoms such as N,N-dimethylaniline and N,N-diethylaniline; pyridine derivatives optionally substituted by alkyl groups having from 1 to 4 carbon atoms such as pyridine and 2,6-lutidine; and nitrogen-containing heterocyclic compounds such as 1,8-diazabicyclo[5.4.0]undec-7-ene.

Among these bases, it is preferable to use alkali metal alkoxides, nitrogen-containing heterocyclic compounds and alkali metal or alkaline earth metal hydroxides. Potassium tertiary-butoxide, 1,8-diazabicyclo[5.4.0]undec-7-ene and alkali hydroxides are still preferable and potassium hydroxide is further preferable. Alkali hydroxides, in particular, potassium hydroxide can be adequately used, since no isomerization proceeds during the reaction in such a case.

The base may be used in an amount of from 1 to 15 times by mol, preferably from 1 to 3 times, as much based on the molar number of the ester compound of the compound (IV).

In this reaction, the yield can be elevated by adding an additive. Examples of the additive include phase transfer catalysts and molecular sieves.

Examples of the phase transfer catalysts include quaternary ammonium salts such as tetra (normal-hexyl) ammonium chloride, trimethylbenzylammonium chloride, triethylbenzylammonium chloride, trimethylphenylammonium chloride and tetrabutylammonium hydrogensulfate; and crown ethers such as 18-crown-6,15-crown-5.

As the additive, a phase transfer catalyst is preferable. Among all, a lipophilic quaternary ammonium salt is still preferable.

Among these phase transfer catalysts, quaternary ammonium salts such as tetra (normal-hexyl) ammonium chloride, trimethylbenzylammonium chloride, triethylbenzylammonium chloride, trimethylphenylammonium chloride and tetrabutylammonium hydrogensulfate are preferable.

The phase transfer catalyst may be used in an amount of from 1% to 100%, still preferably from about 3% to 30%, based on the molar number of the compound (II).

Although the reaction temperature varies depending on the solvent used, it usually ranges from −78° C. to the boiling point of the solvent, preferably from room temperature to 60° C. and still preferably around room temperature.

The reaction time ranges from 1 to 24 hours. Usually, the reaction is completed within about 1 to 12 hours.

The compound (V) which is the obtained product can be used as such in the subsequent step without isolation. Namely, the steps from the compound (IV) to the compound (VI) can be continuously carried out.

Step from Compound (V) to Compound (VI)

The compound represented by the formula (VI) can be obtained by the intramolecular cyclization of the compound represented by the formula (V). This step may be carried out by treating in a solvent in the presence of a base and a phase transfer catalyst.

The base may be either an organic base or an inorganic base. Examples of the inorganic bases include alkali metal hydrides such as sodium hydride and lithium hydride; alkaline earth metal hydrides such as calcium hydride; alkali metal hydroxides such as sodium hydroxide and potassium hydroxide; alkali metal or alkaline earth metal carbonates or hydrogencarbonates such as sodium carbonate, potassium carbonate, sodium hydrogencarbonate and potassium hydrogencarbonate; and alkali metal or alkaline earth metal halides such as potassium fluoride, cesium fluoride and potassium iodide.

Examples of the organic bases include alkali metal alkoxides such as sodium methoxide, lithium methoxide, sodium ethoxide, lithium ethoxide, sodium tertiary-butoxide and potassium tertiary-butoxide; trialkylamines such as triethylamine and ethyldiisopropylamine; N,N-dialkylaniline derivatives carrying alkyl groups having from 1 to 4 carbon atoms such as N,N-dimethylaniline and N,N-diethylaniline; pyridine derivatives optionally substituted by alkyl groups having from 1 to 4 carbon atoms such as pyridine and 2,6-lutidine; and nitrogen-containing heterocyclic compounds such as 1,8-diazabicyclo[5.4.0]undec-7-ene.

As the base, it is preferable to use alkali metal or alkaline earth metal hydroxides or alkyl metal alkoxides. Potassium hydroxide and potassium tertiary-butoxide are still preferable and potassium hydroxide is further preferable.

The base may be used in an amount of from 0.1 to 15 times by mol, preferably from 1 to 3 times, as much based on the molar number of the ester compound of the compound (V).

The reaction in this step can be promoted by carrying out in the presence of a phase transfer catalyst.

Examples of the phase transfer catalyst include quaternary ammonium salts such as tetra (normal-hexyl) ammonium chloride, trimethylbenzylammonium chloride, triethylbenzylammonium chloride, trimethylphenylammonium chloride and tetrabutylammonium hydrogensulfate; and crown ethers such as 18-crown-6,15-crown-5.

Among these phase transfer catalysts, quaternary ammonium salts such as tetra (normal-hexyl) ammonium chloride, trimethylbenzylammonium chloride, triethylbenzylammonium chloride, trimethylphenylammonium chloride and tetrabutylammonium hydrogensulfate are preferable.

The phase transfer catalyst may be used in an amount of from 1% to 100%, still preferably from about 3% to 30%, based on the molar number of the compound (IV).

The solvent is not particularly restricted so long as it exerts no undesirable effect on the reaction. Examples thereof include aliphatic hydrocarbon solvents such as n-hexane, and n-pentane; aromatic hydrocarbon solvents such as benzene, toluene and xylene; halogenated hydrocarbons such as chloroform, methylene chloride and 1,2-dichloroethane; ether solvents such as diethyl ether, diisopropyl ether, methyl t-butyl ether, tetrahydrofuran and 1,4-dioxane; ketone solvents such as acetone and methyl ethyl ketone; amide solvents such as N,N-dimethylformamide and N,N-dimethylacetamide; halogenated hydrocarbon solvents such as dichloromethane and chloroform; ester solvents such as methyl acetate and ethyl acetate; and alcohol solvents such as methanol, ethanol, propanol, isopropanol, n-butanol and t-butanol. In addition, use can be also made of water, acetonitrile, acetic acid esters, acetone, etc. Either one of these solvents or a mixture of several types thereof may be used.

As the solvent, aromatic hydrocarbon solvents, amide solvents, ketone solvents and halogenated hydrocarbon solvents are preferable and toluene, N,N-dimethylformamide, N,N-diemthylacetamide, acetone and dichloromethane are still preferable. Among these solvents, amide solvents such as N,N-dimethylformamide and N,N-dimethylacetamide are further preferable.

Although the reaction temperature varies depending on the solvent used, it usually ranges from −78° C. to the boiling point of the solvent, preferably from 40° C. to 80° C. and still preferably around 60° C.

The reaction time ranges from 1 to 24 hours. Usually, the reaction is completed within about 1 to 16 hours.

Continuous Step from Compound (IV) to Compound (VI)

The compound (VI) can be obtained at once by mixing the compound (IV) with a methylenemalonic acid dialkyl ester derivative and treating in the presence of a base. By this method, namely, the compound (VI) is synthesized from the compound (IV) at once without isolating the compound (V). In both of these two steps, the reactions can be performed by using a phase transfer catalyst. The products in the respective steps can be obtained each at a high yield and a high purity by performing the step for obtaining the compound (V) at room temperature and performing the step of the cyclization of the compound (V) under heating to about 60° C.

The methylenemalonic acid dialkyl ester derivative may be used in an amount of from 1 to 4 times (by mol), preferably from 1.5 to 3 times, as much based on the molar number of the compound (IV).

The solvent is not particularly restricted so long as it exerts no undesirable effect on the reaction. Examples thereof include aromatic hydrocarbon solvents such as benzene, toluene and xylene; ether solvents such as diethyl ether, tetrahydrofuran and 1,4-dioxane; ketone solvents such as acetone and methyl ethyl ketone; amide solvents such as N,N-dimethylformamide and N,N-dimethylacetamide; halogenated hydrocarbon solvents such as dichloromethane and chloroform; ester solvents such as methyl acetate and ethyl acetate; and alcohol solvents such as methanol, ethanol and isopropanol.

As the solvent, aromatic hydrocarbon solvents, amide solvents, ketone solvents and halogenated solvents are preferable and toluene, N,N-dimethylformamide, N,N-diemthylacetamide, acetone and dichloromethane are still preferable.

The base may be either an organic base or an inorganic base. Examples of the inorganic bases include alkali metal hydrides such as sodium hydride and lithium hydride; alkaline earth metal hydrides such as calcium hydride; alkali metal hydroxides such as sodium hydroxide and potassium hydroxide; alkali metal or alkaline earth metal carbonates or hydrogencarbonates such as sodium carbonate, potassium carbonate, sodium hydrogencarbonate and potassium hydrogencarbonate; and alkali metal or alkaline earth metal halides such as potassium fluoride, cesium fluoride and potassium iodide.

Examples of the organic bases include alkali metal alkoxides such as sodium methoxide, lithium methoxide, sodium ethoxide, lithium ethoxide, sodium tertiary-butoxide and potassium tertiary-butoxide; trialkylamines such as triethylamine and ethyldiisopropylamine; N,N-dialkylaniline derivatives carrying alkyl groups having from 1 to 4 carbon atoms such as N,N-dimethylaniline and N,N-diethylaniline; pyridine derivatives optionally substituted by alkyl groups having from 1 to 4 carbon atoms such as pyridine and 2,6-lutidine; and nitrogen-containing heterocyclic compounds such as 1,8-diazabicyclo[5.4.0]undec-7-ene.

Among these bases, it is preferable to use alkyl metal alkoxides, nitrogen-containing heterocyclic compounds and alkali metal or alkaline earth metal hydroxides. Potassium tertiary-butoxide, 1,8-diazabicyclo[5.4.0]undec-7-ene and alkali hydroxides are still preferable and potassium hydroxide is further preferable.

The base may be used in an amount of from 2 to 6 times by mol, preferably from 2 to 4 times, as much based on the molar number of the ester compound of the compound (IV).

In this reaction, the yield can be elevated by adding an additive. Examples of the additive include phase transfer catalysts and molecular sieves.

Examples of the phase transfer catalysts include quaternary ammonium salts such as tetra(normal-hexyl) ammonium chloride and tetra(normal-hexyl)ammonium iodide; and crown ethers such as 18-crown-6,15-crown-5.

As the additive, a phase transfer catalyst is preferable. Among all, a lipophilic quaternary ammonium salt is still preferable.

The phase transfer catalyst may be used in an amount of from 1 to 100%, still preferably from about 5 to 30%, based on the molar number of the compound (IV).

Although the reaction temperature is not particularly restricted so long as it does not exceed the boiling point of the solvent, it preferably ranges from room temperature to 60° C.

Although the reaction time varies depending on the reaction temperature, it may range from 1 hour to 3 days.

In case where the two steps are carried out continuously, for example, the phase transfer catalyst is added in the presence of a base (potassium hydroxide, etc., 1.5 time by mol as much based on the molar number of the compound (IV)) and the mixture is stirred at room temperature for about 1 hour. Next, the liquid reaction mixture is heated to 60° C. and base is added in the same amount as described above. After stirring for about 5 hours, the desired compound can be obtained. That is to say, the compound (V) is once formed by stirring at room temperature and then the base is added and the reaction temperature is elevated. Thus, the process until the cyclization reaction can be completed at once.

Step from Compound (IV) to Compound (VII)

The compound (VII) can be obtained by treating the compound (IV) in the presence of a base to thereby effect intramolecular cyclization.

The base to be used herein may be either an inorganic base or an organic base. Examples of the inorganic bases include alkali metal hydrides such as sodium hydride and lithium hydride; alkaline earth metal hydrides such as calcium hydride; alkali metal hydroxides such as sodium hydroxide and potassium hydroxide; alkali metal or alkaline earth metal carbonates or hydrogencarbonates such as sodium carbonate, potassium carbonate, sodium hydrogencarbonate and potassium hydrogencarbonate; and alkali metal or alkaline earth metal halides such as potassium fluoride, cesium fluoride and potassium iodide.

Examples of the organic bases include alkali metal or alkaline earth metal alkoxides such as sodium methoxide, lithium methoxide, magnesium methoxide, sodium ethoxide, lithium ethoxide, magnesium ethoxide, sodium tertiary-butoxide and potassium tertiary-butoxide; alkyl lithiums such as n-butyllithium, methyl lithium and lithium diisopropylamide; trialkylamines such as triethylamine and ethyldiisopropylamine; aniline derivatives carrying alkyl groups having from 1 to 4 carbon atoms such as N,N-dimethylaniline and N,N-diethylaniline; pyridine derivatives optionally substituted by alkyl groups having from 1 to 4 carbon atoms such as pyridine and 2,6-lutidine; and nitrogen-containing heterocyclic compounds such as 1,8-diazabicyclo[5.4.0]undec-7-ene (DBU) and 1,8-diazabicyclo[4.3.0]nona-5-ene (DBN).

Among these bases, it is preferable to use alkali metal or alkaline earth metal carbonates, alkali metal hydroxides, alkyl metal alkoxides and metal hydrides. More particularly, potassium carbonate, sodium hydroxide, potassium tertiary-butoxide, sodium tertiary-butoxide (t-BuONa) and sodium hydride are still preferable.

The base may be used in an amount of from 1 to 15 times by mol, preferably from about 1 to 3 times, as much based on the molar number of the ester compound of the compound (IV).

In case of using an alkali metal or an alkali metal carbonate or an alkali metal hydroxide, it is preferable to use an additive. Examples of the additive include phase transfer catalysts and molecular sieves. Examples of the phase transfer catalysts include quaternary ammonium salts such as tetra(normal-hexyl)ammonium chloride, tetra(normal-hexyl)ammonium iodide, tetrabutylammonium bromide and benzyltriethylammonium chloride. It is also possible to carry out the invention in the presence of an alkali metal or alkaline earth metal iodide such as potassium iodide or sodium iodide and a crown ether such as 18-crown-6,15-crown-5.

As the additive, a phase transfer catalyst is preferable. Among all, a lipophilic quaternary ammonium salt is still preferable.

The additive may be used in an amount of from 1 to 100%, preferably from 5 to 30%, based on the molar number of the compound (IV).

The solvent is not particularly restricted so long as it exerts no undesirable effect on the reaction. Examples thereof include aromatic hydrocarbon solvents such as benzene, toluene and xylene; aliphatic hydrocarbon solvents such as n-hexane, n-pentane and cyclohexane; ether solvents such as diethyl ether, diisopropyl ether, 1,2-dimethoxyethane, methyl t-butyl ether (MTBE), tetrahydrofuran and 1,4-dioxane; ketone solvents such as acetone and methyl ethyl ketone; amide solvents such as N,N-dimethylformamide and N,N-dimethylacetamide; halogenated hydrocarbon solvents such as dichloromethane and chloroform; ester solvents such as methyl acetate and ethyl acetate; and alcohol solvents such as methanol, ethanol, isopropanol, n-butanol and t-butanol.

As the solvent, amide solvents are preferable and N,N-dimethylformamide and N,N-diemthylacetamide are still preferable.

The reaction temperature is not particularly restricted but usually ranges from −78° C. to the boiling point of the solvent. It preferably ranges from room temperature to the boiling point of the solvent.

Although the reaction time varies depending on the reaction temperature, it may range from 15 minutes to 12 hours.

The compound (VII) thus obtained can be purified by forming a salt together with a compound represented by the following formula:

$R^{11}$—SO$_3$H

[wherein $R^{11}$ represents a phenyl group (which may have one or more groups of one or more types selected from the group consisting of halogen atoms, alkyl groups having from 1 to 6 carbon atoms, halogenoalkyl groups having from 1 to 6 carbon atoms, alkoxy groups having from 1 to 6 carbon atoms, nitro group, carbamoyl group and cyano group), a camphor group (which may have one or more groups of one or more types selected from the group consisting of halogen atoms, nitro group, carbamoyl group, cyano group, alkyl groups having from 1 to 6 carbon atoms, halogenoalkyl groups having from 1 to 6 carbon atoms and alkoxy groups having from 1 to 6 carbon atoms), an alkyl group having from 1 to 6 carbon atoms or a halogenoalkyl group having from 1 to 6 carbon atoms].

Since an optically active isomer of the compound (VII) is an oily substance, the purity of the final product levofloxacin can be elevated by the purification by forming such a salt as described above.

Among these sulfonic acids, methanesulfonic acid, para-toluenesulfonic acid and camphorsulfonic acid are preferable.

Examples of the solvent to be used in the formation of the salt include hydrocarbon solvents such as n-hexane and n-pentane; aromatic hydrocarbon solvents such as benzene, toluene and xylene; alcohol solvents such as methanol, ethanol, propanol, isopropanol, n-butanol and t-butanol; ether solvents such as diethyl ether, diisopropyl ether, methyl t-butyl ether, tetrahydrofuran, 1,2-dimethoxyethane and 1,4-dioxane; amide solvents such as N,N-dimethylformamide and N,N-dimethylacetamide; and halogenated hydrocarbon solvents such as chloroform, methylene chloride and 1,2-dichloroethane. In addition, use can be also made of water, acetonitrile, acetic acid esters, acetone, etc. Either one of these solvents or a mixture of several types thereof may be used.

Among these solvents, aromatic hydrocarbon solvents such as toluene, acetic cid esters and acetone are preferable.

The solvent may be used usually in an amount of from about 1 to 100 times by weight, preferably from about 2 to 50 times by weight, as much.

Although the temperature for the crystallization of the target salt is not constant, temperature conditions commonly used in the art may be used therefor. More particularly speaking, it may be carried out within a temperature range from ice-cooling to the boiling point of the solvent used. The salt may be formed in the following manner. After the completion of the cyclization reaction to give the compound (VII), the solvent is replaced by another solvent to be used in the salt formation and then sulfonic acid is added. It is needless to say that the liquid reaction mixture after the cyclization may be treated and isolated in the conventional manner to thereby form the salt.

The salt thus formed can be converted into a free compound by treating with an alkali. For example, use can be made of bases including alkali metal hydroxides such as sodium hydroxide and potassium hydroxide, alkali metal carbonates such as sodium carbonate and potassium carbonate, and alkali metal hydrogencarbonate such as sodium hydrogencarbonate and potassium hydrogencarbonate. Such a base is usually used in the form of an aqueous solution and the free compound can be isolated by extraction, etc.

Step from Compound (VII) to Compound (VI)

The compound (VI) can be obtained by reacting the compound (VII) with a methylenemalonic acid dialkyl ester derivative.

In this step, the compound (VI) can be obtained by adding the methylenemalonic acid dialkyl ester derivative to the compound (VII) and heating, or treating the compound (VII) and the methylenemalonic acid dial kyl ester derivative in a solvent in the presence of a base.

(1) Method of Adding Methylenemalonic Acid Dialkyl Ester Derivative to Compound (VII) Followed by Heating The methylenemalonic acid dialkyl ester derivative may be used in an amount from 1 to 3 times by mol, preferably from 1.1 to 1.6 time, as much based on the molar number of the compound (VII).

The reaction can be performed either without using a solvent or in a solvent. As the solvent, use can be made of any one so long as it exerts no effect on the reaction. Examples thereof include aromatic hydrocarbon solvents such as toluene and xylene.

It is preferable to perform the reaction without using a solvent or using an aromatic hydrocarbon solvent such as toluene or xylene.

The reaction temperature is not particularly restricted so long as it does not exceed the boiling point of the solvent. It preferably ranges from 100° C. to 160° C. Although the reaction time varies depending on the reaction temperature, it is usually completed within 1 hour to 1 day.

(2) Method of Treating Compound (VII) and Methylenemalonic Acid Dialkyl Ester Derivative in Solvent in the Presence of Base and Phase Transfer Catalyst The methylenemalonic acid dialkyl ester derivative may be used in an amount from 1 to 3 times by mol, preferably from 1.05 to 2 times, as much based on the molar number of the compound (VII).

The solvent is not particularly restricted so long as it exerts no undesirable effect on the reaction. Examples thereof include aromatic hydrocarbon solvents such as benzene, toluene and xylene; ether solvents such as diethyl ether, tetrahydrofuran and 1,4-dioxane; ketone solvents such as acetone and methyl ethyl ketone; amide solvents such as N,N-dimethylformamide and N,N-dimethylacetamide; halogenated hydrocarbon solvents such as dichloromethane and chloroform; ester solvents such as methyl acetate and ethyl acetate; and alcohol solvents such as methanol, ethanol and isopropanol.

Among these solvents, aromatic hydrocarbon solvents, amide solvents, ketone solvents and halogenated solvents are preferable and toluene, N,N-dimethylformamide, acetone and dichloromethane are still preferable.

The base may be either an organic base or an inorganic base. Examples of the inorganic bases include alkali metal hydrides such as sodium hydride and lithium hydride; alkaline earth metal hydrides such as calcium hydride; alkali metal alkoxides such as sodium methoxide, lithium methoxide, sodium ethoxide, lithium ethoxide, sodium tertiary-butoxide and potassium tertiary-butoxide; alkali metal hydroxides such as sodium hydroxide and potassium hydroxide; alkali metal or alkaline earth metal carbonates or hydrogencarbonates such as sodium carbonate, potassium carbonate, sodium hydrogencarbonate and potassium hydrogencarbonate; and alkali metal or alkaline earth metal halides such as potassium fluoride, cesium fluoride and potassium iodide.

Examples of the organic bases include trialkylamines such as triethylamine and ethyldiisopropylamine; aniline derivatives carrying alkyl groups having from 1 to 4 carbon atoms such as N,N-dimethylaniline and N,N-diethylaniline; pyridine derivatives optionally substituted by alkyl groups having from 1 to 4 carbon atoms such as pyridine and 2,6-lutidine; and nitrogen-containing heterocyclic compounds such as 1,8-diazabicyclo[5.4.0]undec-7-ene.

As the base, alkyl metal alkoxides is preferable and potassium tertiary-butoxide is still preferable.

The base may be used in an amount of from 1 to 3 times by mol, preferably from 1 to 2 times, as much based on the molar number of the ester compound of the compound (VII).

Although the reaction time varies depending on the reaction temperature, it is usually completed within 1 hour to 1 day.

By carrying out the processes as described above, the compound (VI) can be produced from the compound (I). It is expected that the following step can be also used therefor in addition to these processes.

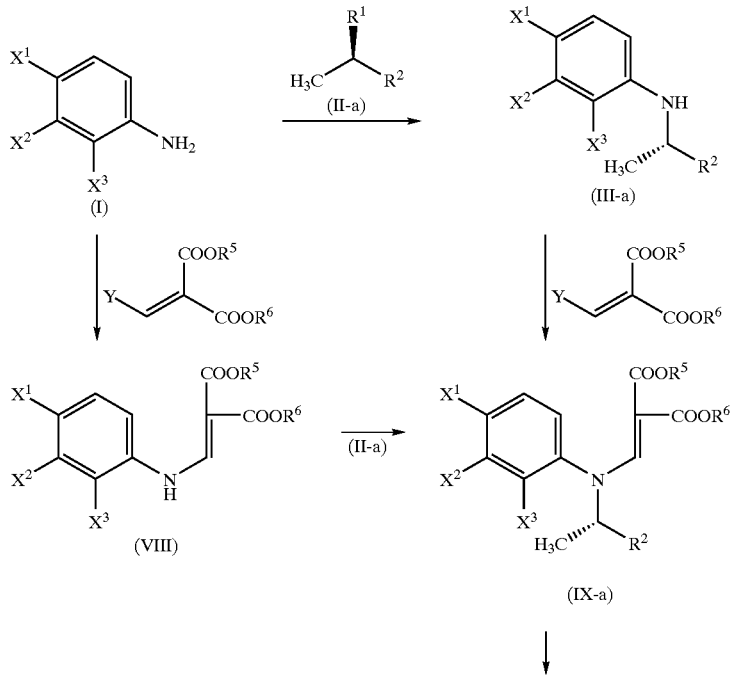

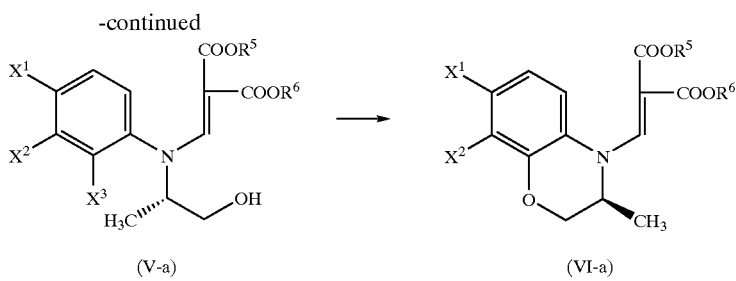

(V-a) → (VI-a)

The compound (VI-a) thus obtained can be converted into levofloxacin by a known method. Now, the method will be briefly described. Namely, the compound (VI-a) is subjected to cyclization by heating together with polyphosphoric acid or its ester to give a tricyclic carboxylic acid ester compound. Next, this carboxylic acid ester is hydrolyzed under basic or acidic conditions to give a tricyclic carboxylic acid compound. This tricyclic carboxylic acid compound is then reacted with 4-methylpiperazine in the presence of a base and thus levofloxacin can be obtained. The base may be either an inorganic base or an organic base. Examples of the inorganic base include alkali metal or alkaline earth metal carbonates and hydrogencarbonates. Examples of the organic acids include trialkylamines and nitrogen-containing heterocyclic compounds. More particularly speaking, triethylamine, tributylamine, ethyldiisopropylamine, etc. or 4-methylmorpholine, dimethylaminopyridine, etc., or 4-methylpiperazine may be used in excess to thereby make it to serve as a base too. It is favorable to use a solvent in this reaction and dimethyl sulfoxide is usable as the solvent. In the reaction of 4-methylpiperazine, it is more effective to use not the tricyclic carboxylic acid compound but a dihalogenoboron chelate compound of this carboxylic acid. This dihalogenoboron chelate compound may be obtained by reacting the tricyclic carboxylic acid compound with a trihalogenoboron compound. It is convenient to use a complex of the trihalogenobron compound with an ether compound, for example, a diethyl ether complex or a tetrahydrofuran complex. As the halogen atom, fluorine atom is preferable. By stirring this ether complex with the carboxylic acid in various ether solvents, a dihalogenoborn chelate compound of the carboxylic acid can be obtained. The reaction with 4-methylpiperazine may be carried out in a solvent in the presence of a base similar to the above-described case. The dihalogenoboron chelate compound of the carboxylic acid can be obtained in a single step by heating the compound (VI-a), a dihalogenoboron compound (preferably a complex with an ether compound) in a solvent (for example, acetic anhydride). After the completion of the reaction with 4-methylpiperazine, it is necessary to eliminate (hydrolyze) the chelate. It can be performed by heating in an aprotic solvent in the presence of a base to thereby cleave and eliminate. For example, it may be cited to heat in an alcohol solvent in the presence of a trialkylamine. More particularly speaking, it may be heated and stirred in ethanol in the presence of triethylamine.

BEST MODE FOR CARRYING OUT THE INVENTION

Now, the present invention will be illustrated in greater detail by reference to the following Examples. However, it is to be understood that the present invention is not construed as being restricted thereto.

EXAMPLE 1

Methyl (2S)-2-(2,3,4-trifluoroanilino)propionate

Under ice-cooling, methyl D-lactate (8.5 g) and 2,6-lutidine (11.4 g) were dissolved in dichloromethane (100 ml). After dropping anhydrous trifluoromethanesulfonic acid (25.4 g), the mixture was heated to room temperature and stirred for 30 minutes. Then it was cooled to 0° C. again and a solution (30 ml) of 2,3,4-trifluoroaniline (12.0 g) in dichloromethane was dropped thereinto. The mixture was stirred at the same temperature for 17 hours. To the resultant solution, hydrochloric acid (0.5 mol/l) was added and the mixture was extracted with dichloromethane. The extract was washed with a saturated aqueous solution of sodium chloride, dried over magnesium sulfate and filtered. After evaporating the solvent, the residue thus obtained was subjected to silica gel column chromatography. Thus, 17.1 g (90%) of the title compound was obtained as an oily substance. The optical purity determined by HPLC was 97% ee.

$^1$H-NMR (CDCl$_3$, 270 MHz) δ: 1.51 (d, J=6.9 Hz, 3H), 3.73 (s, 3H), 4.07–4.13 (m, 1H), 4.22 (brs, 1H), 6.22–6.31 (m, 1H), 6.73–6.85 (m, 1H)

IR (nujol): 3407, 2994, 2956, 1739 cm$^{-1}$

MS;m/z: 233(M$^+$)

EXAMPLE 2

Methyl (2S)-2-(2,3,4-trifluoroanilino)propionate 2,3,4-Trifluoroaniline (100 mg) was dissolved in toluene (1 ml). After adding potassium carbonate (188 mg), methyl (2R)-2-[[(4-methylphenyl)sulfonyl]oxy]propionate (193 mg) and tetrahexylammonium chloride (40 mg), the mixture was stirred under heating and refluxing for 15.5 hours. After treating as in Example 1, the obtained product was analyzed by reversed phase HPLC with the use of the compound of Example 1 as a specimen. As a result, the product corresponded to 41 mg (26%) of the title compound.

EXAMPLE 3

Methyl (2S)-2-(2,3,4-trifluoroanilino)propionate

In accordance with the process of Example 2, a condensation reaction was performed by using 2,3,4-trifluoroaniline (100 mg), potassium carbonate (188 mg), methyl (2R)-2-[(methanesulfonyl)oxy]propionate (78 mg) and tetrahexylammonium chloride (40 mg) to give the title compound as an oily substance. As the result of the analysis by reversed phase HPLC with the use of the compound of Example 1 as a specimen, the product corresponded to 38 mg (24%) of the title compound.

EXAMPLE 4

Methyl (2S)-2-(2,3,4-trifluoroanilino)propionate

In accordance with the process of Example 2, a condensation reaction was performed by using 2,3,4- trifluoroaniline (100 mg), potassium carbonate (188 mg), methyl (2R)-chloropropionate (92 mg) and tetrahexylammonium chloride (40 mg). As the result of the analysis by reversed phase HPLC with the use of the compound of Example 1 as a specimen, the product corresponded to 56 mg (36%) of the title compound.

EXAMPLE 5

Methyl 2-(2,3,4-trifluoroanilino)propionate 2,3,4-Trifluoronitrobenzene (100 g) and methyl pyruvate (57.6 g) were dissolved in methanol (1000 ml). After adding 5% Pd-C (20.0 g) and anhydrous magnesium sulfate (90 g), the mixture was stirred at room temperature in a hydrogen atmosphere for 16 hours. Then the liquid reaction mixture was filtered through celite to thereby eliminate Pd-C and magnesium sulfate. The obtained filtrate was concentrated under reduced pressure and Florisil (100 g) and diethyl ether (700 ml) were added to the residue. After stirring for 2 hours, the liquid reaction mixture was filtered. The obtained organic layer was evaporated and the crystals thus precipitated were filtered while washing with hexane. Thus the title compound (128.2 g) was obtained as slightly yellowish crystals.

Melting point: 41 to 43° C.

$^1$H-NMR (CDCl$_3$) δ: 1.51 (d, J=6.9 Hz, 3H), 3.74 (s, 3H), 4.0–4.3 (m, 2H), 6.2–6.4 (m, 1H), 6.7–6.9 (m, 1H)

IR (KBr): 3357, 1719, 1510 cm$^{-1}$

Elemental analysis as $C_{10}H_{10}NO_2F_3$

| | |
|---|---|
| Calculated (%): | C, 51.51; H, 4.32; N, 6.01 |
| Found (%): | C, 51.65; H, 4.31; N, 5.99 |

EXAMPLE 6

Methyl 2-(2,3,4-trifluoroanilino)propionate 2,3,4-Trifluoroaniline (2.94 g) and methyl pyruvate (2.04 g) were dissolved in methanol (30 ml). After adding 5% Pd-C (2.0 g) and anhydrous magnesium sulfate (2.65 g), the mixture was stirred at 50° C. in a hydrogen atmosphere for 16 hours. After filtering off Pd-C and magnesium sulfate, the obtained filtrate was concentrated under reduced pressure. The crystals thus precipitated were filtered while washing with hexane. Thus the title compound (4.44 g) was obtained as slightly yellowish crystals. Various spectral data of this product was identical with those obtained in Example 5.

EXAMPLE 7

Ethyl 2-(2,3,4-trifluoroanilino)propionate 2,3,4-Trifluoronitrobenzene (3.54 g) and methyl pyruvate (2.32 g) were dissolved in ethanol (30 ml). After adding 5% Pd-C (2.0 g) and anhydrous magnesium sulfate (2.65 g), the mixture was stirred at 50° C. in a hydrogen atmosphere for 16 hours. After filtering off Pd-C and magnesium sulfate, the obtained filtrate was concentrated under reduced pressure. The residue thus obtained was subjected to silica gel column chromatography (ethyl acetate-normal hexane=1:4) to give the title compound (4.84 g) as a pale yellow oily substance.

$^1$H-NMR (CDCl$_3$) δ: 1.25 (t, J=7.1 Hz, 3H), 1.50 (d, J=7.1 Hz, 3H), 4.0–4.3 (m, 2H), 4.19 (dd, J=7.3, 10.9 Hz, 3H), 6.2–6.4 (m, 1H), 6.7–6.9 (m, 1H)

IR (cm$^{-1}$) 1737, 1524, 909

EXAMPLE 8

Ethyl 2-(2,3,4-trifluoroanilino)propionate 2,3,4-Trifluoroaniline (2.94 g) and ethyl pyruvate (2.32 g) were dissolved in methanol (30 ml). After adding 5% Pd-C (2.0 g) and anhydrous magnesium sulfate (2.65 g), the mixture was stirred at 50° C. in a hydrogen atmosphere for 16 hours. After filtering off Pd-C and magnesium sulfate, the obtained filtrate was concentrated under reduced pressure. The obtained residue was subjected to silica gel column chromatography (ethyl acetate-normal hexane=1:4) to thereby give the title compound (4.69 g) as a pale yellow oily substance. Various spectral data of this product was identical with those obtained in Example 7.

EXAMPLE 9

Methyl 2-(2,3,4-trifluoroanilino)propionate 2,3,4-Trifluoroaniline (1.01 g) and methyl pyruvate (0.87 g) were dissolved in methanol (8 ml). After adding 5% Pd-C (0.11 g) and conc. hydrochloric acid (0.03 g), the mixture was stirred at 40° C. under a hydrogen gas pressure of 2.94 MPa (converted from 30 kgf/cm$^2$) for 2 hours. After filtering off Pd-C, the obtained filtrate was concentrated under reduced pressure. Thus the title compound (1.31 g) was obtained as slightly yellowish crystals. Various spectral data of this product was identical with those obtained in Example 5.

EXAMPLE 10

Ethyl 2-(2,3,4-trifluoroanilino)propionate 2,3,4-Trifluoronitrobenzene (1.01 g) and ethyl pyruvate (1.15 g) were dissolved in ethanol (8 ml). After adding 5% Pd-C (0.11 g) and conc. hydrochloric acid (0.03 g), the mixture was stirred at 40° C. under a hydrogen gas pressure of 2.94 MPa for 3 hours. After filtering off Pd-C, the obtained filtrate was concentrated under reduced pressure. Thus the title compound (1.38 g) was obtained as slightly yellow oily substance. Various spectral data of this product was identical with those obtained in Example 7.

EXAMPLE 11

Methyl 2-(2,3,4-trifluoroanilino)propionate 2,3,4-Trifluoroaniline (0.83 g) and methyl pyruvate (0.87 g) were dissolved in methanol (8 ml). After adding 5% Pd-C (0.11 g) and conc. hydrochloric acid (0.03 g), the mixture was stirred at 40° C. under a hydrogen gas pressure of 2.94 MPa for 2 hours. After filtering off Pd-C, the obtained filtrate was concentrated under reduced pressure. Thus the title compound (1.26 g) was obtained as slightly yellowish crystals. Various spectral data of this product was identical with those obtained in Example 5.

EXAMPLE 12

Ethyl 2-(2,3,4-trifluoroanilino)propionate 2,3,4-Trifluoroaniline (0.83 g) and ethyl pyruvate (1.15 g) were dissolved in ethanol (8 ml). After adding 5% Pd-C (0.11 g) and conc. hydrochloric acid (0.03 g), the mixture was stirred at 40° C. under a hydrogen gas pressure of 2.94 MPa for 3 hours. After filtering off Pd-C, the obtained filtrate was concentrated under reduced pressure. Thus the title compound (1.32 g) was obtained as slightly yellow oily substance. Various spectral data of this product was identical with those obtained in Example 7.

EXAMPLE 13

2-(2,3,4-Trifluoroanilino)propionic acid 2,3,4-Trifluoronitrobenzene (5.03 g) and pyruvic acid (2.75 g) were dissolved in isopropanol (IPA; 40 ml). After adding 10% Pd-C (0.21 g), the mixture was stirred at 40° C. under atmospheric pressure in a hydrogen atmosphere for 3 hours. After filtering off Pd-C, the obtained filtrate was concentrated under reduced pressure. Thus the title compound (6.11 g) was obtained as colorless crystals. Various spectral data of this product was identical with those of a specimen synthesized separately.

EXAMPLE 14

2-(2,3,4-Trifluoroanilino)propionic acid 2,3,4-Trifluoronitrobenzene (5.03 g) and pyruvic acid (2.75 g) were dissolved in IPA (40 ml). After adding 10% Pd-C (0.21 g), the mixture was stirred at 40° C. under a hydrogen gas pressure of 2.94 MPa for 3 hours. After filtering off Pd-C, the obtained filtrate was concentrated under reduced pressure. Thus the title compound (6.09 g) was obtained as colorless crystals. Various spectral data of this product was identical with those of a specimen synthesized separately.

EXAMPLE 15

2-(2,3,4-Trifluoroanilino)propionic acid 2,3,4-Trifluoronitrobenzene (1.01 g) and pyruvic acid (0.75 g) were dissolved in methanol (8 ml). After adding 5% Pd-C (0.11 g), the mixture was stirred at 40° C. under a hydrogen gas pressure of 4.9 MPa (converted from 50 kgf/cm$^2$) for 5 hours. After filtering off Pd-C, the obtained filtrate was concentrated under reduced pressure. Thus the title compound (1.20 g) was obtained as colorless crystals. Various spectral data of this product was identical with those of a specimen synthesized separately.

EXAMPLE 16

2-(2,3,4-Trifluoroanilino)propionic acid 2,3,4-Trifluoroaniline (4.18 g) and pyruvic acid (2.75 g) were dissolved in IPA (40 ml). After adding 10% Pd-C (0.21 g), the mixture was stirred at 40° C. under atmospheric pressure in a hydrogen atmosphere for 3 hours. After filtering off Pd-C, the obtained filtrate was concentrated under reduced pressure. Thus the title compound (5.69 g) was obtained as colorless crystals. Various spectral data of this product was identical with those of a specimen synthesized separately.

EXAMPLE 17

N-(1-Methoxycarbonylethylidene)-2,3,4-trifluoroaniline

Trifluoroaniline (1 g) and magnesium sulfate (1.36 g) were stirred in methanol (5 ml) at room temperature. After adding methyl pyruvate (1.27 g) thereto, the mixture was heated to 40° C. and stirred for 20 hours. After the completion of the reaction, magnesium sulfate was filtered off. The filtrate thus obtained was concentrated under reduced pressure and the residue was subjected to silica gel column chromatography (hexane-diethyl ether=1:3) to thereby give the title compound (552 mg) as methanol crystals.

$^1$H-NMR(CDCl$_3$)d: 6.92–6.74(m, 2H), 5.09 (brs, 1H), 3.84 (s, 3H), 3.24 (s, 3H), 1.65 (s, 3H)

EXAMPLE 18

Methyl (2S)-2-(2,3,4-trifluoroanilino)propionate

Chloro-1,5-cyclooctadiene iridium dimer (12.8 mg) and (2S,4S)-BCPM (23.6 mg) were dissolved in IPA (2 ml) under an argon gas stream and stirred at room temperature for 1 hour. To this liquid reaction mixture was added a solution of N-(1-methoxycarbonylethylidene)-2,3,4-tirfluoroaniline mono-methanol crystal (50 mg) in IPA (2 ml). The liquid reaction mixture was transferred into an autoclave and a hydrogen pressure of 50 kg/cm$^2$ was applied. Then the liquid reaction mixture was stirred at 10° C. for 15 hours. The chemical yield and optical purity of the title compound contained in the final liquid reaction mixture measured by high performance liquid chromatography were 70% and 50% ee (S-compound) respectively.

EXAMPLES 19 TO 22

By altering the optically active ligand, imino compounds were asymmetrically reduced by the same method as the reaction described above. The results of these Examples are summarized in the following Table.

TABLE

| Ex. | Optically active ligand | Additive | Reaction temp. (° C.) | Reaction time (h) | Chemical Yield (%) | Asymmetric yield (ee %) |
|---|---|---|---|---|---|---|
| 19 | (S)-(R)-JOSIPHOS | none | 10 | 15.5 | 19.4 | 63.0 |
| 20 | (2S, 4S)-BCPM | KI/SiO$_2$ | 20 | 18.5 | 17.1 | 71.7 |
| 21 | (4R, 5R)-MOD-DIOP | none | 10 | 14.5 | 97.4 | 20.7 |
| 22 | (2S, 4S)-BCPM | zeolite 4A | 20 | 16 | 79.5 | 50.5 |

(2S,4S)-BCPM:
(2S,4S)-N-(t-butoxycarbonyl)-4-(dicyclohexylphosphino)-2-[(diphenylphosphino)methyl]pyrrolidine
(S)-(R)-JOSIPHOS:
(S)-1-[(R)-2-(diphenylphosphino)ferrocenyl]ethyldicyclohexylphosphine
(4R,5R)-MOD-DIOP:
(4R,5R)-4,5-bis[[bis(4'-methoxy-3',5'-dimethylphenyl)phosphino]methyl]-2,2-dimethyl-1,3-dioxolane

EXAMPLE 23

2-(2,3,4-Trifluoroanilino)propionic acid

Methyl 2-(2,3,4-trifluoroanilino)propionate (46.64 g) was dissolved in methanol (130 ml) and an aqueous solution (3 mol/l; 100 ml) of lithium hydroxide was slowly added thereto at 0° C. After stirring at room temperature for 3 hours, the solvent was evaporated. After adding water, the residue was washed with chloroform. Next, hydrochloric acid (6 mol/l) was slowly added to the aqueous layer until pH value reached 1. Then the aqueous layer was extracted with diisopropyl ether (IPE). The organic layer was dried over anhydrous magnesium sulfate and then the solvent was evaporated to give the title compound (43.7 g) as colorless crystals.

Melting point: 114 to 119° C.

$^1$H-NMR (CDCl$_3$) δ: 1.57 (d, J=6.9 Hz, 3H), 4.11 (dd, J=6.9, 10.3 Hz, 1H), 6.2–6.4 (m, 1H), 6.7–6.9 (m, 1H)

IR (cm$^{-1}$): 3357, 1725, 1524, 1195

Elemental analysis as C$_9$H$_8$NO$_2$F$_3$

| | |
|---|---|
| Calculated (%): | C, 49.32; H, 3.68; N, 6.39 |
| Found (%): | C, 49.33; H, 3.65; N, 6.34 |

EXAMPLE 24

2-(2,3,4-Trifluoroanilino)propionic acid

Ethyl 2-(2,3,4-trifluoroanilino)propionate (2.47 g) was dissolved in ethanol (40 ml) and an aqueous solution (3 mol/l; 10 ml) of sodium hydroxide was slowly added thereto at 0° C. After stirring at room temperature for 3 hours, the solvent was evaporated. After adding water, the residue was washed with chloroform. Next, hydrochloric acid (6 mol/l) was slowly added to the aqueous layer until pH value reached 1. Then the aqueous layer was extracted with IPE. The organic layer was dried over anhydrous magnesium sulfate and then the solvent was evaporated to give the title compound (2.19 g) as colorless crystals. Various spectral data of this product was identical with those obtained in Example 23.

EXAMPLE 25

(2S)-2-(2,3,4-Trifluoroanilino)propionic acid (R)-1-phenyethylamine salt 2-(2,3,4-Trifluoroanilino)propionic acid (1.1 g) was dissolved in a solvent mixture (15 ml; methanol-IPE=1:20). At room temperature, a solution (15 ml) of (R)-1-phenylethylamine (333.2 mg) in a solvent mixture (methanol-IPE=1:20) was slowly added thereto. The obtained suspension was stirred at room temperature for additional 2 hours and then filtered while washing with IPE. Thus, the title compound was obtained as colorless crystals (802 mg). The optical purity of this product was 80% ee. Subsequently, chloroform was added to the obtained salt and the mixture was stirred at 50° C. for 18 hours. Then the suspension was filtered while washing with IPE to give 703 mg of the title compound as colorless crystals. The optical purity of this product was 99% ee.

[α]$_D$=5.7° (c=0.386, methanol)

Melting point (decomposition): 189 to 197° C.

$^1$H-NMR (CD$_3$OD) δ: 1.41 (d, J=6.9 Hz, 3H), 1.61 (d, J=6.9 Hz, 3H), 3.80 (dd, J=6.9, 15.4 Hz, 1H), 4.42 (dd, J=6.9, 10.0 Hz, 1H), 6.3–6.5 (m, 1H), 6.7–6.9(m, 1H), 7.3–7.5 (m, 5H)

Elemental analysis as C$_{17}$H$_{19}$NO$_2$F$_3$

| | |
|---|---|
| Calculated (%): | C, 60.86; H, 5.96; N, 7.91 |
| Found (%): | C, 61.01, H, 5.97; N, 7.85 |

EXAMPLE 26

(2S)-2-(2,3,4-Trifluoroanilino)propionic acid•(R)-1-triethylamine salt 2-(2,3,4-Trifluoroanilino)propionic acid (1.1 g) was dissolved in a solvent mixture (15 ml; methanol-IPE=1:20). At room temperature, a solution (15 ml) of (R)-1-tolylethylamine (371.8 mg) in a solvent mixture (methanol-IPE=1:20) was slowly added thereto. The obtained suspension was stirred at room temperature for additional 2 hours and then filtered while washing with IPE. Thus, the title compound was obtained as colorless crystals (860 mg). The optical purity of this product was 52% ee. Subsequently, chloroform was added to the obtained salt and the mixture was stirred at 50° C. for 18 hours. Then the suspension was filtered while washing with IPE to give 591 mg of the title compound as colorless crystals. The optical purity of this product was 99% ee.

[α]$_D$=-2.0° (c=0.197, methanol)

Melting point (decomposition): 190 to 197° C.

$^1$H-NMR (CD$_3$OD) δ: 1.41 (d, J=6.9 Hz, 3H), 1.59 (d, J=6.9 Hz, 3H), 2.35 (s, 3H), 3.80 (dd, J=6.9, 12.0 Hz, 1H), 4.38 (dd, J=6.9, 12.0 Hz, 1H), 6.3–6.5 (m, 1H), 6.7–6.9 (m, 1H), 7.2–7.3 (m, 4H)

Elemental analysis as C$_{18}$H$_{21}$NO$_2$F$_3$

| | |
|---|---|
| Calculated (%): | C, 59.99; H, 5.63; N, 8.23 |
| Found (%): | C, 59.96; H, 5.67; N, 8.16 |

EXAMPLE 27

(2S)-2-(2,3,4-Trifluoroanilino)propionic acid•(S)-1-phenyl-2-p-triethylamine salt 2-(2,3,4-Trifluoroanilino)propionic acid (1.1 g) was dissolved in a solvent mixture (15 ml; methanol-IPE=1:20). At room temperature, a solution (15 ml) of (R)-1-p-tolylethylamine (581.8 mg) in a solvent mixture (methanol-IPE=1:20) was slowly added thereto. The obtained suspension was stirred at room temperature for additional 2 hours and then filtered while washing with IPE. Thus, the title compound was obtained as 1.1 g of colorless crystals. The optical purity of this product was 79% ee. Subsequently, chloroform was added to the obtained salt and the mixture was stirred at 50° C. for 18 hours. Then the suspension was filtered while washing with IPE to give 923 mg of the title compound as colorless crystals. The optical purity of this product was 99% ee.

[α]$_D$=-5.6° (c=0.386, methanol)

Melting point (decomposition): 187 to 193° C.

$^1$H-NMR (CD$_3$OD) δ: 1.41 (d, J=6.9 Hz, 3H), 2.26 (s 3H), 3.0–3.3 (m, 2H), 3.81 (dd, J=6.9, 11.7 Hz, 1H), 4.43 (dd, J=6.6, 8.3 Hz), 6.3–6.5 (m, 1H), 6.7–6.9 (m, 1H), 7.00 (dd, J=7.9, 21.0 Hz), 7.2–7.3 (m, 5H)

Elemental analysis as C$_{23}$H$_{23}$O$_2$F$_3$

| Calculated (%): | C, 66.96; H, 5.85; N, 6.51 |
|---|---|
| Found (%): | C, 56.85; H, 5.89; N, 6.44 |

EXAMPLE 28

(2S)-2-(2,3,4-Trifluoroanilino)propionic acid

To (2S)-2-(2,3,4-trifluoroanilino)propionic acid•(S)-1-phenylethylamine salt (1.0 g; 99% ee) were added IPE (20 ml) and hydrochloric acid (1 mol/l) until the pH value reached 1 and the resultant mixture was stirred at room temperature for 1 hour. The organic layer was dried over anhydrous magnesium sulfate. After evaporating the solvent, 618 mg of the title compound was obtained as colorless crystals. The optical purity of this product was 99% ee. The $^1$H-NMR and IR spectral data of this product was identical with those of the compound obtained in Example 23.

EXAMPLE 29

(2S)-2-(2,3,4-Trifluoroanilino)propionic acid

To (2S)-2-(2,3,4-trifluoroanilino)propionic acid (S)-1-triethylamine salt (1.0 g; 99% ee) were added IPE (22 ml) and hydrochloric acid (1 mol/l) until the pH value reached 1 and the resultant mixture was stirred at room temperature for 1 hour. The organic layer was dried over anhydrous magnesium sulfate. After evaporating the solvent, 645 mg of the title compound was obtained as colorless crystals. The optical purity of this product was 99% ee. The $^1$H-NMR and IR spectral data of this product was identical with those of the compound obtained in Example 23.

EXAMPLE 30

(2S)-2-(2,3,4-Trifluoroanilino)propionic acid

To (2S)-2-(2,3,4-trifluoroanilino)propionic acid•(R)-1-phenyl-2-p-triethylamine salt (1.0 g; 99% ee) were added IPE (25 ml) and hydrochloric acid (1 mol/l) until the pH value reached 1 and the resultant mixture was stirred at room temperature for 1 hour. The organic layer was dried over anhydrous magnesium sulfate. After evaporating the solvent, 510 mg of the title compound was obtained as colorless crystals. The optical purity of this product was 99% ee. The $^1$H-NMR and IR spectral data of this product was identical with those of the compound obtained in Example 23.

EXAMPLE 31

Methyl (2S)-2-(2,3,4-trifluoroanilino)propionate (2S)-2-(2,3,4-trifluoroanilino)propionic acid (1.1 g; 99% ee) was dissolved in methanol (10 ml) and hydrochloric acid (5 mol/l; 1 ml) was added thereto at room temperature. The liquid reaction mixture was heated under reflux for 6 hours and then the solvent was evaporated. To the obtained residue was added chloroform (10 ml). Next, the organic layer was washed with a saturated aqueous solution of sodium chloride and water and dried over anhydrous magnesium sulfate. After evaporating the solvent, the obtained residue was subjected to silica gel column chromatography (ethyl acetate-normal hexane=1:4) to give the title compound (1.17 g) as an oily substance. The optical purity of the product was 99% ee. The $^1$H-NMR and IR spectral data of this product was identical with those of the compound obtained in Example 5.

$[\alpha]_D$=−49.4° (c=0.119, methanol)

EXAMPLE 32

Methyl (2R)-2-(2,3,4-trifluoroanilino)propionate (2R)-2-(2,3,4-trifluoroanilino)propionic acid (1.1 g; 98% ee) was dissolved in methanol (10 ml) and hydrochloric acid (5 mol/l; 1 ml) was added thereto at room temperature. The liquid reaction mixture was heated under reflux for 6 hours and then the solvent was evaporated. To the obtained residue was added chloroform (10 ml). Next, the organic layer was washed with a saturated aqueous solution of sodium chloride and water and dried over anhydrous magnesium sulfate. After evaporating the solvent, the obtained residue was subjected to silica gel column chromatography (ethyl acetate-normal hexane=1:4) to give the title compound (1.17 g) as an oily substance. The optical purity of the product was 99% ee. The $^1$H-NMR and IR spectral data of this product was identical with those of the compound obtained in Example 5.

EXAMPLE 33

Ethyl (2S)-2-(2,3,4-trifluoroanilino)propionate (2S)-2-(2,3,4-trifluoroanilino)propionic acid (219 mg; 99% ee) was dissolved in ethanol (2 ml) and hydrochloric acid (5 mol/l; 0.2 ml) was added thereto at room temperature. The liquid reaction mixture was heated under reflux for 6 hours and then the solvent was evaporated. To the obtained residue was added chloroform. Next, the organic layer was washed with a saturated aqueous solution of sodium chloride and water and dried over anhydrous magnesium sulfate. After evaporating the solvent, the obtained residue was subjected to silica gel column chromatography (ethyl acetate-normal hexane=1:4) to give the title compound (246 mg) as a pale yellow oily substance. The optical purity of the product was 99% ee. The $^1$H-NMR and IR spectral data of this product was identical with those of the compound obtained in Example 7.

$[\alpha]_D$=−57.2° (c=0.352, methanol)

EXAMPLE 34

Ethyl (2R)-2-(2,3,4-trifluoroanilino)propionate (2R)-2-(2,3,4-trifluoroanilino)propionic acid (219 mg; 99% ee) was dissolved in ethanol (2 ml) and hydrochloric acid (5 mol/l; 0.2 ml) was added thereto at room temperature. The liquid reaction mixture was heated under reflux for 6 hours and then the solvent was evaporated. To the obtained residue was added chloroform (10 ml). Next, the organic layer was washed with a saturated aqueous solution of sodium chloride and water and dried over anhydrous magnesium sulfate. After evaporating the solvent, the obtained residue was subjected to silica gel column chromatography (ethyl acetate-normal hexane=1:4) to give the title compound (245 mg) as a pale yellow oily substance. The optical purity of the product was 98% ee. The $^1$H-NMR and IR spectral data of this product was identical with those of the compound obtained in Example 7.

EXAMPLE 35

(2S)-2-(2,3,4-trifluoroanilino)propionic acid

Methyl 2-(2,3,4-trifluoroanilino)propionate (2.0 g) was suspended in a 0.1 M phosphate buffer solution (pH 6.5; 400 ml). After adding Protease N (manufactured by Amano Seiyaku, originating in a bacterium belonging to the genus *Bacillus*; 0.4 g), the mixture was gently stirred. The mixture was further stirred for 14 hours while maintaining at 30° C. After adding methylene chloride, the liquid reaction mixture was filtered through celite to eliminate denatured protein and then separated. The organic layer was washed with a 5% aqueous solution of sodium hydrogencarbonate and a saturated aqueous solution of sodium chloride and then dried over anhydrous magnesium sulfate. Next, the solvent was evaporated under reduced pressure to thereby give methyl (2R)-2-(2,3,4-trifluoroanilino)propionate (0.94 g). The optical purity of this product was 98% ee. On the other hand, the all aqueous layers obtained by the separation were combined and adjusted to pH 2 with 10% hydrochloric acid followed by extraction with IPE. The organic layer was dried over anhydrous magnesium sulfate and evaporated. Thus, the title compound was obtained as a crude product (0.96 g). The optical purity of this product was 96% ee. Further, the crude product was recrystallized from a solvent mixture of isopropyl ether with hexane. Thus, the title compound of 100% ee was obtained. The $^1$H-NMR and IR spectral data of this product was identical with those of the compound obtained in Example 28.

EXAMPLE 36

(2R)-2-(2,3,4-trifluoroanilino)propionic acid

Methyl 2-(2,3,4-trifluoroanilino)propionate (1.0 g) was suspended in a 0.1 M phosphate buffer solution (pH 6.5; 200 ml). After adding α-chymotrypsin (manufactured by Sigma; 0.2 g), the mixture was gently stirred. The mixture was further stirred for 16 hours while maintaining at 30° C. After adding methylene chloride, the liquid reaction mixture was filtered through celite to eliminate denatured protein and then separated. The organic layer was washed with a 5% aqueous solution of sodium hydrogencarbonate and a saturated aqueous solution of sodium chloride and then dried over anhydrous magnesium sulfate. Next, the solvent was evaporated under reduced pressure to thereby give methyl (2S)-2-(2,3,4-trifluoroanilino)propionate (0.43 g). The optical purity of this product was 98% ee. On the other hand, the all aqueous layers obtained by the separation were combined and adjusted to pH 2 with 10% hydrochloric acid followed by extraction with IPE. The organic layer was dried over anhydrous magnesium sulfate and evaporated. Thus, the title compound was obtained as a crude product (0.47 g). The optical purity of this product was 92% ee. Further, the crude product was recrystallized from a solvent mixture of isopropyl ether with hexane. Thus, the title compound of 100% ee was obtained. The $^1$H-NMR and IR spectral data of this product was identical with those of the compound obtained in Example 29.

EXAMPLES 37 TO 42

Reactions were performed as in Example 36 but using various substrates and catalysts (enzymes and microorganism) subjected to the asymmetric hydrolysis reaction.

TABLE

| Ex. | Substrate | Enzyme | Origin | Reaction rate (%) | Optical purity e.e. (%) Carboxylic acid | Ester |
|---|---|---|---|---|---|---|
| 19 | Methyl ester | Protease | Rhizopus sp. | 47 | 92 (S) | 96 (R) |
| 20 | Methyl ester | Protease | Streptomyces sp. | 53 | 88 (S) | 97 (R) |
| 21 | Ethyl ester | Protease N | Bacillus sp. | 46 | 93 (S) | 99 (R) |
| 22 | Ethyl ester | α-Chymotrypsin | Bovine pancreas | 48 | 86 (R) | 96 (S) |
| 23 | Ethyl ester | Protease | Rhizopus sp. | 52 | 90 (S) | 98 (R) |
| 24 | Ethyl ester | Protease | Streptomyces sp. | 48 | 91 (S) | 97 (R) |

EXAMPLE 43

(2S)-2-(2,3,4-Trifluoroanilino)propionic acid

Microbial cells (IAM-1623; *Bacillus subtilis*) were cultured in a bouillon medium (pH 7.0; 50 ml) at 30° C. for 14 hours. After removing the medium by centrifugation from the culture thus obtained, the cells are freeze-dried to give freeze-dried cells. Methyl 2-(2,3,4-trifluoroanilino) propionate (2.0 g) was suspended in a 0.1 M phosphate buffer solution (pH 6.5; 100 ml). Then the above-described freeze-dried microbial cells (0.2 g) were added thereto and gently stirred. The mixture was stirred for additional 6 hours while maintaining at 30° C. After adding methylene chloride, the liquid reaction mixture was filtered through celite to thereby eliminate denatured protein and then separated. The organic layer was washed with a 5% aqueous solution of sodium hydrogencarbonate and a saturated aqueous solution of sodium chloride and dried over anhydrous magnesium sulfate. Then the solvent was evaporated under reduced pressure to thereby give methyl (2R)-2-(2,3,4-trifluoroanilino)propionic acid (0.92 g). The optical purity of this product was 97% ee. On the other hand, all of the aqueous layers obtained by the separation were combined and adjusted to pH 2 with 10% hydrochloric acid followed by extraction with IPE. The organic layer was dried over anhydrous magnesium sulfate and evaporated to thereby give the title compound as 0.97 g of colorless crystals of a crude product. The optical purity of this product was 96% ee. Further, the crude product was recrystallized from a solvent mixture of isopropyl ether with hexane. Thus, the title compound of 100% ee was obtained. The $^1$H-NMR and IR spectral data of this product was identical with those of the compound obtained in Example 28.

EXAMPLE 44

(2S)-2-(2,3,4-Trifluoroanilino)propionic acid

Microbial cells (IFO-1575; *Zygoascus hellenicus*) were cultured in an MY medium (pH 6.0; 50 ml) at 30° C. for 48 hours. Methyl 2-(2,3,4-trifluoroanilino)propionate (1.0 g) was suspended in a 0.1 M phosphate buffer solution (pH 6.5; 90 ml). Then the above-described liquid culture (10 ml) was added thereto and gently stirred. The mixture was stirred for additional 16 hours while maintaining at 30° C. Then it was treated as in Example 43 to thereby give methyl (2R)-2-(2, 3,4-trifluoroanilino)propionate (0.39 g, optical purity 91% ee) and the title compound (0.45 g, optical purity 84% ee).

When the same asymmetric hydrolysis reaction as the one as described above was performed by using IF08306:*Nannizia gypsea* as the microbial cells, the title compound was obtained at a reaction ratio of 55% (carboxylic acid 80% ee (S), ester 80% ee (R)).

Similarly, the title compound was obtained at a reaction ratio of 42% (carboxylic acid 92% ee (S), ester 60% ee (R)) by using IFO-12883:*Actinomyces leporis*. Also, the title compound was obtained at a reaction ratio of 37% (carboxylic acid 91% ee (S), ester 50% ee (R)) by using NRIC1271:*Penicillium chrysogenum*. The $^1$H-NMR and IR spectral data of each product was identical with those of the compound obtained in Example 28.

EXAMPLE 45

Methyl 2-(2,3,4-trifluoroanilino)propionate

Methyl (2R)-2-(2,3,4-trifluoroanilino)propionate (100 mg, 38% ee) was dissolved in toluene (2 ml) and 1,8-diazabicyclo[5.4.0]undec-7-ene (DBU; 71.8 mg) was added thereto at room temperature. Then the liquid reaction mixture was stirred at 110° C. for 16 hours. After adding hydrochloric acid (1 mol/l; 1 ml) to the liquid reaction mixture, the aqueous layer was extracted with toluene. The organic layer was washed with water and a saturated aqueous solution of sodium chloride and dried over anhydrous magnesium sulfate. After evaporating the solvent, the obtained residue was subjected to silica gel column chromatography (ethyl acetate-normal hexane=1:4) to thereby give the title compound (86.8 mg) as colorless crystals. The optical purity of this product was 0% ee. The $^1$H-NMR and IR spectral data of this product was identical with those of the compound obtained in Example 5.

EXAMPLE 46

Methyl 2-(2,3,4-trifluoroanilino)propionate

Methyl (2R)-2-(2,3,4-trifluoroanilino)propionate (50 mg, 57% ee) was dissolved in N,N-dimethylformamide (DMF; 1 ml) and potassium carbonate (63.2 mg) was added thereto at room temperature. Then the liquid reaction mixture was stirred at 110° C. for 19 hours. After adding water to the liquid reaction mixture, the aqueous layer was extracted with ethyl acetate. The organic layer was washed with water and dried over anhydrous magnesium sulfate. After evaporating the solvent, the obtained residue was subjected to silica gel column chromatography (ethyl acetate-normal hexane=1:4) to thereby give the title compound (42.5 mg) as colorless crystals. The optical purity of this product was 0% ee. The $^1$H-NMR and IR spectral data of this product was identical with those of the compound obtained in Example 5.

EXAMPLE 47

Methyl 2-(2,3,4-trifluoroanilino)propionate

Methyl (2R)-2-(2,3,4-trifluoroanilino)propionate (200 mg, 57% ee) was dissolved in dimethylacetamide (DMAc; 3 ml) and potassium carbonate (474.1 mg) was added thereto at room temperature. Then the liquid reaction mixture was stirred at 95° C. for 19 hours. After adding water to the liquid reaction mixture, the aqueous layer was extracted with ethyl acetate. The organic layer was washed with water and dried over anhydrous magnesium sulfate. After evaporating the solvent, the obtained residue was subjected to silica gel column chromatography (ethyl acetate-normal hexane=1:4) to thereby give the title compound (179 mg) as colorless crystals. The optical purity of this product was 0% ee. The $^1$H-NMR and IR spectral data of this product was identical with those of the compound obtained in Example 5.

EXAMPLE 48

2-(2,3,4-Trifluoroanilino)propionic acid

Potassium tertiary-butoxide (123.4 mg) was suspended in DMAc (2 ml). Under ice-cooling, a solution of methyl (2R)-2-(2,3,4-trifluoroanilino)propionate (223 mg, 91% ee) in DMAc (2 ml) was added thereto. The liquid reaction mixture was stirred at the same temperature for 1 hour. Then an aqueous solution of sodium hydroxide (3 mol/l; 2 ml) was added and the mixture was stirred for 1 hour. The liquid reaction mixture was adjusted to pH 2 with an aqueous solution of hydrochloric acid (3 mol/l) and then extracted with IPE. The organic layer was dried over anhydrous magnesium sulfate and evaporated. The crude product thus obtained was recrystallized from a solvent mixture of methylene chloride with normal hexane to thereby give the title compound (206 mg) as colorless crystals. The optical purity of this product was 0% ee. Various spectral data of this product was identical with those obtained in Example 23.

EXAMPLE 49

2-(2,3,4-Trifluoroanilino)propionic acid

Methyl (2R)-2-(2,3,4-trifluoroanilino)propionate (223 mg, 91% ee) was dissolved in DMAc (3 ml) and potassium carbonate (474.1 mg) was added thereto at room temperature. The liquid reaction mixture was stirred at 95° C. for 19 hours. After adding an aqueous solution of sodium hydroxide (3 mol/l), the liquid reaction mixture was stirred for 1 hour and then adjusted to pH 2 with hydrochloric acid (3 mol/l) followed by extraction with IPE. Next, it was dried over anhydrous magnesium sulfate. After evaporating the solvent, the crude product thus obtained was recrystallized from a solvent mixture of methylene chloride with normal hexane to thereby give the title compound (198 mg) as colorless crystals. The optical purity of this product was 0% ee. Various spectral data of this product was identical with those obtained in Example 23.

EXAMPLE 50

2-(2,3,4-Trifluoroanilino)propionic acid

Potassium carbonate (1.66 g) was suspended in DMAc (18 ml). Then, a solution (5 ml) of methyl (2R)-2-(2,3,4-trifluoroanilino) propionate (2.33 g, 54% ee) in DMAc was added dropped thereinto. The liquid reaction mixture was stirred at the same temperature for 2 hours. Then an aqueous solution of potassium hydroxide (3 mol/l; 2 ml) was added and the mixture was stirred for 15 minutes. The liquid reaction mixture was adjusted top pH 2 with hydrochloric acid (6 mol/l), then extracted with methyl t-butyl ether and dried over anhydrous magnesium sulfate. After evaporating the solvent, the crude product thus obtained was dissolved in ethyl acetate (12 ml) and dropped into a solution (10 ml) of cyclohexylamine (991.8 mg) in ethyl acetate at 60° C. over 30 minutes. Then the liquid reaction mixture was stirred at the same temperature for 2 hours and the 2-(2,3,4-trifluoroanilino)propionic acid cyclohexylamine salt (2.74 g) thus precipitated was collected by filtration.

The data of the 2-(2,3,4-trifluoroanilino)propionic acid-cyclohexylamine salt are as follows.

Elemental analysis as $C_{15}H_{21}F_3N_2O_2$

| | |
|---|---|
| Calculated (%): | C, 56.59; H, 6.65; N, 8.80 |
| Found (%): | C, 56.52; H, 6.67; N, 8.77 |

$^1$H-NMR (270 MHz, CDCl$_3$) δ (ppm): 1.11–2.05 (m, 16H), 2.90–3.13 (m, 1H), 3.73–3.86 (m, 1H), 6.30–6.47 (m, 1H), 6.75–6.89 (m, 1H)

Subsequently, hydrochloric acid (6 mol/l) was added to this cyclohexylamine salt and the mixture was extracted with methyl t-butyl ether (MTBE) and dried over anhydrous magnesium sulfate. After evaporating the solvent, the title compound (1.92 g) was obtained as colorless crystals. Its optical purity was 0% ee.

EXAMPLE 51

(2S)-2-(2,3,4-Trifluoroanilino)-1-propanol

Under ice-cooling, sodium borohydride (1.2 g) was dissolved in IPA (50 ml). After adding methanol (5 ml), a solution of the compound (5.0 g) obtained in Example 1 in IPA was dropped thereinto. Then the liquid reaction mixture was heated to 50° C. and stirred for 1 hour. Next, hydrochloric acid (1 mol/l) was added and the mixture was stirred for a while. Then a saturated aqueous solution of sodium hydrogencarbonate was added and the mixture was extracted with ethyl acetate. The extract was washed with water, dried over anhydrous magnesium sulfate and filtered. After evaporating the solvent, the obtained residue was subjected to silica gel column chromatography to give 3.7 g (84%) of the title compound as an oily substance.

$^1$H-NMR (CDCl$_3$, 270 MHz,) δ: 1.21 (d, J=6.3 Hz, 3H), 1.77 (brs, 1H), 3.55–3.71 (m, 4H), 6.39–6.48 (m, 1H), 6.75–6.87 (m, 1H)

IR: 3394, 2967, 2933 cm$^{-1}$

MS;m/z:205(M$^+$)

EXAMPLE 52

(2S)-2-(2,3,4-Trifluoroanilino)propanol

At room temperature, sodium borohydride (35.7 mg) was suspended in toluene (0.2 ml). Then a solution (0.8 ml) of methyl (2S)-2-(2,3,4-trifluoroanilino)propionate (200 mg, 99.8% ee) in toluene was added to the solution. After adding methanol (137.4 mg), the liquid reaction mixture was stirred for 6 hours. Then water was added to the liquid reaction mixture followed by extraction with ethyl acetate. The organic layer was washed with water and a saturated aqueous solution of ammonium chloride and dried over anhydrous magnesium sulfate. After evaporating, the solvent, the obtained residue was subjected to silica gel column chromatography to thereby give 162.9 mg (99.8% ee) of the title compound as an oily substance. The $^1$H-NMR and IR spectral data of this product was identical with those of the compound obtained in Example 51.

EXAMPLE 53

(2S)-2-(2,3,4-Trifluoroanilino)propanol

At room temperature, sodium borohydride (35.7 mg) was suspended in chlorobenzene (0.2 ml). Then a solution (0.8 ml) of methyl (2S)-2-(2,3,4-trifluoroanilino)propionate (200 mg, 99.8% ee) in chlorobenzene was added to the solution. After adding methanol (137.4 mg), the liquid reaction mixture was stirred for 6 hours. Then water was added to the liquid reaction mixture followed by extraction with ethylacetate. The organic layer was washed with water and a saturated aqueous solution of ammonium chloride and dried over anhydrous magnesium sulfate. After evaporating the solvent, the obtained residue was subjected to silica gel column chromatography to thereby give 162.9 mg (99.8% ee) of the title compound as an oily substance. The $^1$H-NMR and IR spectral data of this product was identical with those of the compound obtained in Example 51.

EXAMPLE 54

(2S)-2-(2,3,4-Trifluoroanilino)propanol

At room temperature, sodium borohydride (35.7 mg) was suspended in hexane (0.2 ml). Then a solution (0.8 ml) of methyl (2S)-2-(2,3,4-trifluoroanilino)propionate (200 mg, 99.8% ee) in hexane was added to the solution. After adding methanol (137.4 mg), the liquid reaction mixture was stirred for 1 hour. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 176 mg (99.8% ee) of the title compound as an oily substance. The $^1$H-NMR and IR spectral data of this product was identical with those of the compound obtained in Example 51.

EXAMPLE 55

(2S)-2-(2,3,4-Trifluoroanilino)propanol

At room temperature, sodium borohydride (35.7 mg) was suspended in cyclohexane (0.2 ml). Then a solution (0.8 ml) of methyl (2S)-2-(2,3,4-trifluoroanilino)propionate (200 mg, 99.8% ee) in cyclohexane was added to the solution. After adding methanol (137.4 mg), the liquid reaction mixture was stirred for 6 hours. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 176 mg (99.8% ee) of the title compound as an oily substance. The $^1$H-NMR and IR spectral data of this product was identical with those of the compound obtained in Example 51.

EXAMPLE 56

(2S)-2-(2,3,4-Trifluoroanilino)propanol

At room temperature, sodium borohydride (35.7 mg) was suspended in IPE (0.2 ml). Then a solution (0.8 ml) of methyl (2S)-2-(2,3,4-trifluoroanilino)propionate (200 mg, 99.8% ee) in IPE was added to the solution. After adding methanol (137.4 mg), the liquid reaction mixture was stirred for 2 hours. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 176 mg (99.8% ee) of the title compound as an oily substance. The $^1$H-NMR and IR spectral data of this product was identical with those of the compound obtained in Example 51.

EXAMPLE 57

(2S)-2-(2,3,4-Trifluoroanilino)propanol

At room temperature, sodium borohydride (35.7 mg) was suspended in methyl t-butyl ether (0.2 ml). Then a solution (0.8 ml) of methyl (2S)-2-(2,3,4-trifluoroanilino)propionate (200 mg, 99.8% ee) in methyl t-butyl ether was added to the solution. After adding methanol (137.4 mg), the liquid reaction mixture was stirred for 1 hour. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 176 mg (99.8% ee) of the title compound as an oily substance. The $^1$H-NMR and IR spectral data of this product was identical with those of the compound obtained in Example 51.

EXAMPLE 58

(2S)-2-(2,3,4-Trifluoroanilino)propanol

At room temperature, sodium borohydride (35.7 mg) was suspended in THF (0.2 ml). Then a solution (0.8 ml) of methyl (2S)-2-(2,3,4-trifluoroanilino)propionate (200 mg, 99.8% ee) in THF was added to the solution. After adding methanol (137.4 mg), the liquid reaction mixture was stirred for 1 hour. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 176 mg (99.8% ee) of the title compound as an oily substance. The $^1$H-NMR and IR spectral data of this product was identical with those of the compound obtained in Example 51.

EXAMPLE 59

(2S)-2-(2,3,4-Trifluoroanilino)propanol

At room temperature, sodium borohydride (35.7 mg) was suspended in 1,2-dimethoxyethane (0.2 ml). Then a solution (0.8 ml) of methyl (2S)-2-(2,3,4-trifluoroanilino)propionate (200 mg, 99.8% ee) in DME was added to the solution. After adding methanol (137.4 mg), the liquid reaction mixture was stirred for 1 hour. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 176 mg (99.8% ee) of the title compound as an oily substance. The $^1$H-NMR and IR spectral data of this product was identical with those of the compound obtained in Example 51.

EXAMPLE 60

(2S)-2-(2,3,4-Trifluoroanilino)propanol

At room temperature, sodium borohydride (35.7 mg) was suspended in chloroform (0.2 ml). Then a solution (0.8 ml) of methyl (2S)-2-(2,3,4-trifluoroanilino)propionate (200 mg, 99.8% ee) in chloroform was added to the solution. After adding methanol (137.4 mg), the liquid reaction mixture was stirred for 6 hours. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 137.3 mg (99.8% ee) of the title compound as an oily substance. The $^1$H-NMR and IR spectral data of this product was identical with those of the compound obtained in Example 51.

EXAMPLE 61

(2S)-2-(2,3,4-Trifluoroanilino)propanol

At room temperature, sodium borohydride (35.7 mg) was suspended in methylene chloride (0.2 ml). Then a solution (0.8 ml) of methyl (2S)-2-(2,3,4-trifluoroanilino)propionate (200 mg, 99.8% ee) in metylene chloride was added to the solution. After adding methanol (137.4 mg), the liquid reaction mixture was stirred for 1 hour. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 159.8 mg (99.8% ee) of the title compound as an oily substance. The $^1$H-NMR and IR spectral data of this product was identical with those of the compound obtained in Example 51.

EXAMPLE 62

(2S)-2-(2,3,4-Trifluoroanilino)propanol

At room temperature, sodium borohydride (35.7 mg) was suspended in 1,2-dichloroethane (EDC, 0.2 ml). Then a solution (0.8 ml) of methyl (2S)-2-(2,3,4-trifluoroanilino)propionate (200 mg, 99.8% ee) in EDC was added to the solution. After adding methanol (137.4 mg), the liquid reaction mixture was stirred for 1 hour. Then water was added to the liquid reaction mixture followed by extraction with ethyl acetate. The organic layer was washed with water and a saturated aqueous solution of ammonium chloride and dried over anhydrous magnesium sulfate. After evaporating the solvent, the obtained residue was subjected to silica gel column chromatography to thereby give 159.8 mg (99.8% ee) of the title compound as an oily substance. The $^1$H-NMR and IR spectral data of this product was identical with those of the compound obtained in Example 51.

EXAMPLE 63

Diethyl [2,3,4-trifluoro[(1S)-2-hydroxy-1-methylethyl]anilino]methylenamalonate

The compound (300 mg) obtained in Example 51, diethyl ethoxymethylenemalonate (632 mg) and tetrahexylammonium chloride (57 mg) were dissolved in acetone (3 ml). After adding potassium carbonate (445 mg), the mixture was stirred at room temperature for 4.5 hours. After the completion of the reaction, the solvent was evaporated. Then the residue thus obtained was subjected to silica gel column chromatography to thereby give 338 mg (84%) of the title compound as a colorless solid.

$^1$H-NMR (CDCl$_3$, 270 MHz) δ: 1.13 (t, J=7.26 Hz, 3H), 1.23 (t, J=7.26 Hz, 3H), 2.34 (brs, 1H), 3.62–3.81 (m, 5H), 4.16 (q, J=7.26 Hz, 2H), 6.87–7.11 (m, 2H), 7.70 (s, 1H)

IR (KBr): 3451, 3093, 2989, 1706, 1678 cm$^{-1}$

MS;m/z: 375(M$^+$)

EXAMPLE 64

Diethyl [2,3,4-trifluoro[(1S)-2-hydroxy-1-methylethyl]anilino]methylenemalonate

The compound (103 mg) obtained in Example 51, diethyl ethoxymethylenemalonate (108 mg) and tetrahexylammonium chloride (29 mg) were dissolved in dichloromethane (1 ml). After adding potassium carbonate (138 mg), the mixture was stirred at room temperature for 22 hours. After the completion of the reaction, the residue was filtered off and the solvent was evaporated. Then the residue thus obtained was subjected to silica gel column chromatography to thereby give 147 mg (78%) of the title compound as a colorless solid. The $^1$H-NMR and IR spectral data of this product was identical with those of the compound obtained in Example 63.

EXAMPLE 65

Diethyl [2,3,4-trifluoro[(1S)-2-hydroxy-1-methylethyl]anilino]methylenemalonate

Potassium tertiary-butoxide (62 mg) was added to DMF (2 ml) and cooled to 0° C. Then a solution of the compound (100 mg) obtained in Example 51 in DMF (200 μl) was dropped thereinto. After stirring for 15 minutes, diethyl ethoxymethylenemalonate was dropped thereinto and the resultant mixture was stirred for 8 hours at room temperature. After treating in a conventional manner, it was subjected to silica gel column chromatography to thereby give 137 mg (75%) of the title compound as a colorless solid. The $^1$H-NMR and IR spectral data of this product was identical with those of the compound obtained in Example 63.

EXAMPLE 66

Diethyl [2,3,4-trifluoro[(1S)-2-hydroxy-1-methylethyl]anilino]methylenemalonate

To the compound (103 mg) obtained in Example 51 was added diethyl ethoxymethylenemalonate (127 mg). Then the obtained mixture was stirred for 1 hour while heating to 100° C. under atmospheric pressure. Further, it was stirred at the same temperature for 1.5 hour under reduced pressure and then under atmospheric pressure for additional 16 hours. By analyzing reversed phase HPLC with the use of the compound of Example 63 as a specimen, the obtained product corresponded to 142 mg (78%) of the title compound.

EXAMPLE 67

Diethyl [2,3,4-trifluoro[(1S)-2-hydroxy-1-methylethyl]anilino]methylenemalonate

The compound (103 mg) obtained in Example 51 and dimethyl ethoxymethylenemalonate (87 mg) were dissolved in toluene (3 ml) and the mixture was heated under reflux for 21 hours. Then the residue was filtered off and the solvent was evaporated. The obtained residue was subjected to silica gel column chromatography to give 125 mg (72%) of the title compound as colorless crystals.

$^1$H-NMR (CDCl$_3$, 270 MHz) δ: 1.22–1.25 (m, 3H), 3.27 (s, 1H), 3.57–3.82 (m, 8H), 6.96–7.10 (m, 2H), 7.76 (s, 1H)

IR (KBr): 3452, 2954, 1722 cm$^{-1}$

MS;m/z: 347(M$^+$), 316, 284

EXAMPLE 68

Diethyl [2,3,4-trifluoro[(1S)-2-hydroxy-1-methylethyl]anilino]methylenemalonate

At room temperature, potassium hydroxide (330 mg) and tetrahexylammonium chloride (190.1 mg) were dissolved in DMF (15 ml). After adding a solution (5 ml) of (2S)-2-(2,3,4-trifluoroanilino)propanol (1 g, 99.8% ee) and diethyl ethoxymethylenemalonate (2.09g) in DMF, the resultant mixture was stirred for 1 hour. After adding water, the liquid reaction mixture was extracted with a solvent mixture of ethyl acetate and n-hexane (3:2). The organic layer was washed with water and dried over anhydrous magnesium sulfate. After evaporating the solvent, IPE was added to the obtained residue and the mixture was stirred at 0° C. for 1 hour. The crystals thus precipitated were collected by filtration and the moist product thus obtained was dried under reduced pressure. Thus, the title compound (1.65 g, 99.8% ee) was obtained as colorless crystals. The $^1$H-NMR and IR spectral data of this product was identical with those of the compound obtained in Example 63.

EXAMPLE 69

Diethyl [2,3,4-trifluoro[(1S)-2-hydroxy-1-methylethyl]anilino]methylenemalonate

At room temperature, potassium hydroxide (330 mg) and tetrabutylammonium hydrogensulfate (82.7 mg) were dissolved in DMF (15 ml). After adding a solution (5 ml) of (2S)-2-(2,3,4-trifluoroanilino)propanol (1 g, 99.8% ee) and diethyl ethoxymethylenemalonate (2.09g) in DMF, the resultant mixture was stirred for 1 hour. After adding water, the liquid reaction mixture was extracted with a solvent mixture of ethyl acetate and n-hexane (3:2). The organic layer was washed with water and dried over anhydrous magnesium sulfate. After evaporating the solvent, IPE was added to the obtained residue and the mixture was stirred at 0° C. for 1 hour. The crystals thus precipitated were collected by filtration and the moist product thus obtained was dried under reduced pressure. Thus, the title compound (1.7 g, 99.8% ee) was obtained as colorless crystals. The $^1$H-NMR and IR spectral data of this product was identical with those of the compound obtained in Example 63.

EXAMPLE 70

Diethyl [2,3,4-trifluoro[(1S)-2-hydroxy-1-methylethyl]anilino]methylenemalonate

At room temperature, potassium hydroxide (330 mg) and tetrabutylammonium hydrogensulfate (82.7 mg) were dissolved in DMF (15 ml). After adding a solution (5 ml) of (2S)-2-(2,3,4-trifluoroanilino)propanol (1 g, 99.8% ee) and diethyl ethoxymethylenemalonate (2.09 g) in DMF, the resultant mixture was stirred for 1 hour. After adding water, the liquid reaction mixture was extracted with a solvent mixture of ethyl acetate and n-hexane (3:2). The organic layer was washed with water and dried over anhydrous magnesium sulfate. After evaporating the solvent, IPE was added to the obtained residue and the mixture was stirred at 0° C. for 1 hour. The crystals thus precipitated were collected by filtration and the moist product thus obtained was dried under reduced pressure. Thus, the title compound (1.65 g, 99.8% ee) was obtained as colorless crystals. The $^1$H-NMR and IR spectral data of this product was identical with those of the compound obtained in Example 63.

EXAMPLE 71

Diethyl [(3S)-7,8-difluoro-3-methyl-2,3-dihydro-4H-[1,4]benzoxazin-4-yl]methylenemalonate To DMF (5 ml) was added potassium tertiary-butoxide (74 mg) under ice-cooling. After dropping a solution of the compound (200 mg) obtained in Example 63 in DMF (1 ml), the resultant mixture was stirred at 60° C. for 18 hours. After treating in a conventional manner, the obtained residue was subjected to silica gel column chromatography to thereby give 149 mg (79%) of the title compound. The physical constants of the obtained compounds was identical with those described in Japanese Patent No. 2,769,174.

EXAMPLE 72

Diethyl [(3S)-7,8-difluoro-3-methyl-2,3-dihydro-4H-[1,4]benzoxazin-4-yl]methylenemalonate To DMF (2 ml) was added potassium tertiary-butoxide (226 mg) under ice-cooling. After dropping a solution of the compound (100 mg) obtained in Example 51 and diethyl ethoxymethylenemalonate (293 mg) in DMF (0.5 ml), the resultant mixture was stirred at room temperature for 18 hours. After treating in a conventional manner, the obtained residue was subjected to silica gel column chromatography to thereby give 113 mg (65%) of the title compound. The physical constants of the obtained compounds was identical with those described in Japanese Patent No. 2,769,174.

EXAMPLE 73

Diethyl [(3S)-7,8-difluoro-3,4-dihydro-3-methyl-2H-[1,4]benzoxazin-4-yl]methylenemalonate Potassium hydroxide (180 mg) and tetrabutylammonium hydrogensulfate (90.4 mg) were dissolved in DMF (15 ml) by heating to 60° C. and a solution of diethyl [2,3,4-trifluoro [(1S)-2-hydroxy-1-methylethyl]anilino]methylenemalonate (1 g, 99.8% ee) and diethyl ethoxymethylenemalonate (120 mg) in DMF 85 ml) was added thereto. The obtained mixture was stirred at the same temperature for 2 hours. After adding water, the liquid reaction mixture was extracted with ethyl acetate. The organic layer was dried over anhydrous magnesium sulfate. After evaporating the solvent, the obtained residue was subjected to silica gel column chromatography. Thus, 852 mg (99.8% ee) of the title compound was obtained as a yellow oily substance. Various spectral data was identical with those described in Japanese Patent No. 2,769,174.

EXAMPLE 74

Diethyl [(3S)-7,8-difluoro-3,4-dihydro-3-methyl-2H-[1,4]benzoxazin-4-yl]methylenemalonate Potassium hydroxide (180 mg) and benzyltrimethylammonium chloride (49.5 mg) were dissolved in DMF (15 ml) by heating to 70° C. and a solution of diethyl [2,3,4-trifluoro [(1S)-2-hydroxy-1-methylethyl]anilino]methylenemalonate (1 g, 99.8% ee) and diethyl ethoxymethylenemalonate (120 mg) in DMF (5 ml) was added thereto. The obtained mixture was stirred at the same temperature for 4 hours. After adding water, the liquid reaction mixture was extracted with ethyl acetate. The organic layer was dried over anhydrous magnesium sulfate. After evaporating the solvent, the obtained residue was subjected to silica gel column chromatography. Thus, 871 mg (99.8% ee) of the title compound was obtained as a yellow oily substance. Various spectral data was identical with those described in Japanese Patent No. 2,769,174.

EXAMPLE 75

Diethyl [(3S)-7,8-difluoro-3,4-dihydro-3-methyl-2H-[1,4]benzoxazin-4-yl]methylenemalonate Potassium hydroxide (180 mg) and benzyltrimethylammonium chloride (60.7 mg) were dissolved in DMF (15 ml) by heating to 60° C. and a solution (5 ml) of diethyl [2,3,4-trifluoro[(1S)-2-hydroxy-1-methylethyl]anilino]methylenemalonate (1 g, 99.8% ee) and diethyl ethoxymethylenemalonate (120 mg) in DMF was added thereto. The obtained mixture was stirred at the same temperature for 7 hours. After adding water, the liquid reaction mixture was extracted with ethylacetate. The organic layer was dried over anhydrous magnesium sulfate. After evaporating the solvent, the obtained residue was subjected to silica gel column chromatography. Thus, 899 mg (99.8% ee) of the title compound was obtained as a yellow oily substance. Various spectral data was identical with those described in Japanese Patent No. 2,769,174.

EXAMPLE 76

Diethyl [(3S)-7,8-difluoro-3,4-dihydro-3-methyl-2H-[1,4]benzoxazin-4-yl]methylenemalonate At room temperature, KOH (330 mg) and tetrahexylammonium chloride (190.1 mg) were dissolved in DMF (15 ml). After adding a solution (5 ml) of (2S)-2-(2,3,4-trifluoroanilino)propanol (1 g, 99.8% ee) and diethyl ethoxymethylenemalonate (2.09 g) in DMF, the mixture was stirred for 1 hour. Next, it was heated to 60° C. and a solution (5 ml) of KOH (330 mg) and diethyl ethoxymethylenemalonate (120 mg) in DMF was added thereto. The resultant mixture was stirred at the same temperature for 5 hours. After adding water, the liquid reaction mixture was extracted with ethyl acetate. The organic layer was dried over anhydrous magnesium sulfate. After evaporating the solvent, the obtained residue was subjected to silica gel column chromatography. Thus, 1.37 g (99.8% ee) of the title compound was obtained as a yellow oily substance. Various spectral data was identical with those described in Japanese Patent No. 2,769,174.

EXAMPLE 77

Diethyl [(3S)-7,8-difluoro-3,4-dihydro-3-methyl-2H-[1,4]benzoxazin-4-yl]methylenemalonate At room temperature, KOH (330 mg) and tetrabutylammonium hydrogensulfate (82.7 mg) were dissolved in DMF (15 ml). After adding a solution (5 ml) of (2S)-2-(2,3,4-trifluoroanilino)propanol (1 g, 99.8% ee) and diethyl ethoxymethylenemalonate (2.09 g) in DMF, the mixture was stirred for 1 hour. Next, it was heated to 60° C. and a solution (5 ml) of KOH (330 mg) and diethyl ethoxymethylenemalonate (120 mg) in DMF was added thereto. The resultant mixture was stirred at the same temperature for 5 hours. After adding water, the liquid reaction mixture was extracted with ethyl acetate. The organic layer was dried over anhydrous magnesium sulfate. After evaporating the solvent, the obtained residue was subjected to silica gel column chromatography. Thus, 1.3 g (99.8% ee) of the title compound was obtained as a yellow oily substance. Various spectral data was identical with those described in Japanese Patent No. 2,769,174.

EXAMPLE 78

(3S)-(+)-7,8-Difluoro-3,4-dihydro-3-methyl-2H-[1,4]benzoxazine

To DMF (2 ml) was added sodium hydride (39 mg) and the mixture was heated to 60° C. in an oil bath. Next, a solution of the compound (100 mg) obtained in Example 51 in DMF was dropped thereinto and the obtained mixture was stirred for 1 hour. After treating in a conventional manner, the mixture was subjected to silica gel column chromatography to give 60 mg (66%) of the title compound. The optical purity determined by HPCL was >94% ee. Various spectral data was identical with those of a specimen synthesized separately.

EXAMPLE 79

(3S)-(+)-7,8-Difluoro-3,4-dihydro-3-methyl-2H-[1,4]benzoxazine

To DMF (2 ml) was added potassium tertiary-butoxide (110 mg) under ice-cooling. Next, a solution of the compound (100 mg) obtained in Example 51 in DMF was dropped thereinto and the obtained mixture was stirred for 30 minutes. After treating in a conventional manner, the mixture was subjected to silica gel column chromatography to give 72 mg (79%) of the title compound. The optical purity determined by HPCL was >94% ee. Various spectral data was identical with those of a specimen synthesized separately.

EXAMPLE 80

(3S)-7,8-Difluoro-3-methyl-3,4-dihydro-2H-[1,4]benzoxazine•p-toluenesulfonate

To sodium tertiary-butoxide (t-BuONa; 748 mg) was added DMAc (8 ml). After dissolving by heating at 80° C., a solution of (2S)-2-(2,3,4-trifluoroanilino)propanol (1.0 g; 99.8% ee) in DMAc (2 ml) was added thereto at the same temperature. After stirring for 30 minutes and cooling by allowing to stand, water (30 ml) was added at room temperature. The resultant mixture was extracted with ethyl acetate (AcOEt; 20 ml) thrice. The organic layer thus extracted was concentrated under reduced pressure. The obtained solution was dropped into a solution of p-toluenesulfonic acid monohydrate (927.5 mg) in AcOEt (10 ml). After stirring at room temperature for additional 1 hour, crystals were collected by filtration while washing with AcOEt (7 ml). The moist product thus obtained was dried under reduced pressure to give the title compound (1.6 g) as colorless crystals.

$^1$H-NMR (CD$_3$OD) δ: 1.43 (d, 3H, J=5.7 Hz), 2.34 (d, 3H, J=12.2 Hz), 3.85–3.89 (m, 1H), 4.09–4.17 (m, 1H), 7.22–7.32 (m, 1H), 6.77–6.89 (m, 1H)

Melting point: 131 to 133° C. (decomposition)

Elemental analysis as C$_{16}$H$_{17}$NO$_4$S

| | |
|---|---|
| Calculated (%): | C, 53.77; H, 4.79; N, 3.92% |
| Found (%): | C, 53.80; H, 4.81; N, 3.86% |

EXAMPLE 81

(3S)-7,8-Difluoro-3-methyl-3,4-dihydro-2H-[1,4]benzoxazine p-toluenesulfonate

To potassium tertiary-butoxide (t-BuOK; 1.24 g) was added DMF (18 ml). After dissolving by heating at 80° C., a solution of (2S)-2-(2,3,4-trifluoroanilino)propanol (1.0 g; 99.8% ee) in DMF (2 ml) was added thereto at the same temperature. After stirring for 30 minutes and cooling by allowing to stand, water (40 ml) was added at room temperature. The resultant mixture was extracted with AcOEt (20 ml) thrice. The organic layer thus extracted was concentrated under reduced pressure. The obtained solution was dropped into a solution of p-toluenesulfonic acid monohydrate (927.5 mg) in AcOEt (10 ml). After stirring at room temperature for additional 1 hour, crystals were collected by filtration while washing with AcOEt (7 ml). The crystals thus obtained were dried under reduced pressure to give the title compound (1.39 g) as colorless crystals. Various spectral data was identical with those obtained in Example 80.

EXAMPLE 82

(3S)-7,8-Difluoro-3-methyl-3,4-dihydro-2H-[1,4]benzoxazine•p-toluenesulfonate

To sodium hydride (NaH; 262 mg) was added DMF (18 ml). After dissolving by heating at 80° C., a solution of (2S)-2-(2,3,4-trifluoroanilino)propanol (1.0 g; 99.8% ee) in DMF (2 ml) was added thereto at the same temperature. After stirring for 30 minutes and cooling by allowing to stand, water (40 ml) was added at room temperature. The resultant mixture was extracted with AcOEt (20 ml) thrice. The organic layer thus extracted was concentrated under reduced pressure. The obtained solution was dropped into a solution of p-toluenesulfonic acid monohydrate (927.5 mg) in AcOEt (10 ml). After stirring at room temperature for additional 1 hour, crystals were collected by filtration while washing with AcOEt (7 ml). The crystals thus obtained were dried under reduced pressure to give the title compound (1.14 g) as colorless crystals. Various spectral data was identical with those obtained in Example 80.

EXAMPLE 83

(3S)-7,8-Difluoro-3-methyl-3,4-dihydro-2H-[1,4]benzoxazine (3S)-7,8-Difluoro-3-methyl-3,4-dihydro-2H-[1,4]benzoxazine•p-toluenesulfonate (1 g) was suspended in AcOEt (10 ml) and then an aqueous solution of sodium hdyrogencarbonate (NaHCO$_3$; 10 ml) was added thereto. After stirring at room temperature for 1 hour, the mixture was extracted with AcOEt. The organic layer was dried over anhydrous magnesium sulfate and concentrated under reduced pressure to thereby give the title compound (516 mg, 99.8% ee) as a yellow oily substance.

$^1$H-NMR (270 MHz, CDCl$_3$) δ: 2.16 (s, 3H), 4.60 (s, 2H), 6.28 (ddd, 1H, J=2.3, 4.7, 8.9 Hz), 6.50–6.80 (m, 1H)

EXAMPLE 84

(3S)-7,8-Difluoro-3-methyl-3,4-dihydro-2H-[1,4]benzoxazine•methanesulfonate

To t-BuONa (748 mg) was added DMAc (8 ml). After dissolving by heating to 80° C., a solution of (2S)-2-(2,3,4-trifluoroanilino)propanol (1.0 g, 99.8% ee) in DMAc (2 ml) was added thereto at the same temperature. After stirring for 30 minutes and cooling by allowing to stand, water (30 ml) was added thereto at room temperature. The resultant mixture was extracted with AcOEt (20 ml) thrice. The organic layers were combined and concentrated under reduced pressure. The obtained solution was added to a solution of methanesulfonic acid (468.4 mg) in AcOEt (5 ml). After stirring for additional 1 hour at room temperature, crystals were collected by filtration while washing with AcOEt (5 ml). The moist product thus obtained was dried to give the title compound (960.4 mg) as colorless crystals.

$^1$H-NMR (270 MHz, CD$_3$OD) δ: 1.45 (d, 3H, J=6.8 Hz), 2.68 (s, 3H), 3.89–3.93 (m, 1H), 4.17 (dd, 1H, J=8.9, 12.2 Hz)), 4.57 (dd, 1H, J=2.7, 11.9 Hz), 6.96–7.15 (m, 2H)

Melting point: 131 to 133° C. (decomposition)

Elemental analysis as C$_{10}$H$_{13}$F$_2$NO$_4$S

| Calculated (%): | C, 42.70; H, 4.66%; N, 4.98% |
|---|---|
| Found (%): | C, 42.70; H, 4.66%; N, 4.92% |

EXAMPLE 85

(3S)-7,8-Difluoro-3-methyl-3,4-dihydro-2H-[1,4]
benzoxazine-methanesulfonate

To t-BuOK (1.24 g) was added DMF (18 ml). After dissolving by heating at 80° C., a solution of (2S)-2-(2,3,4-trifluoroanilino)propanol (1.0 g; 99.8% ee) in DMF (2 ml) was added thereto at the same temperature. After stirring for 30 minutes and cooling by allowing to stand, water (30 ml) was added at room temperature. The resultant mixture was extracted with AcOEt (20 ml) thrice. The organic layers were combined and concentrated under reduced pressure. The obtained solution was dropped into a solution of methanesulfonic acid (468.4 mg) in AcOEt (5 ml). After stirring at room temperature for additional 1 hour, crystals were collected by filtration while washing with AcOEt (5 ml). The moist product thus obtained was dried under reduced pressure to give the title compound (875 mg) as colorless crystals. Various spectral data was identical with those obtained in Example 84.

EXAMPLE 86

(3S)-7,8-Difluoro-3-methyl-3,4-dihydro-2H-[1,4]
benzoxazine•methanesulfonate

To NaH (262 mg) was added DMF (18 ml). After dissolving by heating at 80° C., a solution of (2S)-2-(2,3,4-trifluoroanilino)propanol (1.0 g; 99.8% ee) in DMF (2 ml) was added thereto at the same temperature. After stirring for 30 minutes and cooling by allowing to stand, water (30 ml) was added at room temperature. The resultant mixture was extracted with AcOEt (20 ml) thrice. The organic layers were combined and concentrated under reduced pressure. The obtained solution was dropped into a solution of methanesulfonic acid (468.4 mg) in AcOEt (5 ml). After stirring at room temperature for additional 1 hour, crystals were collected by filtration while washing with AcOEt (5 ml). The moist product thus obtained was dried under reduced pressure to give the title compound (894 mg) as colorless crystals. Various spectral data was identical with those obtained in Example 84.

EXAMPLE 87

(3S)-7,8-Difluoro-3-methyl-3,4-dihydro-2H-[1,4]
benzoxazine (3S)-7,8-Difluoro-3-methyl-3,4-dihydro-2H-[1,4]benzoxazine•p-toluenesulfonate (1 g) was suspended in AcOEt (10 ml) and then an aqueous solution of $NaHCO_3$ (10 ml) was added thereto. After stirring at room temperature for 1 hour, the mixture was extracted with AcOEt. The organic layer was dried over anhydrous magnesium sulfate and concentrated under reduced pressure to thereby give the title compound (645.2 mg, 99.9% ee) as a yellow oily substance. Various spectral data was identical with those obtained in Example 83.

EXAMPLE 88

(3S)-7,8-Difluoro-3-methyl-3,4-dihydro-2H-[1,4]
benzoxazine•(±)-camphorsulfonate To t-BuONa (748 mg) was added DMAc (8 ml). After dissolving by heating at 80° C., a solution of (2S)-2-(2,3,4-trifluoroanilino)propanol (1.0 g; 99.8% ee) in DMAc (2 ml) was added thereto at the same temperature. After stirring for 30 minutes and cooling by allowing to stand, water (30 ml) was added at room temperature. The resultant mixture was extracted with AcOEt (20 ml) thrice. The organic layers were combined and concentrated under reduced pressure. The obtained solution was dropped into a solution of (±)-camphorsulfonic acid (1.137 g) in 5% EtOH (ethanol)/AcOEt (7 ml). After stirring at room temperature for additional 1 hour, crystals were collected by filtration while washing with AcOEt (7 ml). The moist product thus obtained was dried under reduced pressure to give the title compound (1.8 g) as colorless crystals.

$^1$H-NMR (270 MHz, $CD_3OD$): 0.613 (s, 3H)), 0.847 (s, 3H), 1.36–1.46 (m, 1H), 1.45 (d, 3H, J=6.5 Hz), 1.55–1.65 (m, 1H), 1.88 (d, 1H, J=18.4 Hz), 1.98–2.06 (m, 2H), 2.76 (d, 1H, J=14.6 Hz), 3.27 (d, 1H, J=14.6 Hz), 3.85–3.97 (m, 1H), 4.18 (dd, 1H, J=8.6, 12.2 Hz), 4.57 (dd, 1H, J=2.7, 11.9 Hz), 6.49–7.19 (m, 2H)

Melting point: 232 to 236° C. (decomposition)

Elemental analysis as $C_{19}H_{25}NO_5S$

| Calculated (%): | C, 54.66; H, 6.04; N, 3.36% |
|---|---|
| Found (%): | C, 54.63; H, 6.04; N, 3.29% |

EXAMPLE 89

(3S)-7,8-Difluoro-3-methyl-3,4-dihydro-2H-[1,4]
benzoxazine•(±)-camphorsulfonate To t-BuOK (1.24 g) was added DMF (18 ml). After dissolving by heating at 80° C., a solution of (2S)-2-(2,3,4-trifluoroanilino)propanol (1.0 g; 99.8% ee) in DMF (2 ml) was added thereto at the same temperature. After stirring for 30 minutes and cooling by allowing to stand, water (30 ml) was added at room temperature. The resultant mixture was extracted with AcOEt (20 ml) thrice. The organic layers were combined and concentrated under reduced pressure. The obtained solution was dropped into a solution of (±)-camphorsulfonic acid (1.137 g) in 5% EtOH/AcOEt (7 ml). After stirring at room temperature for additional 1 hour, crystals were collected by filtration while washing with AcOEt (7 ml). The moist product thus obtained was dried under reduced pressure to give the title compound (1.72 g) as colorless crystals. Various spectral data was identical with those obtained in Example 88.

EXAMPLE 90

(3S)-7,8-Difluoro-3-methyl-3,4-dihydro-2H-[1,4]
benzoxazine•(±)-camphorsulfonate To NaH (242 mg) was added DMF (18 ml). After dissolving by heating at 80° C., a solution of (2S)-2-(2,3,4-trifluoroanilino)propanol (1.0 g; 99.8% ee) in DMF (2 ml) was added thereto at the same temperature. After stirring for 30 minutes and cooling by allowing to stand, water (30 ml) was added at room temperature. The resultant mixture was extracted with AcOEt (20 ml) thrice. The organic layer thus extracted was concentrated under reduced pressure. The obtained solution was dropped into a solution of (±)-camphorsulfonic acid (1.137 g) in 5% EtOH/AcOEt (7 ml). After stirring at room temperature for additional 1 hour, crystals were collected by filtration while washing with AcOEt (7 ml). The moist product thus obtained was dried under reduced pressure to give the title compound (1.41 g) as colorless crystals. Various spectral data was identical with those obtained in Example 88.

EXAMPLE 91

(3S)-7,8-Difluoro-3-methyl-3,4-dihydro-2H-[1,4]
benzoxazine (3S)-7,8-Difluoro-3-methyl-3,4-dihydro-2H-[1,4]
benzoxazine•p-toluenesulfonate (1 g) was suspended in AcOEt (10 ml) and then an aqueous solution of NaHCO$_3$ (10 ml) was added thereto. After stirring at room temperature for 1 hour, the mixture was extracted with AcOEt. The organic layer was dried over anhydrous magnesium sulfate and concentrated under reduced pressure to thereby give the title compound (438.9 mg, 99.8% ee) as a yellow oily substance. Various spectral data was identical with those obtained in Example 83.

EXAMPLE 92

Diethyl [(3S)-7,8-difluoro-3-methyl-2,3-dihydro-
4H-[1,4]benzoxazin-4-yl]methylenemalonate To DMF (2.5 ml) was added potassium tertiary-butoxide (75 mg) under ice-cooling. After dropping a solution of the compound (100 mg) obtained in Example 78 and diethyl ethoxymethylenemalonate (233 mg) in DMF (0.5 ml), the resultant mixture was stirred for 2 hours. After treating in a conventional manner, the obtained residue was subjected to silica gel column chromatography to thereby give 153 mg (88%) of the title compound as an oily product. The physical constants of the obtained compounds was identical with those described in Japanese Patent No. 2,769,174.

EXAMPLE 93

Diethyl [(3S)-7,8-difluoro-3-methyl-2,3-dihydro-
4H-[1,4]benzoxazin-4-yl]methylenemalonate 1.20 g (99.8% ee) of (3S)-7,8-difluoro-3-methyl-3,4-dihydro-2H-[1,4]benzoxazine was dissolved in toluene (0.5 ml). After adding diethyl ethoxymethylenemalonate (1.92 g), the mixture was stirred at 120 for 30 minutes and then at 140° C. under reduced pressure for 30 minutes. The residue was subjected to silica gel column chromatography. Thus, 2.19 g (99.8% ee) of the title compound was obtained as a yellow oily product. The physical constants of the obtained compounds was identical with those described in Japanese Patent No. 2,769,174.

EXAMPLE 94

2-(2,3,4-Trifluoroanilino)propyl 4-nitrobenzoate

2-Hydroxypropyl 4-nitrobenzoate (225 mg) was dissolved in dichloromethane (1 ml) by stirring. At −50° C., a solution of trifluoromethanesulfonic anhydride (339 mg) dissolved in dichloromethane (1 ml) was added thereto. After stirring at the same temperature for 30 minutes, dichloromethane was evaporated under reduced pressure at 0° C. After dissolving the residue in dichloromethane (1 ml), a solution of 2,3,4-trifluoroaniline (147.1 mg) dissolved in dichloromethane (1 ml) was dropped thereinto at 0° C. and the resultant mixture was stirred at the same temperature for 30 minutes. Next, dichloromethane (10 ml) was added to the solution followed by washing with water (10 ml). The dichloromethane layer was concentrated under reduced pressure and the obtained residue was separated and purified by silica gel column chromatography to thereby give 159.4 mg (45%) of the title compound as yellow crystals.

$^1$H-NMR (270 MHz, CDCl$_3$) δ: 1.38 (d, 6.6 Hz, 3H), 3.76–3.92 (m, 2H), 4.30 (dd, J=5.3, 11.2 Hz, 1H), 4.49 (dd, J=5.3, 11.2 Hz, 1H), 6.46–6.55 (m, 1H), 6.77–6.88 (m, 1H), 8.17 (dd, J=2.0, 6.9 Hz, 2H), 8.29 (dd, J=2.0, 6.9 Hz, 1H)

EXAMPLE 95

2-(2,3,4-Trifluoroanilino)propanol 2-(2,3,4-Trifluoroanililno)propyl 4-nitrobenzoate (50 mg) and potassium hydroxide (11.8 mg) were added to methanol (2 ml) and dissolved by stirring. Then the mixture was stirred at room temperature for 18 hours. After evaporating methanol under reduced pressure, chloroform (5 ml) and water (5 ml) were added and the resultant mixture was separated. The chloroform layer was concentrated and purified by silica gel column chromatography to thereby give 19.8 mg (69.1%) of the title compound as a colorless oily product.

$^1$H-NMR (270 MHz, CDCl$_3$) δ: 1.22 (d, J=5.9 Hz, 3H), 3.55–3.74 (m, 4H), 6.3–6.5 (m, 1H), 6.76–6.87 (m, 1H).

EXAMPLE 96

2-Hydroxypropyl 4-nitrobenzoate

2-Hydroxypropanol (4.57 g) was dissolved in toluene (80 ml) by stirring and triethylamine (6.68 g) was dropped thereinto at 0° C. After stirring at the same temperature for 30 minutes, a solution of p-nitrobenzoyl chloride (11.4 g) dissolved in toluene (12 ml) was slowly added thereto. The resultant mixture was heated to room temperature and stirred for 2 hours. Next, dichloromethane (50 ml) was added and the crystals thus precipitated were dissolved. The solution was washed with an dilute aqueous solution of sodium hydrogencarbonate (100 ml) and then with an aqueous solution of hydrochloric acid (0.5 mol/l). The organic layer thus obtained was concentrated and the residue was dissolved in toluene (45 ml) by heating. Then it was cooled by allowed to stand at room temperature for crystallization. The crystals thus precipitated were collected by filtration and dried under reduced pressure to give 6.90 g (51%) of the title compound as yellow crystals.

$^1$H-NMR (270 MHz, CDCl$_3$) δ: 1.32 (d, 3.6 Hz, 3H), 4.24–4.42 (m, 3H), 8.22–8.33 (m, 4H)

EXAMPLE 97

(3S)-(−)-9,10-Difluoro-3-methyl-7-oxo-2,3-dihydro-
7H-pyrido[1,2,3-de][1,4]benzoxazine-6-carboxylic
acid ethyl ester To S-(−)-7,8-difluoro-3-methyl-2,3-dihydro-4H-[1,4]benzoxazine (15.8 g) was added diethyl ethoxymethylenemalonate (24.0 g) and the mixture was stirred under reduced pressure at 130 to 140° C. for 1 hour. After cooling, the liquid reaction mixture was dissolved in acetic anhydride (50 ml). Under ice-cooling and stirring, a liquid mixture (80 ml) of acetic anhydride-concentrated sulfuric acid (2:1, V/V) was added in portions thereto. After stirring at room temperature for 1 hour, it was stirred at a bath temperature of 50 to 60° C. for 30 minutes. After adding ice water, the liquid reaction mixture was neutralized by adding powdery potassium carbonate and extracted with chloroform. The extract was washed successively with a saturated aqueous solution of sodium hydrogencarbonate and a saturated aqueous solution of sodium chloride and dried over mirabilite.

After evaporating chloroform, diethyl ether was added to the residue. The crystals were collected by filtration to give 20.0 g of the title compound.

Melting point: 257 to 258° C.
$[\alpha]_D=-68.1°$ (c=0.250, acetic acid)

EXAMPLE 98

(3S)-(−)-9,10-Difluoro-3-methyl-7-oxo-2,3-dihydro-7H-pyrido[1,2,3-de][1,4]benzoxazine-6-carboxylic acid The ester compound (19.5 g) obtained above was dissolved in acetic acid (150 ml). After adding conc. hydrochloric acid (400 ml), the mixture was refluxed for 3 hours. After cooling, the crystals thus precipitated were collected by filtration and washed successively with water, ethanol and diethyl ether followed by drying to give 16.2 g of the title carboxylic acid.

Melting point>300° C.
$[\alpha]_D=-65.6°$ (c=0.985, DMSO)

EXAMPLE 99

(3S)-(−)-9-Fluoro-3-methyl-10-(4-methyl-1-piperazinyl)-7-oxo-2,3-dihydro-7H-pyrido[1,2,3-de][1,4]benzoxazine-6-carboxylic acid (levofloxacin)

The carboxylic acid (14.3 g) obtained above was suspended in diethyl ether (600 ml). After adding boron trifluoride diethyl ether complex (70 ml), the mixture was stirred at room temperature for 5 hours. After discarding the supernatant by decantation, the residue was collected by filtration by adding diethyl ether and washed with diethyl ether followed by drying. Then it was dissolved in dimethyl sulfoxide (100 ml). After adding triethylamine (14.2 ml) and N-methylpiperazine (7.3 ml), the mixture was stirred at room temperature for 18 hours. After evaporating the solvent under reduced pressure, diethyl ether was added to the residue. The yellow powder thus collected by filtration was suspended in 95% methanol (400 ml) and triethylamine (25 ml) was added thereto. After heating under reflux for 25 hours, the solvent was evaporated under reduced pressure. The residue was dissolved in 10% hydrochloric acid (500 ml), washed with chloroform thrice and then adjusted to pH 11 with an aqueous solution of sodium hydroxide (4 mol/l). Next, it was adjusted again to pH 7.3 with hydrochloric acid (1 mol/l), extracted with chloroform (2000 ml×3) and dried over mirabilite. After evaporating the chloroform, the crystalline solid thus obtained was recrystallized from ethanol-diethyl ether to thereby give 12.0 g of the title compound (levofloxacin).

Melting point: 226 to 230° C. (decomposition)
$[\alpha]_D=-76.9°$ (c=0.655, NaOH (0.05 mol/l))

EXAMPLE 100

(3S)-(−)-9-Fluoro-3-methyl-10-(4-methyl-1-piperazinyl)-7-oxo-2,3-dihydro-7H-pyrido[1,2,3-de][1,4]benzoxazine-6-carboxylic acid (levofloxacin)

(S)-(−)-9,10-Difluoro-3-methyl-7-oxo-2,3-dihydro-7H-pyrido[1,2,3-de][1,4]benzoxazine-6-carboxylic acid (281 mg) was dissolved in diethyl ether (30 ml). Under stirring at room temperature, boron trifluoride diethyl ether complex in large excess was added thereto and the mixture was reacted for 45 minutes. The precipitate was collected by filtration, washed with diethyl ether and dried under reduced pressure to thereby give a boron chelate compound.

Decomposition point>300° C.
$[\alpha]_D=-9.4°$ (c=0.490, DMSO)
Elemental analysis as $C_{13}H_8BF_4NO_4$

| | |
|---|---|
| Calculated (%): | C, 47.46; H, 2.46; N, 4.26 |
| Found (%): | C, 47.68; H, 2.59; N, 4.32 |

This chelate compound (310 mg) was dissolved in dimethyl sulfoxide (6 ml) and triethylamine (0.32 ml) and N-methylpiperazine (0.13 ml) were added thereto. The resultant mixture was stirred at room temperature for 17 hours and then solidified to dryness under reduced pressure. The residue was washed with diethyl ether and dissolved in 95% ethanol (20 ml) containing triethylamine (0.5 ml) followed by heating under reflux for 8 hours. After cooling, the residue obtained by solidifying to dryness was dissolved in dilute hydrochloric acid (5%) and separated by shaking together with chloroform. The aqueous layer was adjusted to pH 11 with sodium hydroxide (1 mol/l) and then to pH 7.4 with hydrochloric acid (1 mol/l). Then it was extracted with chloroform (50 ml×3) and dried over mirabilite. After evaporating chloroform, the powder thus obtained was recrystallized from ethanol-diethyl ether to thereby give 120 mg of the title compound as transparent fine needles.

Melting point: 225 to 227° C. (decomposition)
Elemental analysis as $C_{18}H_{20}FN_3O_4$

| | |
|---|---|
| Calculated (%): | C, 58.37; H, 5.72; N, 11.35 |
| Found (%): | C, 58.17; H, 5.58; N, 11.27 |

EXAMPLE 101

(3S)-9,10-Difluoro-3-methyl-7-oxo-2,3-dihydro-7H-pyrido[1,2,3-de][1,4]benzoxazine-6-carboxylic acid boron difluoride chelate complex (S)-Diethyl (7,8-difluoro-3-methyl-3,4-dihydro-2H-[1,4]benzoxazin-4-yl)methylenemalonate (2 g) was mixed with acetic anhydride (2 ml). At 140° C., 47% boron trifluoride/tetrahydrofruan complex (0.8 ml) was added thereto and the resultant mixture was stirred under heating at the same temperature for 1 hour. After evaporating the low-boiling matters thus formed, the liquid reaction mixture was cooled to room temperature. After adding acetone (10 ml), the liquid reaction mixture was stirred at the same temperature for 30 minutes. The crystals thus precipitated were collected and washed with acetone to give 1.55 g of the title compound.

EXAMPLE 102

(3S)-(−)-9-Fluoro-3-methyl-10-(4-methyl-1-piperazinyl)-7-oxo-2,3-dihydro-7H-pyrido[1,2,3-de][1,4]benzoxazine-6-carboxylic acid (levofloxacin)

(S)-(−)-9,10-Difluoro-3-methyl-7-oxo-2,3-dihydro-7H-pyrido[1,2,3-de][1,4]benzoxazine-6-carboxylic acid (21 mg) and N-methylpiperazine (30 mg) were dissolved in anhydrous dimethyl sulfoxide (3 ml) and stirred at 130 to 140° C. for 1 hour. After evaporating the solvent, ethanol (2 ml) was added to the residue. The solid thus precipitated was collected by filtration and washed successively with a small amount of ethanol and ether. 14 mg of the obtained powder was subjected to silica gel column chromatography with the use of 5 g of silica gel and eluted with a lower layer solution of chloroform-methanol-water (7:3:1) to thereby give (S)-(−)-9-fluoro-3-methyl-10-(4-methyl-1-piperazinyl)-7-oxo-2,3-dihydro-7H-pyrido[1,2,3-de][1,4]benzoxazine-6-carboxylic acid. The above-described filtration mother liquor was fractioned and subjected to thin layer chromatography (silica gel, 20×20 cm, 0.5 mm), thereby purifying by developing with a lower layer solution of chloroform-methanol-water (15:3:1). The products were combined to thereby give 14 mg of crystals of the target compound. Melting point: 220 to 228° C. (decomposition).

Elemental analysis as $C_{18}H_{20}FN_3O_4$

| Calculated (%): | C, 59.82; H, 5.58; N, 11.63 |
| --- | --- |
| Found (%): | C, 60.01; H, 5.69; N, 11.53 |

MS(m/e); 361(M+)

$^1$H-NMR (CDCL$_3$) δ (ppm): 1.63 (3H, d, J=7 Hz), 2.38 (3H, s), 2.54–2.60 (4H, m), 3.40–3.44 (4H, m), 4.35–4.52 (3H, m), 7.76 (1H, d), 8.64 (1H, s).

What is claimed is:

1. A process for producing a compound represented by the following formula:

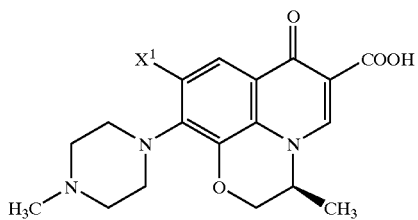

which comprises comprising obtaining a compound represented by formula (VI-a) by any of the following Processes A to J:

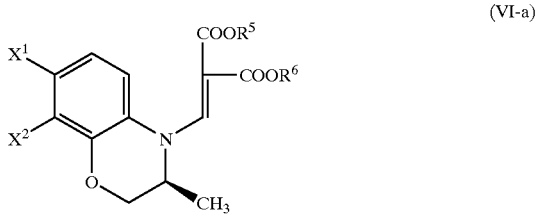
(VI-a)

treating this compound with a boron trifluoride compound to thereby convert it into a boron chelate compound represented by the following formula:

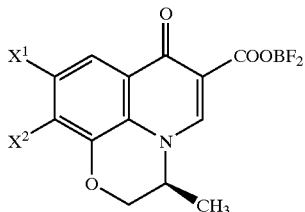

reacting this compound with 4-methylpiperazine to give a compound represented by the following formula:

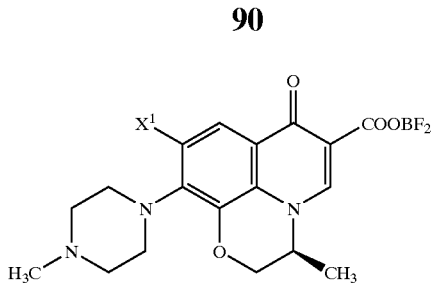

and then cleaving and eliminating the boron chelate of this compound:

Process A:

a process which comprises reacting a compound represented by formula (I):

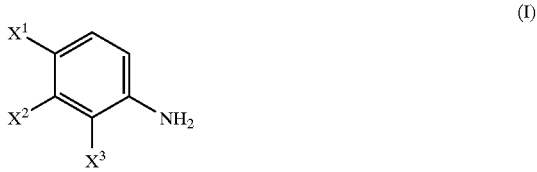
(I)

with a compound represented by formula (II-1-a) in the presence of a base:

(II-1-a)

to give a compound represented by the formula (III-1-a):

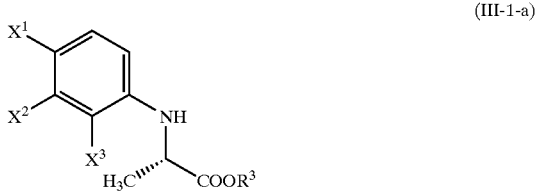
(III-1-a)

reducing this compound into a compound represented by formula (IV-a):

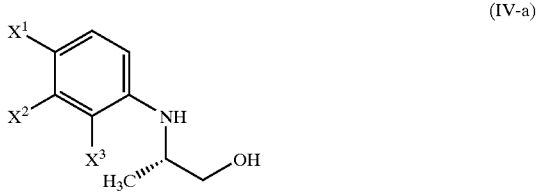
(IV-a)

reacting this compound with a compound represented by the following formula:

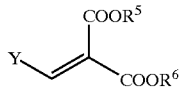

to give a compound represented by the formula (V-a):

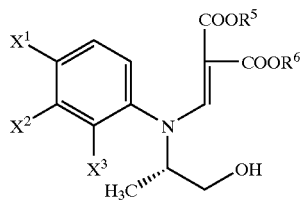
(V-a)

and then treating this compound in the presence of a base;

Process B:

a process which comprises reacting a compound represented by formula (I):

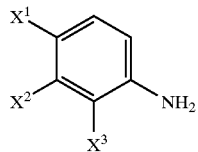
(I)

with a compound represented by formula (II-2-a) in the presence of a base:

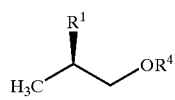
(II-2-a)

to give a compound represented by formula (III-2-a):

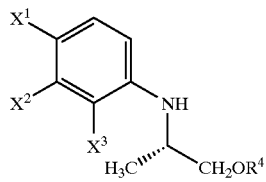
(III-2-a)

eliminating the hydroxyl-protective group of this compound to give a compound represented by formula (IV-a):

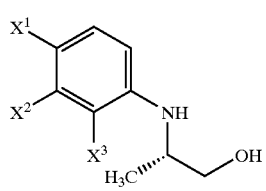
(IV-a)

reacting this compound with a compound represented by the following formula:

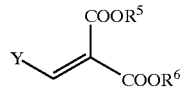

to give a compound represented by the formula (V-a):

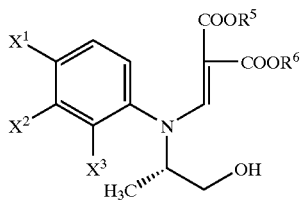
(V-a)

and then treating this compound in the presence of a base;

Process C;

a process which comprises reacting a compound represented by formula (I):

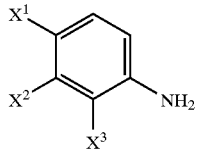
(I)

with a compound represented by formula (II-1-a) in the presence of a base:

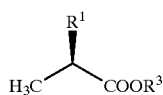
(II-1-a)

to give a compound represented by formula (III-1-a):

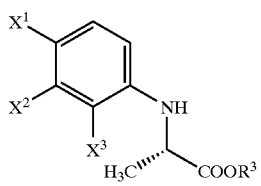
(III-1-a)

reducing this compound into a compound represented by formula (IV-a):

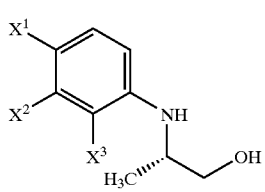
(IV-a)

treating this compound in the presence of a base to give a compound represented by the formula (VII-a):

(VII-a)

and reacting this compound with a compound represented by the following formula;

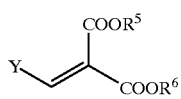

Process D:

a process which comprises reacting a compound represented by formula (1):

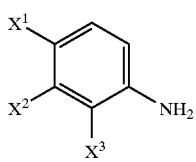
(I)

with a compound represented by formula (II-2-a) in the presence of a base:

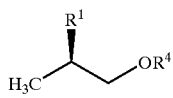
(II-2-a)

to give a compound represented by formula (III-2-a):

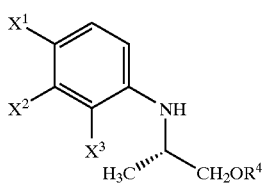
(III-2-a)

eliminating the hydroxyl-protective group of this compound to give a compound represented by formula (IV-a):

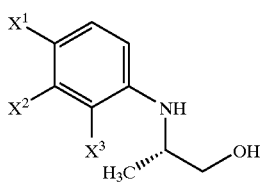
(IV-a)

treating this compound in the presence of a base to give a compound represented by formula (VII-a):

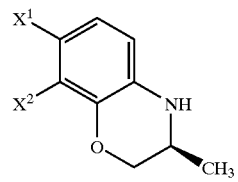
(VII-a)

and then reacting this compound with a compound represented by the following formula:

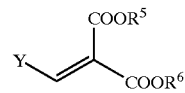

Process E:

a process which comprises reacting a compound represented by formula (I):

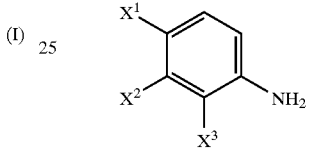
(I)

with a compound represented by formula (II-1) in the presence of a base:

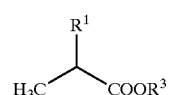
(II-1)

to give a compound represented by formula (III-1):

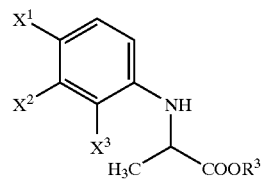
(III-1)

and then subjecting this compound to the following Method 1 or 2;

Method 1:
in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism capable of asymmetrically hydrolyzing an ester and, after the completion of this treatment, isolating the product from the treated liquid mixture;

Method 2:
in case of the compound represented by the formula (III-1) where R3 is a hydrogen atom, a method which comprises optically resolving this compound by reacting with an optically active organic base;

to obtain a carboxylic acid compound represented by the following formula:

[Structure: X¹, X², X³-substituted phenyl-NH-CH(CH₃)-COOH]

esterifying this compound in the presence of an alcohol represented by the following formula:

R⁷—OH to give an ester compound represented by the following formula:

[Structure: X¹, X², X³-substituted phenyl-NH-CH(CH₃)-COOR⁷]

reducing the compound into a compound represented by formula (IV-a):

[Structure: X¹, X², X³-substituted phenyl-NH-CH(CH₃)-CH₂OH] (IV-a)

reacting this compound with a compound represented by the following formula:

[Structure: Y-CH=C(COOR⁵)(COOR⁶)]

to give a compound represented by formula (V-a):

[Structure: X¹, X², X³-substituted phenyl-N(CH(CH₃)CH₂OH)-CH=C(COOR⁵)(COOR⁶)] (V-a)

and then treating this compound in the presence of a base;

Process F:

a process which comprises reacting a compound represented by formula (I):

[Structure: X¹, X², X³-substituted phenyl-NH₂] (I)

with a compound represented by formula (II-1) in the presence of a base:

[Structure: R¹-CH(CH₃)-COOR³] (II-1)

to give a compound represented by formula (III-1):

[Structure: X¹, X², X³-substituted phenyl-NH-CH(CH₃)-COOR³] (III-1)

and then subjecting this compound to the following Method 1 or 2;

Method 1:

in case of the compound represented by the formula (III-1) where R³ is not a hydrogen atom, a method which comprises treating this compound with an enzyme capable of asymmetrically hydrolyzing an ester or a liquid culture medium of a microorganism, cells of this microorganism or processed cells of this microorganism capable of asymmetrically hydrolyzing an ester and, after the completion of this treatment, isolating the product from the treated liquid mixture;

Method 2:

in case of the compound represented by the formula (III-1) where R³ is a hydrogen atom, a method which comprises optically resolving this compound by reacting with an optically active organic base;

to obtain a carboxylic acid compound represented by the following formula:

[Structure: X¹, X², X³-substituted phenyl-NH-CH(CH₃)-COOH]

esterifying this compound in the presence of an alcohol represented by the following formula:

R⁷—OH to give an ester compound represented by the following formula:

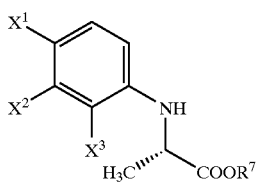

reducing the compound into a compound represented by formula (IV-a):

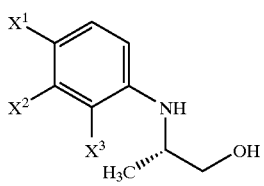
(IV-a)

treating this compound in the presence of a base to give a compound represented by formula (VII-a):

(VII-a)

and then reacting this compound with a compound represented by the following formula;

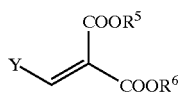

Process G:
a process which comprises reacting a compound represented by the following formula:

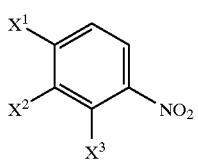

or by the following formula:

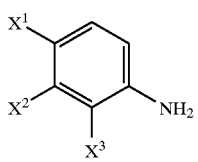

with a compound represented by the following formula in the presence of a metal catalyst under a hydrogen gas atmosphere, optionally in the presence of a dehydrating agent or an acid:

CH$_3$COCOOR$^3$ to give a compound represented by formula (III-1):

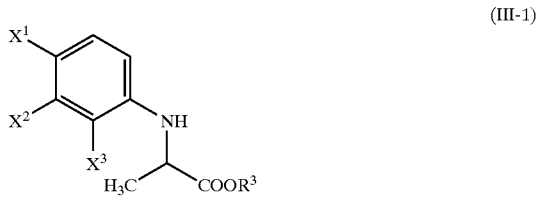
(III-1)

and then subjecting this compound to the following Method 1 or 2;

Method 1:
in case of the compound represented by the formula (III-1) where R$^3$ is not a hydrogen atom, a method which comprises treating this compound with an enzyme capable of asymmetrically hydrolyzing an ester or a liquid culture medium of a microorganism, cells of this microorganism or processed cells of this microorganism capable of asymmetrically hydrolyzing an ester and, after the completion of this treatment, isolating the product from the treated liquid mixture;

Method 2:
in case of the compound represented by the formula (III-1) where R$^3$ is a hydrogen atom, a method which comprises optically resolving this compound by reacting with an optically active organic base;

to obtain a carboxylic acid compound represented by the following formula:

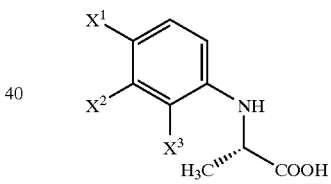

esterifying this compound in the presence of an alcohol represented by the following formula:

R$^7$—OH to give an ester compound represented by the following formula:

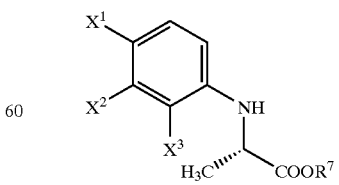

reducing the compound into a compound represented by formula (IV-a):

(IV-a)

[Structure: X¹, X², X³ substituted phenyl-NH-CH(CH₃)-CH₂OH]

reacting this compound with a compound represented by the following formula:

[Structure: Y-CH=C(COOR⁵)(COOR⁶)]

to give a compound represented by the formula (V-a):

(V-a)

[Structure: X¹, X², X³ substituted phenyl-N(CH=C(COOR⁵)(COOR⁶))-CH(CH₃)-CH₂OH]

and then treating this compound in the presence of a base;

Process H:

a process which comprises reacting a compound represented by the following formula:

[Structure: X¹, X², X³ substituted nitrobenzene with NO₂]

or by the following formula:

[Structure: X¹, X², X³ substituted aniline with NH₂]

with a compound represented by the following formula in the presence of a metal catalyst under a hydrogen gas atmosphere, optionally in the presence of a dehydrating agent or an acid:

CH₃COCOOR³ to give a compound represented by formula (III-1):

(III-1)

[Structure: X¹, X², X³ substituted phenyl-NH-CH(CH₃)-COOR³]

and then subjecting this compound to the following Method 1 or 2;

Method 1:
in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism capable of asymmetrically hydrolyzing an ester and, after the completion of this treatment, isolating the product from the treated liquid mixture;

Method 2:
in case of the compound represented by the formula (III-1) where $R^3$ is a hydrogen atom, a method which comprises optically resolving this compound by reacting with an optically active organic base;

to obtain a carboxylic acid compound represented by the following formula:

[Structure: X¹, X², X³ substituted phenyl-NH-CH(CH₃)-COOH]

esterifying this compound in the presence of an alcohol represented by the following formula:

R⁷—OH to give an ester compound represented by the following formula:

[Structure: X¹, X², X³ substituted phenyl-NH-CH(CH₃)-COOR⁷]

reducing the compound into a compound represented by formula (IV-a):

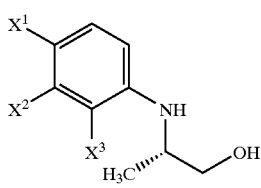
(IV-a)

treating this compound in the presence of abase to give a compound represented by formula (VII-a):

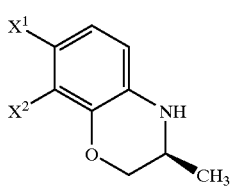
(VII-a)

and then reacting this compound with a compound represented by the following formula;

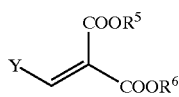

Process I:

a process which comprises reacting a compound represented by the following formula:

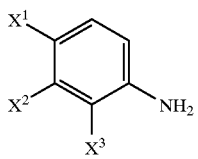

with a compound represented by the following formula:

$CH_3COCOOR^3$ to give a compound represented by the following formula:

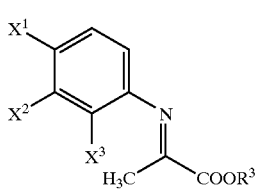

asymmetrically reducing this compound into a compound represented by formula (III-1-a):

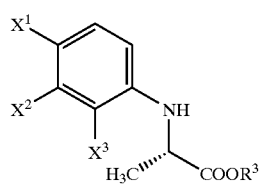
(III-1-a)

reducing this compound into a compound represented by formula (IV-a):

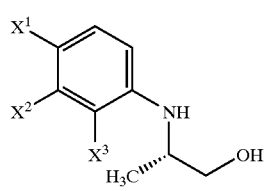
(IV-a)

reacting this compound with a compound represented by the following formula:

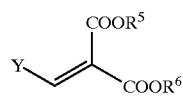

to give a compound represented by the formula (V-a):

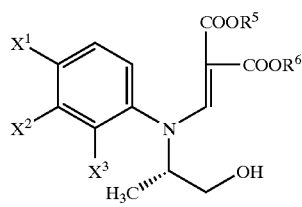
(V-a)

and then treating this compound in the presence of a base; and

Process J:

a process which comprises reacting a compound represented by the following formula:

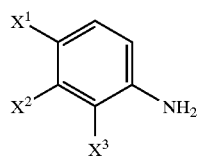

with a compound represented by the following formula:

$CH_3COCOOR^3$ to give a compound represented by the following formula:

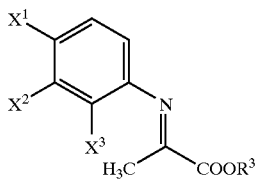

asymmetrically reducing this compound into a compound represented by formula (III-1-a):

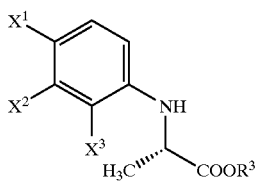

(III-1-a)

reducing this compound into a compound represented by formula (IV-a):

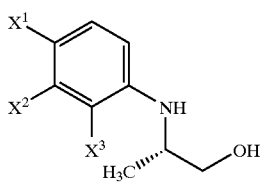

(IV-a)

treating this compound in the presence of a base to give a compound represented by formula (VII-a):

(VII-a)

and then reacting this compound with a compound represented by the following formula:

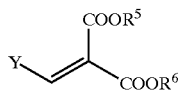

in each of the above formulae, $X^1$, $X^2$ and $X^3$, each independently represents a halogen atom; $R^1$ represents a leaving group; $R^3$ represents a hydrogen atom or a carboxyl-protective group; $R^4$ represents a hydroxyl-protective group; $R^5$ and $R^6$, each independently represents an alkyl group having 1 to 6 carbon atoms; $R^7$ represents a carboxyl-protective group; and Y represents an alkoxy group having 1 to 6 carbon atoms, a halogen atom or a dialkylamino group (wherein the alkyl groups may be the same or different and each represents an alkyl group having 1 to 6 carbon atoms).

2. The process as claimed in claim 1 wherein the process for producing the compound represented by the formula (VI-a) is Process A.

3. The process as claimed in claim 1 wherein the process for producing the compound represented by the formula (VI-a) is Process B.

4. The process as claimed in claim 1 wherein the process for producing the compound represented by the formula (VI-a) is Process C.

5. The process as claimed in claim 1 wherein the process for producing the compound represented by the formula (VI-a) is Process D.

6. The process as claimed in claim 1 wherein the process for producing the compound represented by the formula (VI-a) is Process E.

7. The process as claimed in claim 1 wherein the process for producing the compound represented by the formula (VI-a) is Process F.

8. The process as claimed in claim 1 wherein the process for producing the compound represented by the formula (VI-a) is Process G.

9. The process as claimed in claim 1 wherein the process for producing the compound represented by the formula (VI-a) is Process H.

10. The process as claimed in claim 1 wherein the process for producing the compound represented by the formula (VI-a) is Process I.

11. The process as claimed in claim 1 wherein the process for producing the compound represented by the formula (VI-a) is Process J.

12. A process as claimed in any of claims 1 to 11 wherein $X^1$ and $X^2$ are both fluorine atoms.

13. The process as claimed in claim 12 wherein the boron trifluoride compound is a boron trifluoride compound composed of boron trifluoride and an ether compound.

14. The process as claimed in claim 13 wherein the boron trifluoride compound is boron trifluoride diethyl ether complex or boron trifluoride tetrahydrofruan complex.

15. The process as claimed in claim 14 wherein the reaction of 4-methylpiperazine is a reaction in the presence of a trialkylamine.

16. The process as claimed in claim 15 wherein the trialkylamine is triethylamine or tributylamine.

17. A process for producing a compound represented by the following formula:

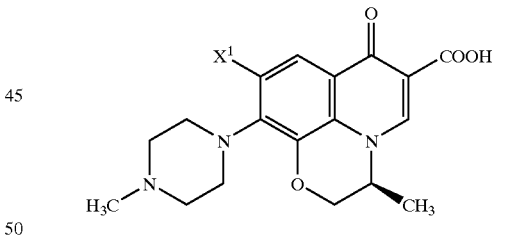

which comprises comprising obtaining a compound represented by formula (VI-a) by any of the following Processes A to J:

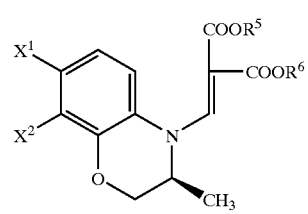

(VI-a)

treating this compound with a boron trifluoride compound to thereby convert it into a boron chelate compound represented by the following formula:

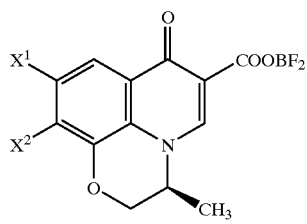

reacting this compound with 4-methylpiperazine to give a compound represented by the following formula:

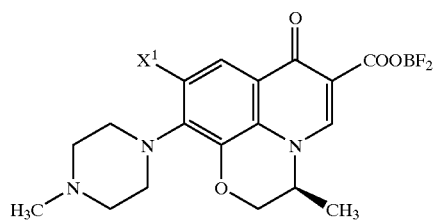

and then cleaving and eliminating the boron chelate of this compound:

Process A:

a process which comprises reacting a compound represented by formula (I):

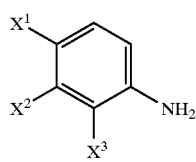

(I)

with a compound represented by formula (II-1-a) in the presence of a base:

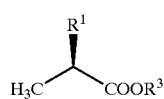

(II-1-a)

to give a compound represented by the formula (III-1-a):

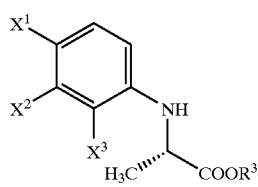

(III-1-a)

reducing this compound into a compound represented by formula (IV-a):

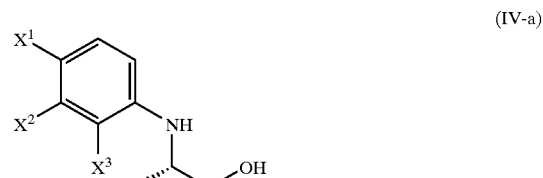

(IV-a)

reacting this compound with a compound represented by the following formula:

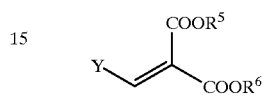

to give a compound represented by the formula (V-a):

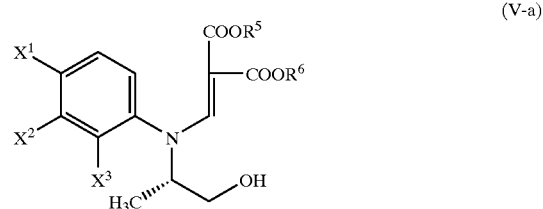

(V-a)

and then treating this compound in the presence of a base;

Process B:

a process which comprises reacting a compound represented by formula (I):

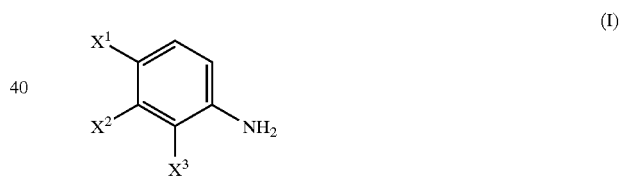

(I)

with a compound represented by formula (II-2-a) in the presence of a base:

(II-2-a)

to give a compound represented by formula (III-2-a):

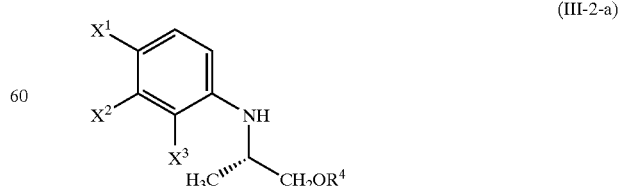

(III-2-a)

eliminating the hydroxyl-protective group of this compound to give a compound represented by formula (IV-a):

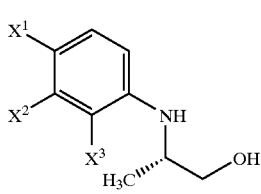

(IV-a)

reacting this compound with a compound represented by the following formula:

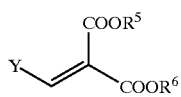

to give a compound represented by the formula (V-a):

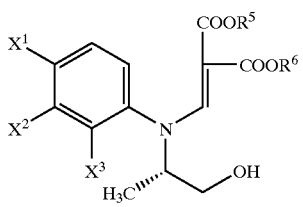

(V-a)

and the treating this compound in the presence of a base;

Process C:

a process which comprises reacting a compound represented by formula (I):

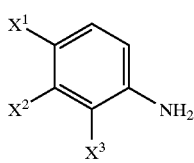

(I)

with a compound represented by formula (II-1-a) in the presence of a base:

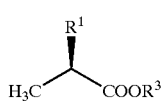

(II-1-a)

to give a compound represented by formula (III-1-a):

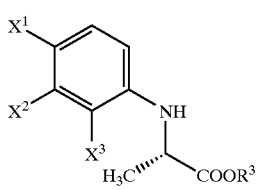

(III-1-a)

reducing this compound into a compound represented by formula (IV-a):

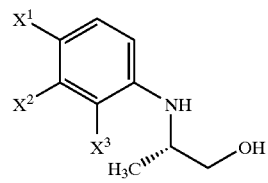

(IV-a)

treating this compound in the presence of a base to give a compound represented by the formula (VII-a):

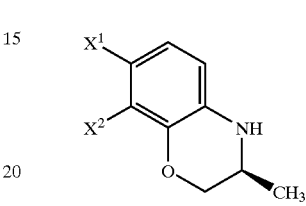

(VII-a)

and reacting this compound with a compound represented by the following formula;

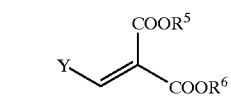

Process D:

a process which comprises reacting a compound represented by formula (I):

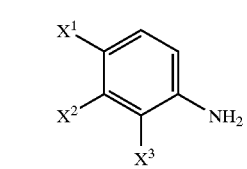

(I)

with a compound represented by formula (II-2-a) in the presence of a base:

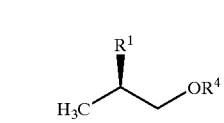

(II-2-a)

to give a compound represented by formula (III-2-a):

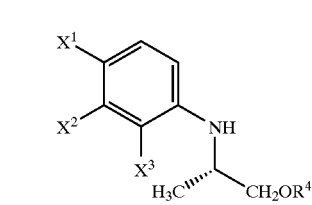

(III-2-a)

eliminating the hydroxyl-protective group of this compound to give a compound represented by formula (IV-a):

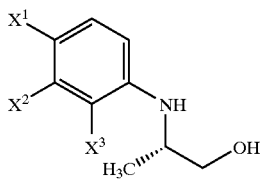
(IV-a)

treating this compound in the presence of a base to give a compound represented by formula (VII-a):

(VII-a)

and then reacting this compound with a compound represented by the following formula:

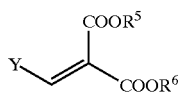

Process E:
   a process which comprises reacting a compound represented by formula (I):

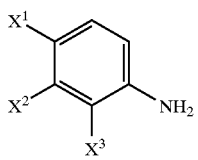
(I)

with a compound represented by formula (II-1) in the presence of a base:

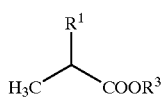
(II-1)

to give a compound represented by formula (III-1):

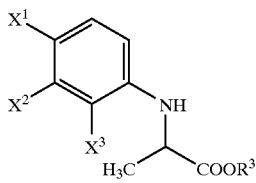
(III-1)

and then subjecting this compound to the following Method 1 or 2;

Method 1:
   in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism and, after the completion of this treatment, isolating the product from the treated liquid mixture;

Method 2:
   in case of the compound represented by the formula (III-1) where $R^3$ is a hydrogen atom, a method which comprises optically resolving this compound by reacting with an optically active organic base;

to obtain a carboxylic acid compound represented by the following formula:

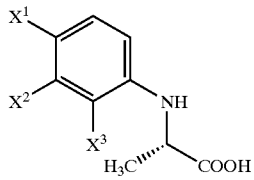

esterifying this compound in the presence of an alcohol represented by the following formula:

$R^7$-OH to give an ester compound represented by the following formula:

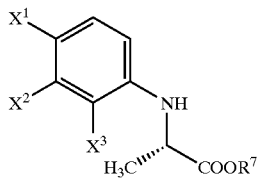

reducing the compound into a compound represented by formula (IV-a):

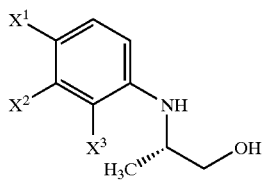
(IV-a)

reacting this compound with a compound represented by the following formula:

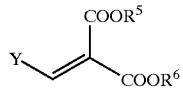

to give a compound represented by formula (V-a):

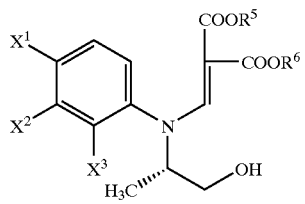
(V-a)

and then treating this compound in the presence of a base;

Process F:

a process which comprises reacting a compound represented by formula (I):

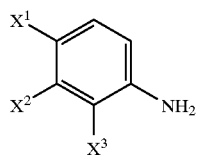
(I)

with a compound represented by formula (II-1) in the presence of a base:

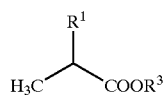
(II-1)

to give a compound represented by formula (III-1):

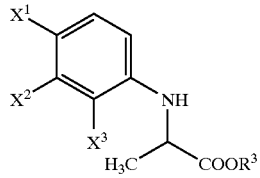
(III-1)

and then subjecting this compound to the following Method 1 or 2;

Method 1:
in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism and, after the completion of this treatment, isolating the product from the treated liquid mixture;

Method 2:
in case of the compound represented by the formula (III-1) where $R^3$ is a hydrogen atom, a method which comprises optically resolving this compound by reacting with an optically active organic base;

to obtain a carboxylic acid compound represented by the following formula:

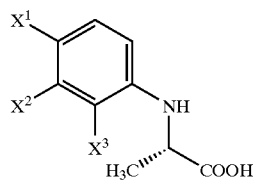

esterifying this compound in the presence of an alcohol represented by the following formula:

$R^7$-OH to give an ester compound represented by the following formula:

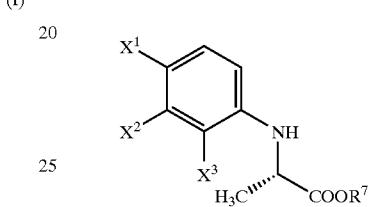

reducing the compound into a compound represented by formula (IV-a):

(IV-a)

treating this compound in the presence of a base to give a compound represented by formula (VII-a):

(VII-a)

and then reacting this compound with a compound represented by the following formula;

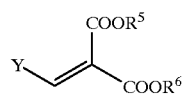

Process G:

a process which comprises reacting a compound represented by the following formula:

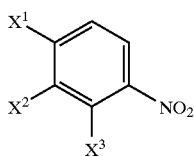

or by the following formula:

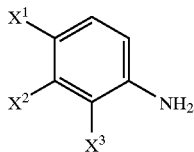

with a compound represented by the following formula in the presence of a metal catalyst under a hydrogen gas atmosphere, optionally in the presence of a dehydrating agent or an acid:

CH₃COCOOR³ to give a compound represented by formula (III-1):

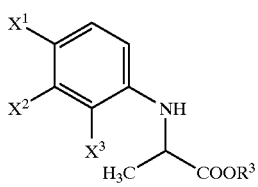

(III-1)

and then subjecting this compound to the following Method 1 or 2;

Method 1:
in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism and, after the completion of this treatment, isolating the product from the treated liquid mixture;

Method 2:
in case of the compound represented by the formula (III-1) where $R^3$ is a hydrogen atom, a method which comprises optically resolving this compound by reacting with an optically active organic base;

to obtain a carboxylic acid compound represented by the following formula:

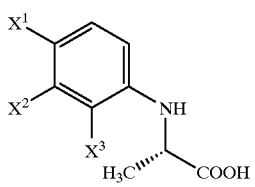

esterifying this compound in the presence of an alcohol represented by the following formula:

R⁷-OH to give an ester compound represented by the following formula:

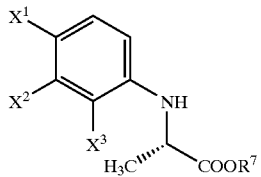

reducing the compound into a compound represented by formula (IV-a):

(IV-a)

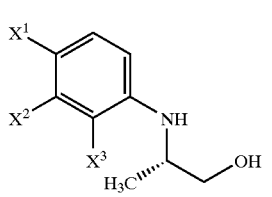

reacting this compound with a compound represented by the following formula:

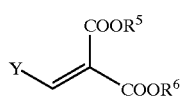

to give a compound represented by the formula (V-a):

(V-a)

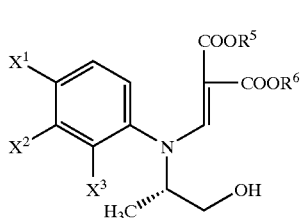

and then treating this compound in the presence of a base;

Process H:
a process which comprises reacting a compound represented by the following formula:

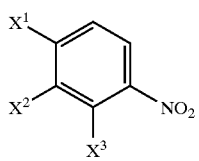

or by the following formula:

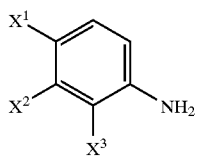

with a compound represented by the following formula in the presence of a metal catalyst under a hydrogen gas atmosphere, optionally in the presence of a dehydrating agent or an acid:

to give a compound represented by formula (III-1):

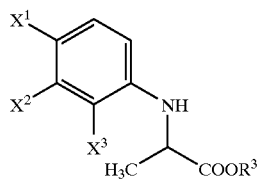
(III-1)

and then subjecting this compound to the following Method 1 or 2;

Method 1:
in case of the compound represented by the formula (III-1) where $R^3$ is not a hydrogen atom, a method which comprises treating this compound with an enzyme capable of asymmetrically hydrolyzing an ester or a liquid culture medium of a microorganism, cells of this microorganism or processed cells of this microorganism and, after the completion of this treatment, isolating the product from the treated liquid mixture;

Method 2:
in case of the compound represented by the formula (III-1) where $R^3$ is a hydrogen atom, a method which comprises optically resolving this compound by reacting with an optically active organic base;

to obtain a carboxylic acid compound represented by the following formula:

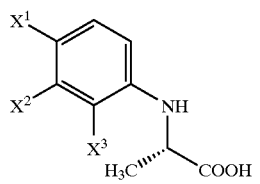

esterifying this compound in the presence of an alcohol represented by the following formula:

to give an ester compound represented by the following formula:

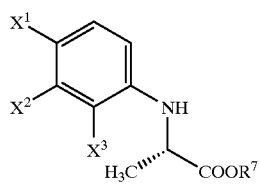

reducing the compound into a compound represented by formula (IV-a):

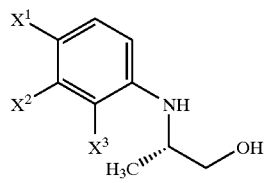
(IV-a)

treating this compound in the presence of a base to give a compound represented by formula (VII-a):

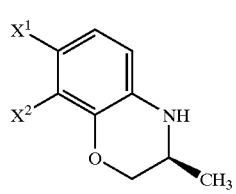
(VII-a)

and then reacting this compound with a compound represented by the following formula;

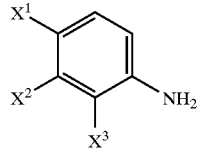

Process I:

a process which comprises reacting a compound represented by the following formula:

with a compound represented by the following formula:

$CH_3COCOOR^3$ to give a compound represented by the following formula:

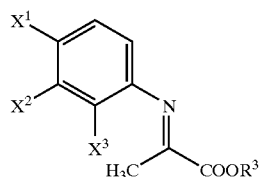

asymmetrically reducing this compound into a compound represented by formula (III-1-a):

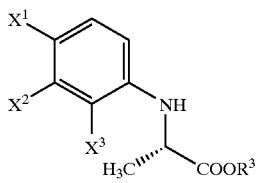

(III-1-a)

reducing this compound into a compound represented by formula (IV-a):

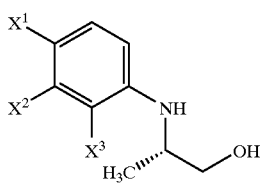

(IV-a)

reacting this compound with a compound represented by the following formula:

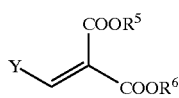

to give a compound represented by the formula (V-a):

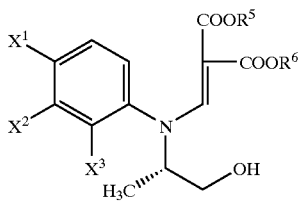

(V-a)

and then treating this compound in the presence of a base; and

Process J:

a process which comprises reacting a compound represented by the following formula:

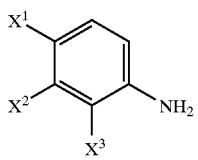

with a compound represented by the following formula:

$CH_3COCOOR^3$ to give a compound represented by the following formula:

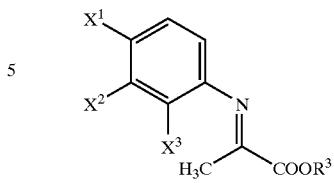

asymmetrically reducing this compound into a compound represented by formula (III-1-a):

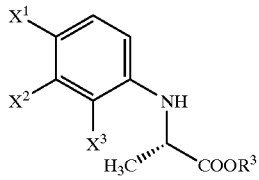

(III-1-a)

reducing this compound into a compound represented by formula (IV-a):

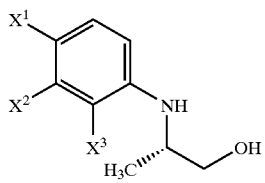

(IV-a)

treating this compound in the presence of a base to give a compound represented by formula (VII-a):

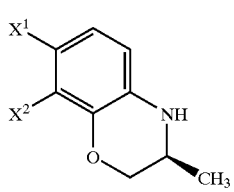

(VII-a)

and then reacting this compound with a compound represented by the following formula:

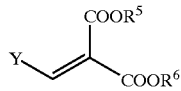

in each of the above formulae, $X^1$, $X^2$ and $X^3$, each independently represents a halogen atom; $R^1$ represents a leaving group; $R^3$ represents a hydrogen atom or a carboxyl-protective group; $R^4$ represents a hydroxyl-protective group; $R^5$ and $R^6$, each independently represents an alkyl group having 1 to 6 carbon atoms; $R^7$ represents a carboxyl-protective group; and Y represents an alkoxy group having 1 to 6 carbon atoms, a halogen atom or a dialkylamino group (wherein the alkyl groups may be the same or different and each represents an alkyl group having 1 to 6 carbon atoms), wherein said Method 1 of said Processes E, F, G, and H comprises treating the compound represented by the formula (III-1), where $R^3$ is not a hydrogen atom, with an enzyme capable of asymmetrically hydrolyzing an ester or a liquid culture medium of a microorganism, cells of this microorganism or processed cells of this microorganism and, after the completion of this treatment, isolating the product from the treated liquid mixture, wherein the enzyme is selected from the group consisting of an esterase, a protease and a chymotrypsin, and the microorganism is selected from the group consisting of bacteria belonging to the genera *Bacillus, Micrococcus* and *Actinomyces, fungi belonging to the genera Aspergillus, Rhizopus, Nannizia* and *Penicillium,* and yeasts belonging to the genera *Candida, Saccharomyces* and *Zygoascus.*

* * * * *